United States Patent
Blackman et al.

(10) Patent No.: US 9,205,086 B2
(45) Date of Patent: Dec. 8, 2015

(54) CANCER THERAPY USING A COMBINATION OF A HSP90 INHIBITORY COMPOUNDS AND A EGFR INHIBITOR

(75) Inventors: Ronald K. Blackman, Brookline, MA (US); Kevin Paul Foley, Waltham, MA (US); David Proia, Newton, MA (US)

(73) Assignee: Synta Pharmaceuticals Corp., Lexington, MA (US)

(*) Notice: Subject to any disclaimer, the term of this patent is extended or adjusted under 35 U.S.C. 154(b) by 0 days.

(21) Appl. No.: 13/642,068

(22) PCT Filed: Apr. 19, 2011

(86) PCT No.: PCT/US2011/033008
§ 371 (c)(1),
(2), (4) Date: Feb. 22, 2013

(87) PCT Pub. No.: WO2011/133520
PCT Pub. Date: Oct. 27, 2011

(65) Prior Publication Data
US 2013/0150385 A1    Jun. 13, 2013

Related U.S. Application Data

(60) Provisional application No. 61/342,820, filed on Apr. 19, 2010.

(51) Int. Cl.
*A61K 31/44* (2006.01)
*A61K 31/517* (2006.01)
*A61K 31/4196* (2006.01)
*A61K 31/675* (2006.01)

(52) U.S. Cl.
CPC .......... *A61K 31/517* (2013.01); *A61K 31/4196* (2013.01); *A61K 31/675* (2013.01)

(58) Field of Classification Search
USPC ................................................. 514/383, 384
See application file for complete search history.

(56) References Cited

U.S. PATENT DOCUMENTS

| | | | |
|---|---|---|---|
| 2,898,343 A | 8/1959 | Klingsberg |
| 3,189,614 A | 6/1965 | Pesson |
| 3,714,231 A | 1/1973 | Kolling et al. |
| 3,898,272 A | 8/1975 | Kurz et al. |
| 4,178,253 A | 12/1979 | Lee et al. |
| 4,269,846 A | 5/1981 | Huang et al. |
| 4,624,995 A | 11/1986 | Katritzky et al. |
| 4,740,568 A | 4/1988 | Katritzky et al. |
| 4,931,084 A | 6/1990 | Findeisen et al. |
| 5,006,650 A | 4/1991 | Barbachyn |
| 5,219,722 A | 6/1993 | Tanaka et al. |
| 5,298,520 A | 3/1994 | Baker et al. |
| 5,371,101 A | 12/1994 | Itoh et al. |
| 5,395,818 A | 3/1995 | Haas et al. |
| 5,436,252 A | 7/1995 | Sorensen et al. |
| 5,464,810 A | 11/1995 | Haas et al. |
| 5,466,820 A | 11/1995 | Itoh et al. |
| 5,476,946 A | 12/1995 | Linker et al. |
| 5,478,827 A | 12/1995 | Oku et al. |
| 5,489,598 A | 2/1996 | Connor et al. |
| 5,510,362 A | 4/1996 | Matassa et al. |
| 5,532,378 A | 7/1996 | Daum et al. |
| 5,538,988 A | 7/1996 | Martinez et al. |

(Continued)

FOREIGN PATENT DOCUMENTS

| | | |
|---|---|---|
| AU | 2012200157 A1 | 2/2012 |
| DE | 10 01 992 B | 2/1957 |

(Continued)

OTHER PUBLICATIONS

Rice, J.W., et al. Oncology Research vol. 18, pp. 229-242. Published 2009.*

(Continued)

*Primary Examiner* — Paul Zarek
*Assistant Examiner* — George W Kosturko
(74) *Attorney, Agent, or Firm* — McCarter & English, LLP; Steven G. Davis

(57) ABSTRACT

A pharmaceutical combination comprising an EGFR inhibitor and an Hsp90 inhibitor according to the following formulae (I) or (Ia) a tautomer, or a pharmaceutically acceptable salt thereof, wherein the variables in the structural formulae are defined herein. Also provided are methods for treating a proliferative disorder in a subject in need thereof using pharmaceutical combinations disclosed herein.

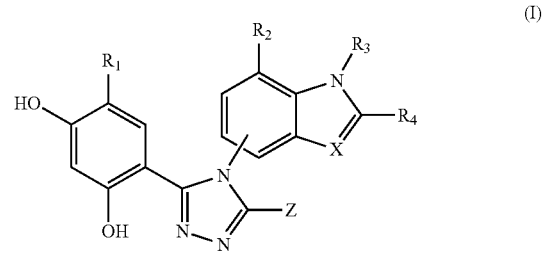

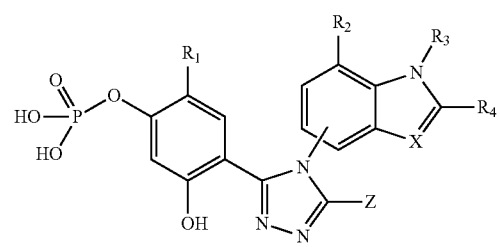

3 Claims, 3 Drawing Sheets

(56) References Cited

U.S. PATENT DOCUMENTS

| | | |
|---|---|---|
| 5,552,369 A | 9/1996 | Findeisen et al. |
| 5,624,931 A | 4/1997 | Oku et al. |
| 5,625,074 A | 4/1997 | Daum et al. |
| 5,654,438 A | 8/1997 | Findeisen et al. |
| 5,663,362 A | 9/1997 | Haas et al. |
| 5,861,358 A | 1/1999 | Findeisen et al. |
| 5,869,509 A | 2/1999 | Romine et al. |
| 5,888,694 A | 3/1999 | Yamada et al. |
| 5,952,502 A | 9/1999 | McCullough et al. |
| 5,968,921 A | 10/1999 | Gold |
| 5,972,844 A | 10/1999 | Muller et al. |
| 6,077,861 A | 6/2000 | Romine et al. |
| 6,080,772 A | 6/2000 | Tang et al. |
| 6,180,567 B1 | 1/2001 | Muller et al. |
| 6,194,090 B1 | 2/2001 | Okada |
| 6,200,931 B1 | 3/2001 | Muller et al. |
| 6,200,934 B1 | 3/2001 | Muller et al. |
| 6,251,831 B1 | 6/2001 | Muller et al. |
| 6,258,957 B1 | 7/2001 | Linker et al. |
| 6,271,249 B1 | 8/2001 | Romine et al. |
| 6,337,342 B1 | 1/2002 | Karabelas et al. |
| 6,492,406 B1 | 12/2002 | Karabelas et al. |
| 6,492,409 B1 | 12/2002 | Karabelas et al. |
| 6,583,090 B1 | 6/2003 | Gewehr et al. |
| 6,660,286 B1 | 12/2003 | Lambert et al. |
| 6,677,277 B1 | 1/2004 | Schallner et al. |
| 6,747,055 B1 | 6/2004 | Ho et al. |
| 6,855,705 B1 | 2/2005 | Tian et al. |
| 6,858,598 B1 | 2/2005 | McKearn et al. |
| 6,921,763 B2 | 7/2005 | Hirst et al. |
| 6,946,456 B2 | 9/2005 | Rosen et al. |
| 7,081,466 B2 | 7/2006 | Koya et al. |
| 7,247,734 B2 | 7/2007 | Drysdale et al. |
| 7,473,784 B2 | 1/2009 | Liu et al. |
| 7,608,635 B2 | 10/2009 | Ying et al. |
| 7,662,813 B2 | 2/2010 | Ying et al. |
| 7,825,148 B2 | 11/2010 | Ying et al. |
| 8,034,834 B2 * | 10/2011 | Du et al. ............ 514/383 |
| 8,053,456 B2 | 11/2011 | Sun et al. |
| 8,063,083 B2 | 11/2011 | Foley |
| 8,106,083 B2 | 1/2012 | Burlison et al. |
| 8,183,384 B2 | 5/2012 | Chimmanamada et al. |
| 8,188,075 B2 | 5/2012 | Ying et al. |
| 8,299,107 B2 | 10/2012 | Chimmanamada et al. |
| 8,318,790 B2 | 11/2012 | Ying et al. |
| 8,329,736 B2 | 12/2012 | Chimmanamada et al. |
| 8,329,899 B2 | 12/2012 | Ying et al. |
| 8,362,055 B2 | 1/2013 | Ying et al. |
| 8,415,377 B2 | 4/2013 | Sun et al. |
| 8,450,500 B2 | 5/2013 | Chimmanamada et al. |
| 8,486,932 B2 | 7/2013 | Burlison et al. |
| 8,524,712 B2 | 9/2013 | Lee et al. |
| 8,628,752 B2 | 1/2014 | Zhou et al. |
| 8,629,285 B2 | 1/2014 | Ying et al. |
| 8,648,071 B2 | 2/2014 | Burlison et al. |
| 8,648,104 B2 | 2/2014 | Du et al. |
| 8,742,133 B2 | 6/2014 | Ying et al. |
| 8,748,424 B2 | 6/2014 | Chimmanamada et al. |
| 8,785,658 B2 | 7/2014 | Chimmanamada et al. |
| 8,835,464 B2 | 9/2014 | Sun et al. |
| 8,901,308 B2 | 12/2014 | Ying et al. |
| 8,906,885 B2 | 12/2014 | El-Hariry et al. |
| 8,921,407 B2 | 12/2014 | Ying et al. |
| 8,927,548 B2 | 1/2015 | Ying et al. |
| 8,937,094 B2 | 1/2015 | Burlison et al. |
| 8,969,396 B2 | 3/2015 | Du et al. |
| 8,993,608 B2 | 3/2015 | Du et al. |
| 9,006,277 B2 | 4/2015 | Sun et al. |
| 2003/0054996 A1 | 3/2003 | Nicchitta et al. |
| 2003/0092749 A1 | 5/2003 | Dombroski et al. |
| 2003/0134886 A1 | 7/2003 | Karabelas et al. |
| 2003/0216369 A1 | 11/2003 | Rosen et al. |
| 2003/0216385 A1 | 11/2003 | Tobe et al. |
| 2004/0082498 A1 | 4/2004 | Strehlow |
| 2004/0106604 A1 | 6/2004 | Beight et al. |
| 2004/0110662 A1 | 6/2004 | Rosen et al. |
| 2004/0110684 A1 | 6/2004 | Balligand et al. |
| 2004/0204426 A1 | 10/2004 | Kubo et al. |
| 2004/0214818 A1 | 10/2004 | Tobe et al. |
| 2004/0235813 A1 | 11/2004 | Wanker et al. |
| 2004/0266746 A1 | 12/2004 | Rosen et al. |
| 2005/0019918 A1 | 1/2005 | Sumimoto et al. |
| 2005/0020534 A1 | 1/2005 | Johnson et al. |
| 2005/0020556 A1 | 1/2005 | Johnson et al. |
| 2005/0020557 A1 | 1/2005 | Johnson et al. |
| 2005/0020558 A1 | 1/2005 | Johnson et al. |
| 2005/0026893 A1 | 2/2005 | Johnson et al. |
| 2005/0048533 A1 | 3/2005 | Sidransky et al. |
| 2005/0054589 A1 | 3/2005 | Johnson et al. |
| 2005/0054625 A1 | 3/2005 | Johnson et al. |
| 2005/0058956 A1 | 3/2005 | Watanabe et al. |
| 2005/0154039 A1 | 7/2005 | Glacera Contour et al. |
| 2005/0267087 A1 | 12/2005 | Poulaki et al. |
| 2005/0267185 A1 | 12/2005 | Marino et al. |
| 2005/0272083 A1 | 12/2005 | Seshagiri |
| 2005/0288347 A1 | 12/2005 | Hodge et al. |
| 2006/0135594 A1 | 6/2006 | Fraley et al. |
| 2006/0167070 A1 * | 7/2006 | Ying et al. ............ 514/383 |
| 2006/0211737 A1 | 9/2006 | Huang et al. |
| 2006/0235058 A1 | 10/2006 | Cheung et al. |
| 2007/0066831 A1 | 3/2007 | MacDonald et al. |
| 2007/0087998 A1 | 4/2007 | Ying et al. |
| 2007/0203194 A1 | 8/2007 | Zelle et al. |
| 2007/0238699 A1 | 10/2007 | Demko et al. |
| 2008/0004266 A1 * | 1/2008 | Du et al. ............ 514/230.5 |
| 2008/0027047 A1 | 1/2008 | Ying |
| 2008/0125587 A1 | 5/2008 | Chimmanamada et al. |
| 2008/0182857 A1 | 7/2008 | Eggenweiler et al. |
| 2008/0269218 A1 | 10/2008 | Kuramochi et al. |
| 2008/0318241 A1 | 12/2008 | Dang et al. |
| 2009/0131529 A1 | 5/2009 | Sherman et al. |
| 2009/0232906 A1 | 9/2009 | Hausheer |
| 2010/0069442 A1 | 3/2010 | Ying et al. |
| 2010/0203043 A1 | 8/2010 | Ree et al. |
| 2010/0209929 A1 | 8/2010 | Fantl et al. |
| 2010/0249185 A1 | 9/2010 | Du et al. |
| 2010/0273846 A1 | 10/2010 | Du et al. |
| 2010/0280032 A1 | 11/2010 | Zhou et al. |
| 2010/0298331 A1 | 11/2010 | Lee et al. |
| 2011/0009397 A1 | 1/2011 | Ying et al. |
| 2011/0046125 A1 | 2/2011 | Ying |
| 2011/0118298 A1 | 5/2011 | Fritz et al. |
| 2011/0144103 A1 | 6/2011 | Chimmanamada et al. |
| 2011/0152310 A1 | 6/2011 | Burlison et al. |
| 2011/0195094 A1 | 8/2011 | Ying et al. |
| 2011/0224206 A1 | 9/2011 | Ying et al. |
| 2011/0301212 A1 | 12/2011 | Du et al. |
| 2011/0319404 A1 | 12/2011 | Foley |
| 2011/0319447 A1 | 12/2011 | Sun et al. |
| 2012/0046288 A1 | 2/2012 | Burlison et al. |
| 2012/0064175 A1 | 3/2012 | Vukovic et al. |
| 2012/0101072 A1 | 4/2012 | Burlison et al. |
| 2012/0122869 A1 | 5/2012 | Ying et al. |
| 2012/0245186 A1 | 9/2012 | Blackman et al. |
| 2012/0330009 A1 | 12/2012 | Ying et al. |
| 2013/0072461 A1 | 3/2013 | Chimmanamada et al. |
| 2013/0150385 A1 | 6/2013 | Blackman et al. |
| 2013/0156755 A1 | 6/2013 | Blackman et al. |
| 2013/0171105 A1 | 7/2013 | Blackman et al. |
| 2013/0172333 A1 | 7/2013 | Jain et al. |
| 2013/0225870 A1 | 8/2013 | Lee et al. |
| 2013/0331357 A1 | 12/2013 | Proia et al. |
| 2013/0338155 A1 | 12/2013 | Ying |
| 2013/0345219 A1 | 12/2013 | Lee et al. |
| 2014/0004516 A1 | 1/2014 | Sattler et al. |
| 2014/0005145 A1 | 1/2014 | Proia |
| 2014/0024030 A1 | 1/2014 | Blackman et al. |
| 2014/0045908 A1 | 2/2014 | Blackman et al. |
| 2014/0051664 A1 | 2/2014 | Foley et al. |
| 2014/0051665 A1 | 2/2014 | Proia et al. |
| 2014/0094436 A1 | 4/2014 | Ying et al. |
| 2014/0127740 A1 | 5/2014 | Zhou et al. |
| 2014/0135370 A1 | 5/2014 | Vukovic |
| 2014/0141511 A1 | 5/2014 | Zhou et al. |

(56) References Cited

U.S. PATENT DOCUMENTS

| | | | |
|---|---|---|---|
| 2014/0178366 A1 | 6/2014 | Blackman et al. |
| 2014/0194388 A1 | 7/2014 | Proia et al. |
| 2014/0221375 A1 | 8/2014 | Du et al. |
| 2014/0228418 A1 | 8/2014 | Proia et al. |
| 2014/0255348 A1 | 9/2014 | Proia |
| 2014/0256680 A1 | 9/2014 | Proia et al. |
| 2014/0286902 A1 | 9/2014 | Proia |
| 2014/0288301 A1 | 9/2014 | Chimmanamada et al. |
| 2014/0296176 A1 | 10/2014 | Proia et al. |
| 2014/0296186 A1 | 10/2014 | Ying et al. |
| 2014/0315943 A1 | 10/2014 | Proia et al. |
| 2014/0363830 A1 | 12/2014 | Ying |
| 2014/0371222 A1 | 12/2014 | Sun et al. |
| 2015/0005299 A1 | 1/2015 | Chimmanamada et al. |
| 2015/0051203 A1 | 2/2015 | Chimmanamada et al. |
| 2015/0094349 A1 | 4/2015 | Du et al. |
| 2015/0099721 A1 | 4/2015 | Acquaviva et al. |
| 2015/0119395 A1 | 4/2015 | Chimmanamada et al. |
| 2015/0126499 A1 | 5/2015 | Burlison et al. |

FOREIGN PATENT DOCUMENTS

| | | |
|---|---|---|
| DE | 10 2005 007304 A1 | 8/2006 |
| EP | 1 857 446 A1 | 11/2007 |
| EP | 2025347 A1 | 2/2009 |
| EP | 2133094 A1 | 12/2009 |
| FR | 2546887 A1 | 12/1984 |
| JP | 57070820 A | 5/1982 |
| JP | 59010574 A | 1/1984 |
| JP | 2000284412 A | 10/2000 |
| JP | 2003114488 A | 4/2003 |
| WO | WO-96/22985 A1 | 8/1996 |
| WO | WO-97/03067 A1 | 1/1997 |
| WO | WO-98/04135 A1 | 2/1998 |
| WO | WO-98/27092 A1 | 6/1998 |
| WO | WO-00/71537 A1 | 11/2000 |
| WO | WO-00/78750 A1 | 12/2000 |
| WO | WO-02/06213 A2 | 1/2002 |
| WO | WO-02/036171 A1 | 5/2002 |
| WO | WO-02/066447 A1 | 8/2002 |
| WO | WO-02/069900 A2 | 9/2002 |
| WO | WO-02/072576 A1 | 9/2002 |
| WO | WO-02/094833 A1 | 11/2002 |
| WO | WO-03/013430 A2 | 2/2003 |
| WO | WO-03/045926 A1 | 6/2003 |
| WO | WO-03/047523 A2 | 6/2003 |
| WO | WO-03/050295 A2 | 6/2003 |
| WO | WO-03/055860 A1 | 7/2003 |
| WO | WO-03/077914 A1 | 9/2003 |
| WO | WO-03/082266 A1 | 10/2003 |
| WO | WO-03/089006 A1 | 10/2003 |
| WO | WO-2004/045617 A1 | 6/2004 |
| WO | WO-2004/050087 A1 | 6/2004 |
| WO | WO-2004/056782 A1 | 7/2004 |
| WO | WO-2004/072051 A1 | 8/2004 |
| WO | WO-2004/081037 A1 | 9/2004 |
| WO | WO-2004/082676 A1 | 9/2004 |
| WO | WO-2004/089367 A1 | 10/2004 |
| WO | WO-2004/089415 A2 | 10/2004 |
| WO | WO-2004/089416 A2 | 10/2004 |
| WO | WO-2004/094819 A1 | 11/2004 |
| WO | WO-2004/096212 A1 | 11/2004 |
| WO | WO-2004/096781 A1 | 11/2004 |
| WO | WO-2005/000300 A1 | 1/2005 |
| WO | WO-2005/016920 A1 | 2/2005 |
| WO | WO-2005/027972 A2 | 3/2005 |
| WO | WO-2005/033102 A2 | 4/2005 |
| WO | WO-2005/039569 A1 | 5/2005 |
| WO | WO-2005/040345 A1 | 5/2005 |
| WO | WO-2005/041879 A2 | 5/2005 |
| WO | WO-2005/044194 A2 | 5/2005 |
| WO | WO-2005/087750 A1 | 9/2005 |
| WO | WO-2005/097758 A1 | 10/2005 |
| WO | WO-2006/018082 A1 | 2/2006 |
| WO | WO-2006/039977 A1 | 4/2006 |
| WO | WO-2006/047631 A2 | 5/2006 |
| WO | WO-2006/061712 A2 | 6/2006 |
| WO | WO-2006/087077 A2 | 8/2006 |
| WO | WO-2006/091246 A1 | 8/2006 |
| WO | WO-2006/095783 A1 | 9/2006 |
| WO | WO-2006/101052 A1 | 9/2006 |
| WO | WO-2007/111904 A2 | 10/2007 |
| WO | WO-2007/134678 A2 | 11/2007 |
| WO | WO-2008/086857 A1 | 7/2008 |
| WO | WO-2008/108386 A1 | 9/2008 |
| WO | WO-2008/156573 A1 | 12/2008 |
| WO | 2009023211 A1 | 2/2009 |
| WO | WO-2009/099649 A1 | 8/2009 |
| WO | WO-2009/102446 A2 | 8/2009 |
| WO | WO-2010/020618 A1 | 2/2010 |
| WO | WO-2010/060937 A2 | 6/2010 |
| WO | WO-2010/138377 A1 | 12/2010 |
| WO | WO-2011/060328 A1 | 5/2011 |

OTHER PUBLICATIONS

Rice, J.W. et al., Oncology Research vol. 18, pp. 229-242. Published 2009.*

Shepherd, F.A. et al., New England Journal of Medicine vol. 353, pp. 123-132. Published 2005.*

Goldman, L. et al., Cecil's Textbook of Medicine 21st edition. Published (2000).*

Calabresi and Chabner (Goodman & Gilman's The Pharmacological Basis of Therapeutics, 10th ed, 2001).*

Berenbaum ("Synergy, additivism and antagonism in immunosuppression", Clin. Exp Immunol. vol. 28, pp. 1-18, Published 1977).*

Rice, J.W., et al., Oncology Research vol. 18, pp. 229-242. Published 2008.*

Rice, J.W., et al. Oncology Research vol. 18, pp. 229-242. Published 2008.*

Blackman Ronald K et al: "Hsp90 inhibitor STA-9090 enhances the activity of standard of care therapies in erlotinib-sensitive and -resistant NSCLC models". Proceedings of the Annual Meeting of the American Association for Cancer Research. vol. 51. Apr. 19, 2010. Page 640.

Edwards A. et al, "Effect of the histone deacetylase inhibitor LBH589 against epidermal growth factor receptor-dependent human lung cancer cells", Molecular Cancer Therapeutics 20070901 US Lnkd-DOI: 10.1158/1535-7163. MCT-006-0761, vol. 6, No. 9, Sep. 1, 2007, pp. 2515-2524.

International Search Report and Written Opinion for PCT/US2011/033008 dated Jun. 30, 2011.

Johnson J. R. et al.: "Approval summary for erlotinib for treatment of patients with locally advanced or metastatic non-small cell lung cancer after failure of at least one prior chemotherapy regimen", Clinical Cancer Research 20050915 US Lnkd-DOI: 10.1158/1078-0432.CCR-05-0790, vol. 11, No. 18, Sep. 15, 2005, pp. 6414-6421.

Pashtan I. et al.: "Targeting Hsp90 prevents escape of breast cancer cells from tyrosine kinase inhibition", Cell Cycle 20080915 US, vol. 7, No. 18, Sep. 15, 2008, pp. 2936-2941.

Premkumar Daniel R. et al.: "Cooperative inhibitory effect of ZD1839 (Iressa) in combination with 17-AAG on glioma cell growth", Molecular Carcinogenesis, vol. 45, No. 5, May 2006, pp. 288-301.

Rice J.W. et al.: "Targeting of multiple signaling pathways by the Hsp90 inhibitor SNX-2112 in EGFR resistance models as a single agent or in combination with erlotinib", Oncology Research 2009 Cognizant Communication Corporation USA Lnkd-DOI: 10.3727/096504009X12596189659240, vol. 18, No. 5-6, 2006, pp. 229-242, XP009148484.

Synta Press Release: Synta Pharmaceuticals Announces Ganetespib (STA-9090) Non-small Cell Lung Cancer Phase 2 Interim Results to be Presented at the Upcoming IASLC 11th Annual Targeted Therapies for the Treatment of Lung Cancer Meeting, Jan. 27, 2011.

Synta Press Release: Synta Announces Phase 2b/3 Trial for Ganetespib (STA-9090) in Advanced 2nd-line Non-small Cell Lung Cancer, Feb. 26, 2011.

(56) References Cited

OTHER PUBLICATIONS

Synta Press Release: Synta Announces Encouraging Preliminary Results for Ganetespib (STA-9090) in Phase 2 Nonsmall Cell Lung Cancer Trial, Feb. 26, 2011.
Synta Press Release: Synta to Host Investigator Panel Session on New Clinical Opportunities for Hsp90 Inhibition in Oncology, Mar. 21, 2011.
Synta Press Release: Synta Announces Ganetespib Results at AACR—Inhibition of Multiple Oncogenes and Resistance Mechanisms Leads to Potent Activity in NSCLC and Strong Enhancement of Radiation Therapy, Apr. 4, 2011.
Synta Press Release: Synta Announces Ganetespib Clinical Data Presentations at the 2011 American Society for Clinical Oncology (ASCO) Annual Meeting, May 18, 2011.
Synta Press Release: Synta Announces Publication of Results Showing Ganetespib (STA-9090) Exhibits Potent Activity in Models of Cancer with Activated JAK/STAT Signaling, May 26, 2011.
Synta Press Release: Synta Announces Ganetespib Phase 2 Non-small Cell Lung Cancer Trial Results Show Encouraging Single Agent Clinical Activity, Jun. 4, 2011.
Synta Press Release: Synta Announces Presentation of Additional Ganetespib Results at ASCO, Jun. 6, 2011.
Synta Press Release: Synta Announces Presentation of Ganetespib Phase 2 Non-small Cell Lung Cancer Trial Results at IASLC 14th World Conference on Lung Cancer, Jul. 7, 2011.
Synta Press Release: Synta Announces First Patient Treated in the GALAXY Trial™ a Phase 2b/3 Trial for Ganetespib in Advanced 2nd-line Non-small Cell Lung Cancer, Jul. 20, 2011.
Synta Press Release: Synta Announces Presentation of Results of Ganetespib Study in Combination with Docetaxel in Solid Tumors, Sep. 26, 2011.
Synta Press Release: Synta Announces Results Show Ganetespib Sensitizes Rectal Cancer Cells to Chemoradiotherapy, Nov. 10, 2011.
Synta Press Release: Synta Presents Results on Ganetespib and Hsp90 Inhibitor Class at the AACR-EORTC-NCI Molecular Targets and Cancer Therapeutics Conference, Nov. 15, 2011.
Synta Press Release: Synta Announces Publication of Ganetespib Results in Molecular Cancer Therapeutics, Dec. 6, 2011.
Synta Press Release: Ganetespib Shows Clinical Activity in HER2+ and Triple Negative Metastatic Breast Cancer, Dec. 8, 2011.
Synta Press Release: Ganetespib Potently Inhibits Multiple Signaling Pathways Active in Breast Cancer, Dec. 12, 2011.
Synta Press Release: Ganetespib Showed Activity in KRAS-Mutant NSCLC as Monotherapy and in Combinations, Jan. 10, 2012.
Synta Press Release: Synta Announces Publication of Results Showing Ganetespib Synergizes with Taxanes in Multiple Non-small Cell Lung Cancer Models, Jan. 16, 2012.
Synta Press Release: Synta Announces Review of Ganetespib Results in Lung Cancer Presented at IASLC 12th Annual Targeted Therapies for the Treatment of Lung Cancer Meeting, Feb. 29, 2012.
Synta Press Release: Synta Announces Results on Ganetespib Across a Range of Malignancies at the American Association for Cancer Research (AACR) Annual Meeting, Apr. 4, 2012.
Synta Press Release: Multiple Myeloma Research Consortium (MMRC) and Synta Pharmaceuticals Announce Initiation of Ganetespib Clinical Trial in Multiple Myeloma, Apr. 10, 2012.
Synta Press Release: Synta Announces Results Demonstrating Potent Ganetespib Activity across Broad Range of Crizotinib-Resistant Alk+ NSCLC models at the European Lung Cancer Conference, Apr. 18, 2012.
Synta Press Release: Synta Announces Ganetespib Presentations at the Annual Meeting of the American Society for Clinical Oncology, Jun. 4, 2012.
Synta Press Release: Synta Announces Results from Interim Analysis of the Randomized Phase 2b/3 GALAXY Trial Evaluating Ganetespib plus Docetaxel in Second-Line Non-Small Cell Lung Cancer, Jun. 27, 2012.
Synta Press Release: Updated Results from Phase 2b/3 GALAXY Trial Show Promising Improvement in Survival from the Addition of Ganetespib to Docetaxel in Second-Line Non-Small Cell Lung Cancer, Sep. 29, 2012.
Synta Press Release: Synta Announces First Patients Treated in Pivotal GALAXY-2 Trial Evaluating Ganetespib in Advanced Non-Small Cell Lung Cancer, Apr. 22, 2013.
Synta Press Release: Synta Announces Positive Overall Survival Results From GALAXY-1 Phase 2b/3 Trial of Ganetespib in Second-Line Non-Small Cell Lung Cancer, Jun. 3, 2013.
Synta Press Release: Synta Announces Publication of Clinical and Non-Clinical Results Demonstrating Unique Antiangiogenic Effects of Ganetespib, Jul. 17, 2013.
Synta Press Release: Synta Announces Fast Track Designation Granted for Ganetespib in Non-Small Cell Lung Adenocarcinoma, Sep. 12, 2013.
Synta Press Release: Synta Announces Presentation of Ganetespib Results at the 2013 European Cancer Congress, Sep. 28, 2013.
Synta Press Release: Synta Announces Positive One-Year Follow-up Results for the GALAXY-1 Trial of Ganetespib in NSCLC at the 2013 World Conference on Lung Cancer, Oct. 26, 2013.
Synta Press Release: Synta Announces Publications Demonstrating Ganetespib Activity in Triple-Negative Breast Cancer Models, Nov. 21, 2013.
Synta Press Release: Synta Announces Positive Interim Results from the ENCHANT-1 Trial of Ganetespib in Metastatic Breast Cancer at the 2013 San Antonio Breast Cancer Symposium, Dec. 12, 2013.
Synta Press Release: Synta Announces Launch of GANNET53, a Randomized, pan-European Study of Ganetespib in p53 Mutant, Metastatic Ovarian Cancer, Jan. 9, 2014.
Synta Press Release: Synta Announces Initiation of Three Multicenter, Randomized Phase II/III Trials of Ganetespib in Acute Myeloid Leukemia (AML) and High Risk Myelodysplastic Syndrome (MDS), Jan. 9, 2014.
Synta Press Release: Synta and QuantumLeap Healthcare Collaborative Announce Selection of Ganetespib for I-SPY 2 Trial in Breast Cancer, Mar. 11, 2014.
Synta Press Release: Synta Announces Positive Interim Results from the ENCHANT-1 Trial of Ganetespib in Metastatic Breast Cancer at the 9th European Breast Cancer Conference, Mar. 20, 2014.
Synta Press Release: Synta Announces Results From Final Analysis of the GALAXY-1 Trial of Ganetespib in NSCLC, May 8, 2014.
Synta Press Release: Synta Announces Advancement of Ganetespib into Phase 3 Extension of AML LI-1 Study for Patients with AML and High-Risk MDS, Jul. 21, 2014.
Synta Press Release: Synta Announces Initiation of I-SPY 2 Trial of Ganetespib in Breast Cancer, Oct. 29, 2014.
Synta Press Release: Synta Announces FDA's Oncologic Drugs Advisory Committee to Discuss Pediatric Uses for Ganetespib, Nov. 5, 2014.
Synta Press Release: Synta Announces Presentation of Results from an Investigator-Sponsored Phase 1 Trial of Ganetespib in HER2+ Metastatic Breast Cancer at the 2014 San Antonio Breast Cancer Symposium, Dec. 12, 2014.
Abdel-Fattah, et al., "1-Azido-4-phenyl-1,4-butanedione as a Convenient Precursor for the Synthesis of Various Nitrogen Heterocycles," *Egyptian J. Of Chemistry*, 46(1), 153-162 (2003).
Abdel-Hamid, Hoda A., et al., "Synthesis of some biologically active heterocycles. Reactions of the hydrazide of 2'-thienoylanthranilic acid and its 3,5-dibromo derivative," Phosphorus, Sulfur and Silicon and the Related Elements (1992), 72(1-4):237-247.
Abramson et al., "The heat shock protein 90 inhibitor IPI-504 induces apoptosis of AKT-dependent diffuse large B-cell lymphomas", British Journal of Haematology, vol. 144, No. 3, pp. 358-366 (2009).
Acquaviva et al, "FGFR3 Translocations in Bladder Cancer: Differential Sensitivity to HSP90 Inhibition Based on Drug Metabolism", Mol Cancer Res, 12:1042-1054 (2014).
Acquaviva et al, "mTOR Inhibition Potentiates HSP90 Inhibitor Activity via Cessation of HSP Synthesis", Mol Cancer Res, 12:703-713 (2014).
Acquaviva et al, "Overcoming acquired resistance to BRAF inhibitors in melanoma with the HSP90 inhibitor ganetespib", Poster,

(56) References Cited

OTHER PUBLICATIONS

103rd Annual Meeting American Association for Cancer Research (AACR), Mar. 31- Apr. 4, 2012—Chicago, IL.
Acquaviva et al, "Potent Anticancer Actions of the Hsp90 Inhibitor Ganetespib (STA-9090) in Wild-Type EGFR Models of Lung Cancer", Poster, Apr. 4, 2011—Orlando, FL.
Acquaviva et al, "Targeting KRAS mutant NSCLC with the Hsp90 inhibitor ganetespib", Poster, AACR-IASLC Joint Conference on Molecular Origins of Lung Cancer: Biology, Therapy, and Personalized Medicine, Jan. 10, 2012—San Diego, CA.
Acquaviva et al, "The Hsp90 inhibitor ganetespib promotes the degradation of FGFR3 in bladder cancer models and induces regression in tumors harboring oncogenic FGFR3 fusions", Poster, AACR/NCI/EORTC Molecular Targets and Cancer Therapeutics, Oct. 19-23, 2013—Boston, MA.
Acquaviva et al,"Overcoming Acquired BRAF Inhibitor Resistance in Melanoma via Targeted Inhibition of Hsp90 with Ganetespib", Mol Cancer Ther, 13:353-363 (2014).
Acquaviva et al,"Targeting KRAS-Mutant Non-Small Cell Lung Cancer with the Hsp90 Inhibitor Ganetespib", Mol Cancer Ther, 11:2633-2643 (2012).
Al-Saadi, et al., "In Vitro Antitumor Screening of Some Polysubstituted Pyrazole Analogs", Saudi Pharmaceutical Journal, Saudi Pharmaceutical Society, Riyad, SA, 2005, vol. 13, pp. 89-96.
Anderson et al., "CCT241533 Is a Potent and Selective Inhibitor of CHK2 that Potentiates the Cytoxicity of PARP Inhibitors" Cancer Research, vol. 71(2): 463-472, Jan. 15, 2011.
Andotra, C.S., et al., "Synthesis and Biocidal Activity of N-Phenyl-2,6-Substituted Aryl-5-Thione-1, 2, 4-Triazolo[1, 5-a]-s-Triazine-7-Ones," Indian Journal of Heterocyclic Chemistry, 5:237-238 (1996).
Anonymous: "Sample name: NCI-H1975 (Cosmic ID: 924244)", Catalogue of Somatic Mutations in Cancer (COSMIC), Sep. 18, 2006, XP002658470, Retrieved from the Internet: URL:http://www.sanger.ac.uk/perl/genetics/CGP/core_line_viewer?action=sample&name=NCI-H1975; decor=printable [retrieved on Sep. 7, 2011].
Arkenau H-T, et al., Targeting BRAF for Patients with Melanoma, British Journal of Cancer, 104(3):392-398, Feb. 2011.
Awada et al, "ENCHANT-1 Trial (NCT01677455): An Open-Label Multicenter Phase 2 Window-of-Opportunity Study Evaluating Ganetespib in Women With First-Line Metastatic Breast Cancer", Poster, The 2013 American Society of Clinical Oncology (ASCO) Annual Meeting, May 31-Jun. 4, 2013—Chicago, IL.
Awada et al, "The ENCHANT-1 Trial (NCT01677455): An Open-Label Multicenter Phase 2 Proof of Concept Study Evaluating First-Line Ganetespib Monotherapy in Women With Metastatic HER2-Positive or Triple-Negative Breast Cancer (TNBC)", Poster, San Antonio Breast Cancer Symposium, Dec. 10-14, 2013—San Antonio, TX.
Ayca, E. et al., "Mass Spectra of Some 3,4-Disubstituted- 2-1,2,4-Triazolin-5-Ones," Chimica Acta Turcica, 11: 285-289 (1983).
Ayca, E. et al., "Preparation of 3-Alkyl(aryl)-4-Aryl-42-1,2,4-Triazolin-5-Ones," Chimica Acta Turcica, 9: 99-108(1981).
Bahceci, S., et al., "Reactions of 4-Amino-4,5-Dihydro-1H-1,2,4-Triazol-5-ones and 4-Amino4H-1,2,4-Triazoles with Some Carboxylic Acid Anhydrides," *Turkish Journal of Chemistry*, 22(3): 237-241 (1998).
Balmanno et al, "Intrinsic resistance to the MEK 1/2 inhibitor AZD6244 (ARRY-142886) is asociated with weak ERK1/2 signaling and/or strong PI3K signaling in colorectal cancer cell lines." Int J of Cancer 125: 2332-2341 (2009).
Banerji U, et al., An in vitro and in vivo study of the combination of the heat shock protein inhibitor 17-allylamino-17-demethoxygeldanamycin and carboplatin in human ovarian cancer models, Cancer Chemotherapy and Pharmacology, vol. 62(5) pp. 769-778 (2008).
Bansal et al, "Heat shock protein 90 regulates the expression of Wilms tumor 1 protein in myeloid leukemias", Blood, 25:4591-4599 (2010).
Bao, R., et al: "CUDE-305, a Novel Syntehic HSP90. Inhibitor with Unique Pharmacologic Properties for Cancer Therapy" Clin Cancer Res. 15: 4046-4057, 2009.

Barker, et al., "Inhibition of Hsp90 acts synergistically with topoisomerase II poisons to increase the apoptotic killing of cells due to an increase in topoisomerase II mediated DNA damage," Nucleic Acids Res. 2006; 34(4):1148-57.
Barril, X., et aL, "Structure-Based Discovery of a New Class of Hsp90 Inhibitors," *Biorganic & Medicinal Chemistry Letters*, 2005, 15, pp. 5187-5191.
Beger et. al., World Journal of Surgery, 2003, Societe Internationale de Chirurgie, vol. 27, pp. 1075-1084.
Beilstein Registry No. 4329746; 4 pp (2010).
Beilstein Registry No. 4562121; 2 pp (2010).
Beilstein Registry No. 546443; 2 pp (2012).
Beilstein Registry No. 551485; 2 pp (2010).
Beilstein Registry No. 567249; 1 pg (2010).
Beilstein Registry No. 574001, 5-26-09-00436, XP-002372386 (2005).
Beilstein Registry No. 6162150; 2 pp (2010).
Beilstein Registry No. 625992, 5-26-03-00436, XP-002372385 (2005).
Beilstein Registry No. 6742740; 2 pp (2010).
Bergethon K. et al., "ROS1 rearrangements define a unique molecular class of lung cancers", Journal of Clinical Oncology, American Society of Clinical Oncology, US, vol. 30, No. 8, pp. 863-870, 2012.
Bhat, A. K., et al., "Chemotherapy of Fungus Infections: Part I—I-Acyl-4-substituted Thiosemicarbazides, 3-Aryl-4-substituted-5-mercapto-1,2,4-4H-triazoles & Related Compounds," *Indian Journal of Chemistry* 5(9):397-401 (Sep. 1967).
Bischt et al., "Geldanamycin and 17-Allylamino-17-demethoxygeldanamycin Potentiate the in Vitro and in Vivo Radiation Response of Cervical Tumor Cells via the Heat Shock Protein 90-Mediated Intracellular Signaling and Cytotoxicity", Cancer Res, 63:8984-8995 (2003).
Blackman et al, "Hsp90 Inhibitor STA-9090 Enhances the Activity of Standard of Care Therapies in Erlotinib-Sensitive and -Resistant NSCLC Models", 101st AACR Annual Meeting, Apr. 19, 2010—Washington, DC.
Blasina et al., " Breaching the DNA damage checkpoint via PF-00477736, a novel small-molecular inhibitor of checkpoint kinase 1" Molecular Cancer Therapeutics, vol. 7(8): 2394-2404, Aug. 1, 2008.
Bognar, Rezso, et al. Magyar Kemiai Folyoirat (1974), 80(3), 114-16.
Bonvini et al., "Nucleophosmin-anaplastic lymphoma kinase (NPM-ALK), a novel Hsp90-cleint tyrosine kinase: down-regulation of NPM-ALK expression and tyrosine phosphorylation in Alk(+) CD30(+) lymphoma cells by the Hsp90 antagonist 17-allylamino, 17-demethoxygeldanamycin", Cancer Res, 62:1559-1566 (2002).
Brahmer et al, "A Phase 2 Study of the Hsp90 Inhibitor Ganetespib (STA-9090) asMonotherapy in Patients with Advanced NSCLC", Presentation, IASLC 14th World Conference on Lung Cancer, Jul. 7, 2011—Amsterdam, The Netherlands.
Brough, et al., "3-(5-chloro-2,4-dihydroxyphenyl)-pyrazole-4-carboxamides as inhibitors of the Hsp90 molecular chaperone," Bioorganic and Medicinal Chemistry Letters (2005), 15:5197-5201.
Bucci et al. "Geldanamycin, an inhibitor of heat shock protein 90 (Hsp90) mediated signal transduction has anti-inflammatory effects and interacts with glucocorticoid receptor in vivo", Br.J.Pharmacol., 2000, vol. 131, pp. 13-16.
Burger's Medicinal Chemistry 336-337 (Manfred Wolff, ed., John C Wiley & Sons, 1980).
Busacca, "Novel mechanisms of sensitivity and acquired resistance to Hsp90 inhibition by Ganetespib", Presentation, 15th World Conference on Lung Cancer, Oct. 27-30, 2013—Sydney, Australia.
Byrn et al. Solid-State Chemistry of Drugs, 2d, Chapter 11 Hydrates and Solvates, 233-247 (1999).
Caldwell et al., "Structure-Based Design of Potent and Selective 2-(Quinazolin-2-yl)phenol Inhibitors of Checkpoint Kinase 2" J. of Medicinal Chemistry, vol. 54(2): 580-590, Jan. 27, 2011.
Cameron et al, "Targeting HSP90 in breast cancer: ENCHANT-1 (NCT01677455) phase 2 proof of concept study of ganetespib in first-line treatment of women with metastatic HER2 positive or triple negative breast cancer (TNBC)", Presentation, 9th European Breast Cancer Conference, Mar. 19-21, 2014—Glasgow, Scotland.

(56) References Cited

OTHER PUBLICATIONS

Cameron et al, "The ENCHANT™ Trial: An open label multicenter phase 2 window of opportunity study evaluating ganetespib (STA-9090) monotherapy in women with previously untreated metastatic HER2 positive or triple negative breast cancer (TNBC)", ESMO 2012 Congress, Sep. 28-Oct. 2, 2012—Vienna, Austria.

Cansiz, A. et al., "Synthesis of Some New 4, 5-Substituted-4H-1, 2, 4-triazole-3-thiol Derivatives," Molecules, 9:204-212 (2004).

Cao, X, et al: "Non-invasive MRI tumor imaging and synergistic anticancer effect of HSP90 inhibitor and glycolysis inhibitor in RIP1-Tag2 transgenic pancreatic tumor model", Cancer Chemotherapy and Pharmacology, Springer, Berlin, De, vol. 62, No. 6, Feb. 6, 2008, pp. 985-994, XP019625579.

Cava, M.P. and Levinson, MJ., "Thionation Reactions of Lawesson's Reagents," *Tetrahedron Report No.* 19241(22):5061-5087 (1985).

Cesur N., and Cesur, Z., "Synthesis of Some 4-Thiazoline and 4H-1,2,4-Triazole Derivatives of Imidazo(1,2-a) Pyridine as Possible Anticonvulsants" *II Farmaco*, 49(10): 679-681 (1984).

Chabner et. al., Nature Reviews Cancer, 2005, Nature Publishing Group, vol. 5, pp. 65-72.

Chaloupka, Stanislav, et ai., "Reactions of3-dirnethylamino-2, 2-dirnethyl-2H-azirine with Benzoic Acid Hydrazides," Chimia, Chemical Abstracts Service, Database CA [oneline], 32(9):332-333 (1978).

Chapman, Paul B., et al., Improved Survival with Vemurafenib in Melanoma with BRAF V600E Mutation, New England Journal of Medicine, 364(26):2507-2516, Jun. 30, 2011.

Cherkasov, R.A., et al., "Organothiophosphorus Reagents in Organic Synthesis," Tetrahedron Report No. 18641(13):2567-2624 (1985).

Cheung, K.M.J., etal. "The identification, synthesis, protein crystal structure and in vitro biochemical evaluation of a new 3,4-diarylpyrazole class of Hsp90 inhibitors," *Bioorganic & Medicinal Chemistry Letter*, 15: 3338-3343 (2005).

Cho et al, "A phase I dose-escalation study of the Hsp90 inhibitor ganetespib administered twice weekly in patients with solid tumors: updated report", Poster, the 2011 American Society of Clinical Oncology (ASCO) Annual Meeting Jun. 3-7, 2011.

Ciugureanu et al., "Study of the biological acitivity of some new thiosemicarbazides and their derivatives with triazole and thiadiazole nucleus. II. Testing of antifungal acitivity", Farmacia, 1982, vol. 30, pp. 49-56.

Ciugureanu, C., and Ungureanu, M., "Synthesis of Novel 1,2,4-Triazoles and 1,3,4- Thiadiazoles Derivatives of 1,3-Benzoxazole," *Analele Stiintifice Ale Universitatii*, 5:151-158 (1997).

Ciugureanu, C., et al., "Studial activiatii biologice a unor noi tiosemicarbazide si a derivatilor acestora cu nucleu triazolic si tiadiazolic. IV. Testarea Activitatii citostatice," Farmacia, XXX(2): 101-110 (1982).

Ciugureanu, C., et al., "Studial Activitatii biologice a unor noi tiosemicarbazide si a derivatilor acestora cu nucleu triazolic si tiadiazolic III. Testarea activitatii antimicrobiene," Farmacia, XXX(1): 57-64 (1982).

Cleary et al, A phase I dose-escalation study of the Hsp90 inhibitor STA-9090 administered twice weekly in patients with solid tumors, Poster, the 2010 American Society of Clinical Oncology (ASCO) Annual Meeting, Jun. 4-8, 2010—Chicago, IL.

Coburn, M.D., et al., "Picrylamino-Substituted Heterocycles III. 1,2,4,-Triazoles (1,2)," *Journal of Heterocyclic Chemistry* 5(2): 199-203 (Apr. 1968).

Colanceska-Pagenovic, et al., "Synthesis, Antibacterial and Antifungal Activity of 4-Substituted-5-Aryl-1,2,4-Triazoles", Molecules, 2001, vol. 6, pp. 815-824.

Colgan, Stephen M. et al., "Hypoxia-induced lactate dehydrogenase expression and tumor angiogenesis", Clinical Colorectal Cancer, 6 (6), p. 442-446, 2007.

Corso et al, "Evaluating the HSP90 Inhibitor Ganetespib as a Radiosensitizing Agent in Breast Cancer Models in Vitro", Poster, The American Society for Radiation Oncology (ASTRO) 54th Annual Meeting, Oct. 28-31, 2012 - Boston, MA.

Cowen, et al., "HSP90 Potentiates the Rapid Evolution of New Traits: Drug Resistance in Diverse Fungi", Science, 2005, vol. 309, pp. 2185-2189.

Csermely P. et al, "The 90-kDa molecular chaperone family; structure, function, and clinical applications. A comprehensive review.", Pharmacology & Therapeutics, vol. 79, No. 2, pp. 129-168, 1998.

Cuzick et. al., The Lancet, 2003, vol. 361, pp. 296-300.

Davidson, J.S., "A Preparation of 3-Amino-4,5-diaryl-I ,2,4-triazoles," *Communications:359-361*(1979).

Davies et al. Bortezomib-Based Combinations in the Treatment of Non-Small Cell Lung CancerClinical Lung Cancer (2005) vol. 7, pp. S59-S63.

Demetri et al, "Phase 2 study of ganetespib (STA-9090) single agent in patients with metastatic and/or unresectable GIST", Poster, The 2011 American Society of Clinical Oncology (ASCO) Annual Meeting, Jun. 3-7, 2011.

Demetri, et al., "Overcoming Resistance to Tyrosine Kinase Inhibitors (TKIs) through Inhibition of Heat Shock Protein 90 (Hsp90) Chaperon Function in Patienets with Metastatic GIST: Results of a Phase I Trial of IPI-504, a Water-Soluble Hsp90Inhibitor", European Journal of Cancer. Supplement, Pergamon, Oxford, GB, 2006, vol. 4, p. 173, 570 Poster Abstract.

Demetri, et al., Final results from a phase III study of IPI-504 (retaspimycin hydrochloride) versus placebo in patients (pts) with gastrointestinal stromal tumors (GIST) following failure of kinase inhibitor therapies. ASCO Annual Meeting, Abstract, Jun. 4-8, 2010.

Dent et al, "Synergistic combinations of signaling pathway inhibitors: mechansims for improved cancer therapy." Drug Resistance Updates 12: 65-73 (2009).

Dias, S. et al., "VEGF.sub.165 Promotes Survival of Leukemic Cells by Hsp9O-Mediated Induction of Bcl-2 Expression and Apoptosis Inhibition," Blood, 99(7):2532-2540 (2002).

Dias, S.da R., et al., "Activated B-RAF Is an Hsp90 Client Protein That Is Targeted by the Anticancer Drug 17-Allylamino-17-Demethoxygeldanamycin," Cancer Research 65(23):10686-10691 (Dec. 1, 2005).

Diaz et al, "Ganetespib, an HSP90 Inhibitor, Sensitizes Colorectal Cancers to the Effects of Ionizing Radiation", Poster, The American Society for Radiation Oncology (ASTRO) 54th Annual Meeting, Oct. 28-31, 2012—Boston, MA.

Dogan, et al., "Synthesis and Preliminary Anticancer Activity of New 1 H-4,5-Dihydro-3-(3 Hydroxy-2-Naphthyl)-4-Substituted-1,2,4-Triazoli Ne-5-Thiones. Part Ii", Indian Journal of Chemistry, 2005, vol. 44B, pp. 2301-2307.

Dogan, et al., "Synthesis, structure elucidation and antimicrobial activity of some 3-hydroxy2-naphthoic acid hydrazide derivative", Farmaco, 1998, vol. 53, pgs. 462-467.

Doleschall et al, "A novel aldehyde synthesis based on the reduction of s-triazolo[2,3- c]quinazolin4-ium derivatives," Acta Chima Acad. Sci. Hung., 90(4):419-424 (1976).

Dote, et al., 374 Poster. Synergic antiproliferative effect of Hsp90 inhibitor in combination with cisplatin in gastric carcinoma cell lines, European Journal of Cancer Supplement, vol. 5(4) p. 77 (2007).

Dowlati, et ai, Mol Cancer Ther 2004;3:459-463.

Duran, A., et al., "Synthesis and preliminary anticancer activity of new 1,4-dihydro-3-(3- hydroxy-2-naphthyl)-4-substituted-5H-1,2,4-triazoline-5-thiones," *Farmaco*(2002), 57(7):559-564.

Dymock, B.W., et al., "Inhibitors of HSP90 and Other Chaperones for the Treatment of Cancer," *Expert Opin. Ther. Patents*, 14(6): 837-847 (2004).

Dymock, Brian W., et ai., "Novel, Potent Small-Molecule Inhibitors of the Molecular Chaperone Hsp90 Discovered Through Structure-Based Design," *J. Med. Chem.*, 2005, 48 pp. 4212-4215.

Eckstein, M., et al., "The Aminoxides of Physiologically Active Compounds," Department of Pharmaceutical Chemistry, Academy of Medicine, Cracow: 197-204, Diss. Pharm., 9 (1957).

Ei-Sharief, A.M. et al., "1, 4-Phenylenediisothiocyanate in the Synthesis of Bis-(Thiourea, Benzothiazole, Quinazoline, 1, 3-Benzoxazine and Imidazolidineiminothiones) Derivatives," Phosphorus, Sulfur, and Silicon, 179:267-275 (2004).

(56) References Cited

OTHER PUBLICATIONS

Ei-Sharief, A.M., et al., "Utility of Cyanothioformamides in Synthesis of Some Bis(Imidazole, Oxazole, Thiazole, Oxadiazole, Triazole, Benzoxazinethione and Quinazoline) Derivatives," *J. Chem. Research(S)*: 162-167 (2003).

Ei-Zahar, M.I., et al., "Synthesis of Some Novel 3-(N-Alkyl Carbamoyl) and 3-(1,2,4-Triazol-3- yl)-1,8-Naphthyridines of Anticipated Biological Activity," *Egypt. J. Chem.*, 45(2): 323-344 (2002).

Engel Jorg B et al: "Effects of lobaplatin as a single agent and in combination with Trail on the growth of triple-negative p53-mutated breast cancers in vitro.", Anti-Cancer Drugs 2012, vol. 23, No. 4, pp. 426-436.

Fennell et al, "Ultra-deep sequencing of free DNA to identify predictive, mutated HSP90 clients in the GALAXY-1 TrialTM (NCT01348126): A randomized phase IIb/III study of ganetespib (Sta-9090) in combination with docetaxel versus docetaxel alone in subjects with stage IIIb/IV NSCLC", Poster, The 2013 Annual Meeting of the American Association of Cancer Research (AACR), Apr. 6-10, 2013—Washington D.C.

Fletcher et al, "HSP90 inhibitor STA 9090 potently suppresses secondary Kit kinaseodomain mutations responsible for gastrointestinal stromal tumor (GIST) progression during imatinib therapy", Poster, AACR-NCI-EORTC Molecular Targets and Cancer Therapeutics, Nov. 17, 2009—Boston, MA.

Foley et al, "Hsp90 Inhibitor STA-9090 Induces HIF1A Degradation in the Hypoxic Regions of Solid Tumors", Poster, 101st AACR Annual Meeting, Apr. 19, 2010—Washington, DC.

Foley et al, "Synergy Between the Novel Hsp90 Inhibitor STA-9090 and Taxanes in Preclinical Models of NSCLC", Poster, AACR-IASLC Joint Conference on Molecular Origins of Lung Cancer, Jan. 12, 2010—Coronado, CA.

Foley et al: "Pharmacodynamic Analysis of the Hsp90 Inhibitor STA-9090 in a Lung Cancer Xenograft Model Supports an Infrequent Dosing Schedule in the Clinic", Poster, AACR-NCI-EORTC Molecular Targets and Cancer Therapeutics, Nov. 18, 2009—Boston, MA.

Freireich, Equivalent Surface Area Dosage Conversion Factors, https:/ /ncifrederick.cancer.gov/Lasp/ Acuc/FrederickiMedialDocuments/ ACUC42. pdf, Aug. 2007.

Friedland et al, "Beyond HER2 and Hormonal Agents: The Heat Shock Protein 90 Inhibitor Ganetespib as a Potential New Breast Cancer Therapy" Poster, 34th Annual CTRC-AACR San Antonio Breast Cancer Symposium, Dec. 8, 2011—San Antonio, TX.

Friedland et al, "Targeted inhibition of Hsp90 by ganetespib is effective across a broad spectrum of breast cancer subtypes", Invest New Drugs, 32:14-24 (2014).

Friedlander., "Treatment od Melanoma Patients with 17 AAG Results in Downregulation of the MAPK Pathway in the Melanoma Tumors" Proc. Amer. Assoc. Cancer Research, 46:(2005). AACR Meeting Abstracts Online.

G. Roue et al., "The Hsp90 inhibitor IPI-504 overcomes bortezomib resistance in mantle cell lymphoma in vitro and in vivo by downregulation of the prosurvival ER chaperone BiP/Grp78", Blood, vol. 177, No. 4, pp. 1270-1279 (2010).

Galegos Ruiz, M.I., et al; "Integration of Gene Doseage and Gene Expression in Non-Small Cell Lung Cancer Identification of HSP90 as Potential Target" PLOS ONE, 3: 2008.

Gallo, "Targeting Hsp90 to Halt Neurodegeneration", Chem.Bio., Feb. 2006, vol. 13, iss. 2, pp. 115-116.

Ganji et al, "Antiangiogenic effects of ganetespib in colorectal cancer mediated through inhibition of HIF-1a and STAT-3", Angiogenesis, 16:903-917 (2013).

Ganji et al, "Functional Inhibition of HSP90 Potentiates the Effects of Ionizing Radiation in Colorectal Cancer", Poster, 103rd Annual Meeting American Association for Cancer Research (AACR), Mar. 31-Apr. 4, 2012—Chicago, IL.

Gawande, N.G., et al., "Synthesis of Some Thiosemicarbazides and Related Compounds," *Chemistry*, 13(2): 109-111 (1987) XP-002372384.

George, P., et al., "Combination of the Histone Deacetylase Inhibitor LBH589 and the Hsp90 Inhibitor 17-AAG is Highly Active Against Human CML-BC Cells and AML Cells With Activating Mutation of FLT-3," Blood 105(4):1768-1776.

Gerritsen et al, "Current and Emerging Treatment Options; for Castration-Resistant Prostate Cancer: A Focus; on Immunotherapy", J Clin Immul, 32:25-35 (2012).

Giri S, et al.; Asian Journal of Chemistry (1992), 4(4), 812-17.

Giubellino et al, "Targeting Heat Shock Protein 90 for the Treatment of Malignant Pheochromocytoma", PLoS One, 8:1-9 (2013).

Goennert, R., et al., "Constitution and Cestocidal effect in the Yornesan Series," Med. Chern., Abhandl. Med. Chern., Chemical Abstracts Service, Database CA [online] 7:540-567 (1963).

Gogoi, P. C., et al., "Synthesis of 3-(2,4-dichlorophenyl)-4-substituted-5-mercapto-1,2,4-triazoles and their derivatives," *Indian Journal of Chemistry* 298:1143-1145 (Dec. 1990).

Goldman et al, "A first in human, safety, pharmacokinetics, and clinical activity phase I study of once weekly; administration of the Hsp90 inhibitor ganetespib; (STA-9090) in patients with solid malignancies", BMC Cancer, 13:152 (2013).

Goldman et al, "A phase I dose-escalation study of the Hsp90 inhibitor STA-9090 administered once weekly in patients with solid tumors", Poster, the 2010 American Society of Clinical Oncology (ASCO) Annual Meeting, Jun. 4-8, 2010—Chicago, IL.

Goldman, "Phase 2 Study of Ganetespib (STA-9090) in Subjects with Stage IIIB or IV Non-Small Cell Lung Cancer—A Preliminary Report", Presentation, International Association for the Study of Lung Cancer (IASLC) 11th Annual Targeted Therapies for the Treatment of Lung Cancer, Feb. 26, 2011—Santa Monica, CA.

Goswami, B. N., "Synthesis and Biological Activity of some 0,0-Diethyldithiophosphates/thiophosphates of 3-Substituted-5-mercapto-1,2,4-s-triazoles," *J. Indian Chem. Soc.*, vol. LXIV:422-424 (Jul. 1987).

Goswami, B. N., et al., "Alkylation of thiols using KOH in dimethyl sulphoxide," *Indian Journal of Chemistry* 318:703-704 (Oct. 1992).

Goswami, B.N., et al., "Synthesis and Antibacterial Activity of 1-(2,4-Dichlorobenzoyl)-4-Substituted Thiosemicarbazides, 1,2,4-Triazoles and Their Methyl Derivatives," Journal of Heterocyclic Chemistry 21(4): 1225-1229 (Jul.-Aug. 1984).

Goswami, B.N., et al., "Synthesis and Antifungal Activities of Some New Substituted 1,2,4-Triazoles and Related Compounds," *Journal of the Indian Chemical Society LXI*(6): 530-533 (1984).

Goyal et al, "A phase I and pharmacokinetic study of ganetespib (STA-9090) in advanced hepatocellular carcinoma." Invest New Drugs pp. 1-10 (2014).

Grashey, R., et al., "Zur Synthese Mesoionischer 1,2,4-Triazol-3-Thione," Tetrahedron Letters 29: 2939-2942 (1972).

Grbovic et al, "V600E B-Raf requires the Hsp90 chaperone for stability and is degraded in response to Hsp90 inhibitors", PNAS, 103:57-62, published online Dec 21, 2005.

Guzi et al., "Targeting the Replication Checkpoint Using SCH 900776, a Potent and Functionally Selective CHK1 Inhibitor Identified via High Content Screening" Molecular Cancer Therapeutics, vol. 10(4): 591-602, Apr. 1, 2011.

Günay, N. S. et al., "5-Nitroimidazole derivatives as possible antibacterial and antifunal agents," II Farmaco, 54:826-831 (1999).

Hainsworth, et al., J Thor Onc, 2010, 5(10),1630-1636.

Hande, et al., "Topoisomerase II inhibitors," Update on Cancer Therapeutics, 2008; 3(1), 1326.

Harris, S.F., et ai., "The Crystal Structure of the Carboxy-Terminal Dimerization Domain of htpG, the *Escherichia coli* Hsp90, Reveals a Potential Substrate Binding Site," *Structure*, 2004, 12, pp. 1087-1097.

Harvey et al, "A phase 1 and pharmacokinetic study of ganetespib (STA-9090), a heat shock protein 90 inhibitor, in combination with docetaxel in patients with advanced solid tumor malignancies", Poster, The European Multidisciplinary Cancer Congress, Sep. 26, 2011—Stockholm, Sweden.

He et al, "Inhibition of mTOR enhances the activity of HSP90 inhibitors in part through cessation of heat shock protein synthesis", Poster, the 2013 Annual Meeting of the American Association of Cancer Research (AACR), Apr. 6-10, 2013—Washington D.C.

(56) References Cited

OTHER PUBLICATIONS

He et al, Multi-Targeted Activity of the Hsp90 Inhibitor Ganetespib (STA-9090) in Prostate Cancer Cells, Poster, the Endocrine Society's 93rd Annual Meeting & Expo 2011, Jun. 5, 2011—Boston, MA.
He et al, "Potent activity of the Hsp90 inhibitor ganetespib in prostate cancer cells irrespective of androgen receptor status or variant receptor expression", Int J Oncology, 42:35-43 (2013).
He et al, "The HSP90 inhibitor ganetespib has chemosensitizer and radiosensitizer activity in colorectal cancer models", Poster, 105th Annual Meeting of the American Association for Cancer Research, Apr. 5-9, 2014—San Diego, CA.
He et al, "The HSP90 inhibitor ganetespib has chemosensitizer and radiosensitizer activity in colorectal cancer", Invest New Drugs, 32:577-586 (2014).
Health et al, "Phase II Trial of Ganetespib (STA-9090), a Heat Shock Protein (Hsp90) Inhibitor in Patients with Metastatic Castration-Resistant Prostate Cancer (CRPC) Pretreated with Docetaxel-Based Chemotherapy; a Prostate Cancer Clinical Trials Consortium (PCCTC) Study", The 2013 American Society of Clinical Oncology (ASCO) Annual Meeting, May 31-Jun. 4, 2013—Chicago, IL.
http://info.cancerresearchuk.org/healthyliving/introducingcancerprevention/.
http://www.cancer.gov/cancertopics/types/alphalist/y.
http://www.merriam-webster.com/dictionary/prevent.
Huanjie Yang et al., "Clinical development of novel proteasome inhibitors for cancer treatment", Expert Opinion on Investigational Drugs, Informa Healthcare, United Kingdon, vol. 18, No. 7, pp. 957-971 (2009).
Husain, S., et al., "3,4-Distributed 5-Hydroxy-1,2,4-triazoles Derived from 4-Substituted Semicarbazones," Indian Journal of Chemistry, 9: 642-646 (1971).
Hwang M, et. al., HSP90 Inhibitors: MUlti-Targeted Antitumor Effects and Novel Combinational Therapeutic Approaches in Cancer Therapy. Current Medicinal Chemistry, Vali 6(24) pp. 3081-3092 (2009).
Ikizler, A., and Un, R., "Reactions of Ester Ethoxycarbonylhydrazones With Some Amine Type Compounds," *Chimica Acta Turcica*, 7: 269-290 (1979).
Ikizler, a., et al., "Biological Activities of Some 1,2,4-triazoles and 1,2,4-triazolin-5-ones," *Die Pharmazie*, 44(7): 506-507 (1989).
Ikizler, A., et al., "Synthesis of some New N,N'-Linked Biheteroaryls," *Polish Journal of Chemistry*, 69:1497-1502 (1995).
Ikizler, A.A and Yuksek, H., "A Study on 4,5-Dihydro-1H-1,2,4-Triazol-5-Ones," Revue Roumaine de Chimie, 41(7-8): 585-590 (1996).
Ikizler, A.A. And Yuksek, H., "Synthesis of 3-Alkyl-4-(2-Hydroxyethyl)- and 3-Alkyl-4-(2- Chloroethyl)-4,5-Dihydro-1H-1,2,4-Triazol-5-Ones," Turkish Journal of Chemistry, 16(4): 284-288 (1992).
Ikizler, A.A. And Yuksek, H., "Acetylation of 4-Amino-4,5-Dihydro-1H-1,2,4-Triazol-5-Ones," Organic Preparations and Procedures Int., 25(1): 99-105 (1993).
Ikizler, A.A. et al., "Susuz Ortamda Bazi 1, 2, 4-Triazol Ve 1, 2, 4-Triazolin-5-on Turevlerinin pKa Degerlerinin Hesaplanmasi," Turkish Journal of Chemistry, 12(1):57-66 (1988).
Ikizler, A.A. et al., "Synthesis and Biological Activities of Some 4,5-Dihydro-1H-1,2,4-Triazol-5- One Derivatives," *Acta Poloniae Pharmaceuticals—Drug Research*, 55(2) 117-123 (1998).
Ikizler, A.A. et al., "Ultraviolet Spectra of Some 1, 2, 4-Triazole Derivatives," J. of Chemistry, 16:164-170 (1992).
Infante et al. A Phase I Dose-Escalation Study of the Oral Heat Shock Protein 90 Inhibitor PF-04929113 (SNX5422) and Its Associated Ocular Toxicity; Presented at the 22nd EORTC-NCI-AACR Symposium on Molecular Targets and Cancer Therapeutics, Berlin, Germany, Nov. 16-19, 2010. downloaded from http://www.hsp90central.com.
Iorga, T. et al., "Studial Activit ii Biologice a unor Noi Tiosemicarbazide i a Derive ilor Acestora cu Nucleu Triazolic i Tiadiazolic I. Testarea Toxicit ii," Farmacia, XXVIII(2): 103-114 (1980).

Jez, J., et ai., "Crystal Structure and Molecular Modeling of 17-Dmag in Complex with Human Hsp90," *Chemistry & Biology*, 2003, 10, pp. 361-368.
Jhaveri et al, "A Phase I Clinical Trial of Ganetespib (Heat shock protein 90 inhibitor) in Combination with Paclitaxel and Trastuzumab in Human Epidermal Growth Factor Receptor-2 Positive (HER2+) Metastatic Breast Cancer", Poster, San Antonio Breast Cancer Symposium, Dec. 9 - 13, 2014 - San Antonio, Tx.
Jhaveri et al, "A Phase II Open-Label Study of Ganetespib, a; Novel Heat Shock Protein 90 Inhibitor for Patients With Metastatic Breast Cancer", Clin Breast Cancer, 14:154-160 (2014).
Jhaveri et al, A Phase II trial of Ganetespib: Efficacy and safety in patients (pts) with metastatic breast cancer (MBC), Poster, 34th Annual CTRC-AACR San Antonio Breast Cancer Symposium, Dec. 7, 2011—San Antonio, TX.
Ji. H., et al: "Mutations in BRAF and KRAS Converge on Activation of the Mitogen-Activated Protein Kinase Pathway in Lung Cancer Mouse Model" Cancer Research 67: 4933-4939, 2007.
Kabakov et al., Hsp90 inhibitors as promising agents for radiotherapy, Journal of Molecular Medicine, vol. 8, No. 33, pp. 241-247 (2009).
Katayama et al: "Therapeutic strategies to overcome crizotinib resistance in non-small cell lung cancers harboring the fusion oncogene EML4-ALK", Proceedings of the National Academy of Sciences, National Academy of Sciences, US, vol. 1 08, No. 18, May 3, 2011, pp. 7535-7540.
Kauh et al, "A phase 1 dose escalation study of ganetespib (STA-9090), a heat shock protein 90 inhibitor, in combination with docetaxel in patients with advanced solid tumors", Poster, The 2012 American Society of Clinical Oncology (ASCO) Annual Meeting, Jun. 1-5, 2012—Chicago, IL.
Khan, et al., Indian Journal of Chemistry, Section B: Organic Chemistry including Medicinal Chemistry (1998) 37B, 1075-1077.
Kihana, et al.,: "High incidence of p53 gene mutation in human ovarian cancer and its association with nuclear accumulation of p53 protein and tumor DNA aneuploidy", Japanese Journal of Cancer Research, vol. 83, No. 9, (1992), pp. 978-984.
Kreusch et al, "Crystal Structures of Human HSP90a-Complexed With Dihydroxyphenylpyrazoles," *Bioorganic & Medicinal Chemistry Letters*, 15:1475-1478 (2005).
Kwak et al, "A Phase II Clinical Trial of Ganetespib (STA-9090) in Previously Treated Patients with Advanced Esophagogastric Cancer", Poster, The 2013 American Society of Clinical Oncology (ASCO) Annual Meeting, May 31-Jun. 4, 2013—Chicago, IL.
Labanauskas, L., et al., "Synthesis of 5-(2-,3- and 4-Methoxyphenyl)-4H-1,2,4-Triazole-3-Thiol Derivatives Exhibiting Anti-Inflammatory Activity," II Farmaco, 59: 255-259 (2004).
Lancet Jeffrey E et al. "A Phase I/II Trial of the Potent Hsp90 Inhibitor STA-9090 Administered Once Weekly in Patients with Advanced Hematologic Malignancies", Blood, vol. 116, No. 21, Nov. 2010, pp. 1349-1350 & 52ND Annual Meeting of the American-Society-Of-Hematology (ASH); Orlando, FL, USA; Dec. 4-7, 2010.
Lancet, "A Phase 1/2 Study of the Potent Hsp90 Inhibitor STA-9090 Administered Once Weekly in Subjects with Hematologic Malignancies", Poster, American Society of Hematology, Dec. 6, 2010—Orlando, FL.
Lang et al., "Targeting heat-shock protein 90 improves efficacy of rapamycin in a model of hepatocellular carcinoma in mice", Hepatology, vol. 49, No. 2, pp. 523-532 (2009).
Lanie et al., "Combination mammalian target of rapamycin and HSP90 inhibitor rapamycin and HSP90 inhibitor 17-allylamino-17demethoxygeldanamycin has synergistic activity in multiple myeloma", Clinical Cancer Research, the American Association for Cancer Research, US, vol. 12, No. 22, pp. 6826-6835 (2006).
Lavictoire, S.J., et al., "Interaction of Hsp90 With the Nascent Form of the Mutant Epidermal Growth Factor Receptor EGFRvIII," J. Biological Chemistry 278(7):5292-5299 (Feb. 14, 2003).
Leaf, Fortune, 2004, Time Inc., pp. 1-13.
Lee et al, "Differential sensitivities to heat shock protein 90 (HSP90) inhibitors in anaplastic lymphoma kinase (ALK)-positive non-small cell lung cancer (NSCLC) cells", Poster, The 2013 Annual Meeting of the American Association of Cancer Research (AACR), Apr. 6-10, 2013—Washington D.C.

(56) References Cited

OTHER PUBLICATIONS

Lee et al,"Mechanism(s) of action and potency of Hsp90 inhibitor ganetespib in small cell lung carcinoma cells", Poster, IASLC 14th World Conference on Lung Cancer, Jul. 5, 2011—Amsterdam, The Netherlands.

Lee, A.Y., et al., "Late relapse in patients with diffuse large-cell lymphoma treated with MACOP-B," *J. Clin. Oncol* 15(5):1745-1753 (1997).

Li et al, "Erlotinib Effectively Inhibits JAK2V617F Activity and Polycythemia Vera Cell Growth", J Biol Chem, 282(6): 3428-3432 (2007).

Li et al: "Radiation/Paclitaxel Treatment of p53-Abnormal Non-Small Cell Lung Cancer Xenograft Tumor and Associated Mechanism", Cancer Biotherapy & Radiopharmaceuticals, vol. 27, No. 4, 2012, pp. 227-233.

Li Y et al., "New developments in Hsp90 inhibitors as anti-cancer therapeutics: Mechanisms, clinical perspective and more potential", Drug Resistance Updates, Churchill Livingstone, Edinburgh, GB, vol. 12, No. 1-2, pp. 17-27 (2009).

Lin et al, "Heat shock protein 90 inhibition limits the emergence of tamoxifen resistance", Poster, San Antonio Breast Cancer Symposium, Dec. 12, 2010—San Antonio, TX.

Lin et al, "The novel HSP90 inhibitor STA-9090 exhibits activity against Kit dependent and independent malignant mast cell tumors", Abstract, 99th AACR Annual Meeting, Apr. 12-16, 2008; San Diego, CA.

Lin et al, "The novel HSP90 inhibitor Sta-9090 exhibits activity against Kit-dependent and -independent malignant mast cell tumors", Exp Hematol, 36:1266-1277 (2008).

Liu et al, "Network Analysis Identifies an HSP90-Central Hub; Susceptible in Ovarian Cancer", Clin Cancer Res, 19:5053-5067 (2013).

Lixue, Z., et al., "Studies on Acylthiosemicarbazides and Related Heterocyclic Derivatives," *Chemical Journal of Chinese Universitiesc1* 1(2): 148-153 (1990).

London et al, "Phase I evaluation of STA-1474, a pro-drug of the novel HSP90 inhibitor ganetespib (formerly STA-9090), in dogs with spontaneous cancer", Poster, 102nd AACR Annual Meeting, Apr. 4, 2011—Orlando, FL.

London et al,"The importance of dose schedule with Hsp90 inhibitors: Results from a Phase II study in dogs with mast cell tumors", Poster, The 2013 Annual Meeting of the American Association of Cancer Research (AACR), Apr. 6-10, 2013—Washington D.C.

London et al., "Phase I Evaluation of STA-1474, a Prodrug of the Novel HSP90 Inhibitor Ganetespib, in Dogs with Spontaneous Cancer", PLOS ONE, vol. 6, No. 11, p. e27018 (2011).

Lu Kuaike, et al., "Synthesis and anti-tumor activities of 4β-S-(5"-alkyl-4"-amino-1",2"-,4"- triazole-3"-yl)-4-deoxy-4'-o-demethyl-epipodophyllotoxin derivatives", Acta Pharmaceutia Sinica, 1999, 34(1), pp. 63-66.

Mahaseth et al, "Antiangiogenic Effects Associated with the Inhibition of HSP90 in Colorectal Cancer", Poster, 103rd Annual Meeting American Association for Cancer Research (AACR), Mar. 31-Apr. 4, 2012—Chicago, IL.

Malbec, F., et al., "Derives de la Dihydro-2,4 Triazole-1,2,4 Thione-3 et de l-amino-2 Thiadiazole-1,3,4 a Partir de Nouvelles Thiosemicarbazones d'esters," Journal of Heterocyclic Chemistry 21(6): 1689-1698 (Nov.-Dec. 1984).

Maliszewska, A., "The Reaction of N3-Substituted Amidrazones with Urea," Annales Universitatis Mariae Curie-Sklodowska Lublin-Polonia, vol. XLI, 5, Sectio AA:63-67 (1986).

Mansfield, Ten-Year Results in 1070 Patients with Stages I and II Breast Cancer Treated by Conservative Surgery and Radiation Therapy, Cancer, 1995, 75(9), pp. 2328-2336.

Marubayashi et el., "Hsp90 is a therapeutic target in JAK2-dependent myeloproliferative neoplasms in mice and humans", The Journal of Clinical Investigation, vol. 120, No. 10, pp. 3578-3593 (2010).

Mazzone, et al., "Cyclic Derivatives from Alkoxybenzohydrazides. Synthesis of Pyrazoles, Pyrroles and Triazol-5-Ones of Pharmaceutical Interest," Eur. J. Med. Chem.—Chim. Ther., 21(4): 277-284 (1986).

McCleese et al, "The novel HSP90 inhibitor STA-12 1474 exhibits biologic activity against canine osteosarcoma cell lines", Abstract, 99th AACR Annual Meeting—Apr. 12-16, 2008; San Diego, CA.

McNamara A, Potentiation of Topoisomerase I inhibitors by Hsp90 inhibitors: Mechanistic and Functional studies. British Library EThOS, 2007 University of Liverpool. Retrieved from the Internet: URL:http://ethos.bl.uk/OrderDetails.do?uin=uk.bl.ethos.485908 [retrieved on Dec. 5, 2012].

McNamara AV, et al., Identification and characterisation of proteins interacting with eukaryotic DNA topoisomerase I. Gut, vol. 54, p. A34 (2005).

Mendillo et al, "Cancer chemotherapy: An unfolding story", Abstract, The 6th International Symposium on Heat Shock Proteins in Biology and Medicine, Nov. 3-7, 2012—Washington D.C.

Milcent, R. And Redeuilh, C., "Recherche en Serie du Triazole-1,2,4. II—Reactivite des Amino-4 Aryl-3 Triazp;-1,2,4 Ones-5," Journal of Heterocyclic Chemistry, 17(8): 1691-1696 (1980).

Milcent, R., and Vicart, P., "Synthése Et Activité*Antibacteriénne D'amino-4 Triazol-1,2,4 Ones-5 Substituées*," Eur. J. Med. Chem.—Chim. Ther., 18(3): 215-220 (1983).

Mitchell et al., "In vitro and in vivo Radiation Sensitization of Human Tumor Cells by a Novel Checkpoint Kinase Inhibitor, AZD7762", Clinical Cancer Research, vol. 16, No. 7, pp. 2076-2084 (2010).

Mitsiades et al., "HSP90 Molecular Chaperone: a Novel therapeutic Target for B-Cell Lymphomas and Multiple Myeloma," Annals of Oncology, 13 (Suppl. 2):168, abstract #601 (2002).

Modzelewska, B., "Cyclization Reaction of Thiosemicarbazone-4-Picolinamide Derivatives," Acta Poloniac Pharmaceutica-Drug Research, 52(5):425-427 (1995).

Modzelewska, B., "On the Reaction of Cyclization of p-Phenylenobis-(-N3-2- pikolinamidrazonu)," Annales Universitatis Mariae Curie-Sklodowska Lublin-Polonia, vol. XLVI/XLVII, 10, Sectio AA:61-66 (1991/1992).

Modzelewska, B., "Studies on the Reaction of N3-Substituted Amidrazones with Metoxycarbonylethyl Isothiocyanate Part I," *Annales Universitatis Mariae Curie-Sklodowska Lublin-Polonia*, vol. XLI (3): 45-52 (1986).

Modzelewska, B., "Studies on the Reaction of N3-Substituted Amidrazones with Metoxycarbonylethyl Isothiocyanate Part II," *Annales Universitatis Mariae Curie-Sklodowska Lublin-Polonia*, vol. XLI (4): 53-61 (1986).

Modzelewska, B., "Studies on the Reaction of N3-Substituted Amidrazones with Metoxycarbonylethyl lsothatcyanate Part II," Annales Universitatis Mariae Curie-Sklodowska Lublin-Polonia, vol. XLI 5: 63-67 (1986).

Modzelewska, B., and Maliszewska, A., "The Reaction of N3-substituted Amidrazones with the Aromatic Izothiocyanates, Part III," vol. XXXIXIXL, 13: 163-170 (1985).

Modzelewska-Banachiewicz, B., et al., "Synthesis and Biological Activity of BIS-1, 2, 4-Triazole and BIS-1, 3, 4-Thiadiazole Derivatives," *Acta Poloniac Pharmaceutica Drug Research*, 57(3): 199-204 (2000).

Morissette et al. Adv. Drug Delivery Rev. 56:275 (2004).

Moser C, et al., Blocking heat shock protein-90 inhibits the invasive properties and hepatic growth of human colon cancer cells and improves the efficacy of oxaliplatin in p53-deficient colon cancer tumors in vivo. Molecular Cancer Therapeutics, vol. 6(11) pp. 2868-2878, (2007).

Nagaraju et al, "Antiangiogenic activity of the HSP90 inhibitor ganetespib in pancreatic cancer models", Poster, Experimental Biology 2013, Apr. 20-24, 2013—Boston, MA.

Nagaraju et al, "Heat Shock Protein 90 Functional Inhibition Regulates Epithelial to Mesenchymal Transformation, Invasion and Migration via $NF_{-\kappa}b$ and HIF-1α Signaling in Colorectal Cancer,", Poster, The 2013 Annual Meeting of the American Association of Cancer Research (AACR), Apr. 6-10, 2013—Washington D.C.

Nagaraju et al, "Heat Shock Protein 90 Promotes Epithelial; to Mesenchymal Transition, Invasion, and Migration in Colorectal Cancer", Mol Carcinog (2014).

Nagourney Robert A et al: "Geldenamycin and 17-allylamino-17—demethoxygeldenamycin alone and in combination with cytotoxic drugs in human tumor primary cultures.", Proceedings of the American Association for Cancer Research Annual Meeting, 2005, 46, p.

(56) References Cited

OTHER PUBLICATIONS

404, & 96th Annual Meeting of the American-Association-For-Cancer-Research; Anaheim, CA, USA; Apr. 16-20, 2005.

Nakatani, H., et al., "STI571 (Glivec) Inhibits the Interaction Between c-KIT and Heat Shock Protein 90 of the Gastrointestinal Stromal Tumor Cell Line, GIST-T1," Cancer Sci 96(2):116-119 (Feb. 2005).

National Cancer Institute. Understanding Cancer Series: What is Tumor Angiogenesis. Jan. 28, 2005. http://www.cancergovicancertopics/understandingcancer/angiogenesis/Slide- 3.

Neckers., "Heat Shock Protein 90: the Cancer Chaperone," J of Biosci, 32(3) Apr. 2007, pp. 517-530.

Nehs, M.A., et al., PLX4720 Induces Tumor Regression, Reverses Cachexia, and Extends Survival in a Mouse Model of Late-Stage Anaplastic Thyroid Cancer, Journal of the American College of Surgeons, College, Chicago, IL, 211(3):S124: Sep. 1, 2010.

Neidle, Cancer Drug Design and Discovery, Elsevier/Academic Press, 2008, pp. 427-431.

Nguyen, D M et al: "Modulation of Metastasis Phenotypes of Non-Small Cell Lung Cancer Cells by 17-Allylamino 17-Demethosy Geldanamycin" The Annals of Thoracic Surgery, 70: 1853-1860, 2000.

Noguchi et al., "Inhibition of homologous recombination repair in irradiated tumor cells pretreated with Hsp90 inhibitor 17-allylamino-17-demethoxygelda namycin", BioChemical and Biophysical Research Communications, vol. 352, No. 3, pp. 658-663 (2006).

Nwizu T et al: "Crizotinib ALK/Met inhibitor Oncolytic", Drugs of the Future, Prous Science, ES, vol. 36, No. 2, Feb. 1, 2011, pp. 91-99.

Ogura, et al., "Studies on Nucleoside Analogs. XXI. A Convenient Synthesis of 1,2,4-triazole5-thione glycosides", Chemical and Pharmaceutical Bulletin 29(8), 2188-92 (1981).

Padmanabhan et al, "A Phase I Study of the Potent Hsp90 Inhibitor STA-9090 Administered Twice Weekly in Subjects with Hematologic Malignancies", Poster, American Society of Hematology, Dec. 5, 2010—Orlando, FL.

Padmanabhan et al, "Hsp90 Inhibitor STA-9090 Downregulates Expression of Hsp90 Client Protein WT1 in Myeloid Leukemia Cells", Poster, Hematologic Malignancies: Bridging the Gap 2010, Feb. 5-7, 2010—Singapore City, Singapore.

Paraiso, Kim H.T., et al., the HSP90 Inhibitor XL888 Overcomes BRAF Inhibitor Resistance Mediated through Diverse Mechanisms, Clinical Cancer Research, 18(9):2502-2514, May 2012.

Parasramka et al, "Preclinical activity of the heat shock protein 90 (hsp90) inhibitor ganetespib in clear cell renal cell (ccRCC)", Poster, 2014 Genitourinary Cancers Symposium, Jan. 30-Feb. 1, 2014—San Francisco, CA.

Patani, et al., Chem. Rev., 1996, 96, pp. 3147-3176.

Patel et al, "Heat shock protein 90 (HSP90) inhibition in squamous cell carcinoma of the head and neck (SCCHN): an in vitro analysis with a focus on p16 status", Poster, The 2013 American Society of Clinical Oncology (ASCO) Annual Meeting, May 31-Jun. 4, 2013—Chicago, IL.

Petricoin et al, "Gene Expression and Proteomic Analysis to Identify Predictive Biomarkers of Response in the ENCHANT-1 Trial (NCT01677455), a Phase 2 Proof of Concept Study Evaluating First-Line Ganetespib Monotherapy in Women with Metastatic HER2 Positive or Triple Negative Breast Cancer (TNBC)", Poster, 105th Annual Meeting of the American Association for Cancer Research, Apr. 5-9, 2014—San Diego, CA.

Pommier Y, et al., DNA Topoisomerases and Their Poisoning by Anticancer and Antibacterial Drugs. Chemistry & Biology, vol. 17(5), pp. 421-433 (2010).

Pommier Y, Topoisomerase I inhibitors: Camptothecins and beyond. Nature Reviews Cancer. vol. 6(10) pp. 789-802, (2006).

Potts, K.T., et al., "meso Ionic Compounds. II. Derivatives of the s-Triazole Series," *The Journal of Organic Chemistry, 32*(7): 2245-2252 (1967).

Powers et al, "Targeting of mutiple signalling pathways by heat shock protein 90 molecular chaperone inhibitors", Endocr Relat Cancer, 13:S125-S135 (2006).

Premkumar et al., "Synergistic interaction between 17-AAG and phosphatidylinositol 3-kinase inhibition in human malignant glioma cells", Molecular Carcinogenesis, vol. 45, No. 1, pp. 47-59 (2006).

Prodromou, C., et aL, "Identification and Structural Characterization of the ATP/ADP-Binding Site in the Hsp90 Molecular Chaperone," *Cell*, 1997, 90, pp. 65-75.

Proia D. et al., "Preclinical activity of the Hsp90 inhibitor, ganetespib, in Alk- and ROS1-driven cancers.", American Society of Cancer Oncology Annual Meeting, Jun. 1-5, 2012 (abstract).

Proia et al, "Anti-metastatic activity, chemotherapeutic enhancement and therapeutic potential of targeting Hsp90 with ganetespib in triple negative breast cancer", Poster, San Antonio Breast Cancer Symposium, Dec. 10-14, 2013—San Antonio, TX.

Proia et al, "Antimetastatic activity of ganetespib: preclinical studies and assessment of new lesion growth in the GALAXY-1 NSCLC trial", Poster, 15th World Conference on Lung Cancer, Oct. 27-30, 2013—Sydney, Australia.

Proia et al, "Antimetastatic activity of ganetespib: preclinical studies and assessment of progressions due to new lesions in the GALAXY-1 NSCLC trial", Poster, European Cancer Congress 2013 (ECCO-ESMO-ESTRO), Sep. 27-Oct. 1, 2013—Amsterdam, The Netherlands.

Proia et al, "Combination of the Hsp90 Inhibitor Ganetespib (STA-9090) With Docetaxel Displays Synergistic Anticancer Activity in Solid Tumor Cells", Poster, 9th International Symposium on Targeted Anticancer Therapies, Mar. 7-9, 2011—Paris, France.

Proia et al, "Ganetespib and HSP90: Translating Preclinical Hypotheses into Clinical Promise", Cancer Res, 74:1294-1300 (2014).

Proia et al, "Multifaceted Intervention by the Hsp90 Inhibitor Ganetespib (STA-9090) in Cancer Cells with Activated JAK/STAT Signaling", PLoS ONE, 14:e18552 (2011).

Proia et al, "Multimodal Action of the Hsp90 Inhibitor STA-9090 in Treating Cancer Cells With Activated JAK/STAT Signaling", Poster, 101st AACR Annual Meeting, Apr. 19, 2010—Washington, DC.

Proia et al, "Preclinical activity of the Hsp90 inhibitor, ganetespib, in ALK- and ROS1-driven ,cancers", Poster, The 2012 American Society of Clinical Oncology (ASCO) Annual Meeting, Jun. 1-5, 2012—Chicago, IL.

Proia et al, "Preclinical Activity Profile and Therapeutic Efficacy of the HSP90 Inhibitor Ganetespib in Triple-Negative; Breast Cancer", Clin Cancer Res, 20:413-424 (2013).

Proia et al, "Synergistic activity of the Hsp90 inhibitor ganetespib with taxanes in non-small cell lung cancer models", Invest New Drugs, 30:2201-2209 (2012).

Ramazani, A. et al., "Crystal structure of 4-[4-(dimethylamino)phenyl]-5-(2, 4-dimethyl-1, 3- thiazol-5yl)-2, 4-dihydro-3H-1, 2, 4-triazol-3-thione, C15H17N5S2," K. Kristallogr, NCS, 217:149-150 (2002).

Ravi, T.K. & Rajkannan, R., "Synthesis and antimicrobial Activity of Some New 1,2,4- Triazoles," *Indian J. Of Pharmaceutical Sciences*, 66(3), 347-350 (2004).

Reichert et al, "Ganetespib: An effective strategy to overcome crizotinib resistance in ALK-driven cancers", Poster, 3rd European Lung Cancer Conference (IASLC/ESMO), Apr. 18-21, 2012—Geneva, Switzerland.

Rich et. al., Nature Reviews, 2004, Nature Publishing Group, vol. 3, pp. 430-446.

Robertus, et al., Toxicon, 1996, 34:1325-1334.

Romine, et al., "4,5-Diphenyltriazol-3-ones: Openers of large-conductance Ca2+-activated potassium (Maxi-K) channels," *J. Med. Chem.*(2002), 45:2942-2952.

Rostom, S.A.F., et al., "Polysubstituted Pyrazoles, Part 5. Synthesis of new 1-(4- Chlorophenyl)-4-Hydroxy-1H-Pyrazole-3-Carboxylic Acid Hydrazide Analogs and Some Derived Ring Systems. A Novel Class of Potential Antitumor and Anti-HCV Agents,"European J Med Chem, 38:959-974 (2003).

Rouhi, Chem. & Eng. News, Feb. 24, 2003, 81(8), 32-35.

Russo, et al., "Derivati Benzotiazolici del 1,2,4-triazolo," *Annali di Chimica*, 62: 351-372 (1972).

Samanta et al., Destabilization of Bcr-Abl/Jak2 Network by a Jak2/Abl Kinase Inhibitor 0N044580 Overcomes Drug Resistance in Blast Crisis Chronic Myelogenous Leukemia, Genes and Cancer, vol. 1, No. 4, pp. 346-359 (2010).

(56) References Cited

OTHER PUBLICATIONS

Sang et al, "Novel Hsp90 Inhibitor, Ganetespib (STA-9090), for Combination With Radiotherapy", Poster, 102nd AACR Annual Meeting, Apr. 4, 2011—Orlando, FL.

Sang et al, "Targeted Inhibition of the Molecular Chaperone Hsp90 Overcomes ALK Inhibitor Resistance in Non-Small Cell Lung Cancer," Cancer Discov, 3:430-443 (2013).

Sawai Ayana et al: "Inhibition of Hsp90 down-regulates mutant epidermal growth factor receptor (EGFR) expression and sensitizes EGFR mutant tumors to paclitaxel", Cancer Research. 2008, 68(2), pp. 589-596.

Sawhney, et al., "Synthesis and Anti-inflammatory Activity of Some 3-Heterocyclyl-1,2- Benzisothiazoles," Indian J. of Chem., 32B, 1190-1195 (1993).

Sawhney, et al., "Synthesis of Some 2-(5-Substituted 1,3,4-Oxadiazol-2-YI)-, 2-(5-Substituted 1,3,4-Thiadiazol-2-YI)- and 2-(3-Mercapto-4-Substituted-4H-1,2,4-Triazol-5-YI)-Benzimidazoles as Potential Anti-Inflammatory Agents," Indian J. of Chem., 30 B:407-412 (1991).

Schag, et al., "Identification of C-Met Oncogene as a Broadly Expressed Tumor-Associated Antigen Recognized by Cytotoxic T-Lymphocytes", Clinical Cancer Research, 2004, vol. 10, pp. 3658-3666.

Schoof et al., "Hsp90 is essential for Jak-STAT signaling in classical Hodgkin lymphoma cells', Cell Communication and Signaling", vol. 7, No. 1, p. 17 (2009).

Seeger-Nukpezah et al, "Inhibiting the HSP90 chaperone slows cyst growth in a mouse model of autosomal dominant polycystic kidney disease", PNAS, 110:12786-12791 (2013).

Seike et. al., Cancer Letters, 2003, Elsevier, vol. 192, pp. 25-36.

Sen, et al., Indian Journal of Heterocyclic Chemistry (2005) 14(3), 269-270.

Senthilvelan, A. et al., "Photodesulfurization of 2, 4-Diaryl-1, 2, 4-Triazole 3-Thiones,"*Heteroatom Chemistry*, 14(3):269-272 (2003).

Sequist et al., "Association between Anaplastic Lymphoma reearrangements (rALK) and the clinincal activity of IPI-504 (retaspimycin hydrochloride), a novel Hso90 inhibitor, inpatients with non-small cell lung cancer (NSCLC)", ASCO Annual Meeting, Abstract, Jun. 4-8, 2010.

Serra et al., "NVP-BEZ235, a Dual PI3K/mTOR Inhibitor, Prevents PI3K Signaling and Inhibits the Growth of Cancer Cells with Activating PI3K Mutations", Cancer Research, vol. 68, No. 19, pp. 8022-8030 (2008).

Shafi et al, "Differential Responsiveness of Androgen Receptor Splice Variants to Regulators of Androgen Receptor Action", Poster, The Endocrine Society's 94th Annual Meeting & Expo, Jun. 24, 2012—Houston, TX.

Shah, et al., "3,4-Disubstituted-5-carboxymethylthio-4H-1,2,4-triazoles as possible antiviral agents," Indian J. Chem 5:391-393 (1967).

Shapiro, "HSP90 Inhibitors in Clinical Development: STA-9090 (ganetespib)", Presentation, 9th International Symposium on Targeted Anticancer Therapies, Mar. 7-9, 2011—Paris, France.

Shapiro, "STA-9090 A Potent 2nd Generation Hsp90 Inhibitor", 10th Annual Targeted Therapies of Lung Cancer Meeting, Presentation, Feb. 25, 2010—Santa Monica, CA.

Shapiro: "Phase II study of the Hsp90 inhibitor ganetespib as monotherapy in patients with advanced NSCLC", Internet-U-Tube, Jun. 2011, Retrievedfrom the Internet: URL:http//www.youtube.com/watch?v=UX8fEZbFlbk.

Shaw et al, Clin Cancer Res; 17(8) Apr. 15, 2011.

Shimamura et al, "The novel Hsp90 inhibitor STA-9090 has potent anticancer activity in in vitro and in vivo models of lung cancer", Poster, 100th AACR Annual Meeting, Apr. 21, 2009—Denver, CO.

Shimamura et al,"Ganetespib (STA-9090), a Non-Geldanamycin HSP90 Inhibitor, has Potent Antitumor Activity in in Vitro and in Vivo Models of Non-Small Cell Lung Cancer", Clin Cancer Res, 18:4973-4985 (2012).

Shimamura, T., et al.: "Hsp90 Inhibition Suppresses Mutant EGFR-T790M Signaling and Overcomes Kinase Inhibitor Resistance" Cancer Research, 68: 5827-5838, 2008.

Shinmamura, T. et al., "The novel Hsp90 inhibitor STA-9090 has potent anticancer activity in in vitro and in vivo models of lung cancer", 100th AACR Annual Meeting, Apr. 18-21, p. 4679, 2009 (abstract). XP055067116.

Siavash, H. et al., Critical Reviews in Oral Biology & Medicine, 15(5):298-307(2004).

Silverman, R.B., The Org. Chem. Of Drug Design and Drug Action, Academic Press, Inc.: San Diego, 1992, pp. 4-51.

Smith et al, "The HSP90 inhibitor ganetespib potentiates the antitumor activity of EGFR tyrosine kinase inhibition in mutant and wild-type non-small cell lung cancer", Targ Oncol (2014).

Smith, et al., "Preclinical pharmacokinetics and metabolism of a novel diaryl pyrazole resorcinol series of heat shock protein 90 inhibitors," *Mol. Cancer Ther.*(2006), 6(6):1628-1637.

Socinski et al, "A Multicenter Phase II Study of Ganetespib Monotherapy in Patients with Genotypically Defined Advanced Non-Small Cell Lung Cancer", Clin Cancer Res, 19 (2013).

Solit D, Egorin MJ, Valentin G, et al. Phase 1 pharmacokinetic and pharmacodynamic trial of docetaxel and 17-AAG (17-allylamino-17-demethoxygeldanamcyin) [abstract 3032]. Proceedings of the American Society of Clinical Oncology 2004, 23: 203.

Sonar, et al., "Synthesis and Antimicrobial Activity of Triazolylindoles and Indolylthiazolidinones," *Indian J. Of Heterocyclic Chem.*, 5: 269-271 (1996).

Soni, N., et al., "Analgesic Activity and Monoamine Oxidase Inhibitory Property of Substituted Mercapto 1,2,4-Triazoles," *Eur. J. Med. Chem.*, 20(2): 190-192 (1985).

Sos M.L., et al.: "Predicting Drug susceptability of non-small cell lung cancers based on genetic lesions" The Journal of Clinical Investigation, 119: 1727-1740, 2009.

Stebbins, C.E., et al., "Crystal Structure of an Hsp90-Geldanamycin Complex: Targeting of a Protein Chaperone by an Antitumor Agent," *Cell*, 199 7 89, pp. 239-250.

Stinchcombe et. al., Oncogene, 2007, Nature Publishing Group, vol. 26, pp. 3691-3698.

STN registry data for STA-9090 (2006).

Stoeltzing et al., "59 Dual targeting of mTOR and HSP90 for therapy of pancreato-biliary carcinomas", European Journal of Cancer, vol. 8, No. 7, p. 27 (2010).

Surh, Nature Reviews Cancer, 2003, Nature Publishing Group, vol. 3, pp. 768-780.

Swigris et. al., Chest, 2005, American College of Chest Physicians, vol. 127, pp. 275-283.

Synta Press Release: Synta Presents Results at AACR-IASLC Demonstrating Potent and Synergistic Activity of STA-9090 in NSCLC Cell Lines Including Mutated EGFR, HER2, and KRAS, Jan. 12, 2010.

Tandon, M., et al., "Synthesis & Antiinflammatory Activity of Some New 3-( o -Substituted phenyl)-4-Substituted-Phenyl-5-Atkyl/Alkenyl-Mercapto-1H-I,2,4-Triazoles," *Indian J. Chem.*, 2013(11):1017-1018 (1981).

Tehranchian, S. et al., "Synthesis and antibacterial activity of 1-[1, 2, 4-triazol-3-yl] and 1-[1, 3, 4-thiadiazol-2-y1]-3-methylthio-6, 7-dihydrobenzo[c]thiophen-4(5H)ones," Bioorganic & Medicinal Chemistry Letters, 15:1023-1025 (2005).

Valbuena, J.R. et al., "Expression of Heat-Shock Protein-90 in Non-Hodgkin's Lymphomas," Modern Pathology, 18:1343-1349 (2005).

Van Cutsem, Eric et al, "Phase III Trial of Bevacizumab in Combination with Gemcitabine and Erlotinib in Patients with Metastatic Pancreatic Cancer", Journal of Clinical Oncology, 27 (13), p. 2231-2237, 2009.

Walton et al., "The Preclinical Pharmacology and Therapeutic Activity of the Novel CHK1 Inhibitor SAR-020106" Molecular Cancer Therapeutics, vol. 9(1): 89-100, Jan. 1, 2010.

Wang et. al., The Journal of Nutrition, 2003, American Society for Nutritional Science, vol. 133, pp. 2367-2376.

Wang Yisong et al: "STA-9090, a small-molecule Hsp90 inhibitor for the potential treatment of cancer", Current Opinion in Investigational Drugs, Thomson Reuters (Scientific) Ltd, London, UK, vol. 11, No. 12, Dec. 1, 2010, pp. 1466-1476, XP009159004, ISSN: 2040-3429.

(56) References Cited

OTHER PUBLICATIONS

Wax et al. "Geldanamycin Inhibits the Production of Inflammatory Cytokines in Activated Macrophages by Reducing the Stability and Translation of Cytokine Transcripts", Arthr. Rheum., 2003, vol. 48, No. 2, pp. 541-550.

Webb et al. The geldanamycins are potent inhibitors of the hepatocyte growth factor/scatter factor-met-urokinase plasminogen activator-plasmin proteolytic network. Cancer Research, 60, 342-349, Jan. 15, 2000.

Who Drug Information: "International Nonproprietary Names for Pharmaceutical Substances (Inn)"30 Jun. 2011 (2011-06-30), Retrieved from the Internet: URL:http://www.whoint/medicines/;publications/druginformation/innlists/PL105.pdf?ua=1.

Wong et al, An Open-Label Phase 2 Study of the; Hsp90 Inhibitor Ganetespib (STA-9090) as Monotherapy in Patients with Advanced NSCLC, Presentation, The 2011 American Society of Clinical Oncology (ASCO) Annual Meeting, Jun. 3-7, 2011.

Workman, "Overview: Translating HSP90 Biology into HSP90 Drugs", Current Cancer Drug Targets, 2003, vol. 3, pp. 297-300.

Wright, L., et ai., "Structure, Activity Relationships in Purine-Based Inhibitor Binding to HSP90 Isoforms," *Chemistry & Biology*, 2004, 11, pp. 775-785.

Wu et al, "Activity of the Heat Shock Protein 90 Inhibitor; Ganetespib in Melanoma", PLoS One, 8:e56134 (2013).

Wu et al., Natl Cancer Inst, 95, 2003, 766-767.

Xiang et al, "Ganetespib blocks HIF-1 activity and inhibits tumor growth, vascularization, stem cell maintenance, invasion, and metastasis in orthotopic mouse models of triple-negative breast cancer", Author Manuscript, J Mol Med 92(2), 151-164 (2014).

Xie, L., et al., "Anti-AIDS Agents. 37. Synthesis and Structure-Activity Relationships of (3'R,4'R)-(+)-cis-Khellactone Derivatives as Novel Potent Anti-HIV Agents," *J. Med. Chem*.42:2662-2672 (1999).

Xu et al., "Checkpoint kinase inhibitor synergizes with DNA-damaging agents in G1 checkpoint-defective neuroblastoma" Int'l J. of Cancer, 129, pp. 1953-1962, Jan. 1, 2011.

Yamada et ai, Mol Cancer Ther 2012;11 :1112-1121. Published OnlineFirst Mar. 8, 2012.

Yang, Zhen Fan et al, "High doses of tyrosine kinase inhibitor PTK787 enhance the efficacy of ischemic hypoxia for the treatment of hepatocellular carcinoma: dual effects on cancer cell and angiogenesis", Mol. Cancer Therapeutics, 5 (9), p. 2261-2270, 2006.

Yao et al. Cancer Therapy: Preclinical; "Synergism between Etoposide and 17-AAG in Leukemia Cells: Critical Roles for Hsp90, FLT3, Topoisomerase II, Chk1, and Rad51" 2007 (13) 1591-1600.

Yao Qing et al., "The Hsp90 inhibitor 17-AAG sensitizes human leukemia cells to proteasome inhibitor Ps-341", Blood, American Society of Hematology, US, vol. 102, No. 11, pp. 622A-623A (2009).

Yao, Q., et al., "FLT3 Expressing Leukemias Are Selectively Sensitive to Inhibitors of the Molecular Chaperone Heat Shock Protein 90 Through Destabilization of Signal Transduction-Associated Kinases," Clinical Cancer Research 9:4483-4493 (Oct. 1, 2003).

Yap et al., "Targeting the PI3K-AKT-mTOR pathway: progress, pitfalls and promises", Current Opinion in Pharmacology, vol. 8, No. 4, pp. 393-412 (2008).

Ying et al, "Ganetespib, A Unique Resorcinolic Hsp90 Inhibitor, Exhibits Potent Antitumor Activity and A Superior Safety Profile in Preclinical Models", Poster, AACR-EORTC-NCI Molecular Targets and Cancer Therapeutics, Nov. 14, 2011—San Francisco, CA.

Ying et al, "Ganetespib, a Unique Triazolone-Containing Hsp90 Inhibitor,Exhibits Potent Antitumor Activity and a Superior Safety Profile for Cancer Therapy", Mol Cancer Res, 11:475-484 (2011).

Ying et al, "Preclinical Evaluation of the Potent 2nd Generation Small-Molecule Hsp90 Inhibitor STA-9090 in Hematological Cell Lines", Poster, American Society of Hematology, Dec. 5, 2010—Orlando, FL.

Ying et al: "In Vitro and in Vivo Efficacy of the Novel Hsp90 Inhibitor STA-9090 and its Synergy with Paclitaxel", Poster, AACR-NCI-EORTC Molecular Targets and Cancer Therapeutics, Nov. 17, 2009—Boston, MA.

Yousif, N.M., et al., "Reactions of n, (3-spiroepoxyalkanones, Part IV—New and Facile Synthesis of Tetrahydronaphthalen-2-ol derivatives for Biological Evaluation," Bulletin of the Faculty of Pharmacy (Cairo University), Chemical Abstracts Service, Database CA [online], 36(1):37-41 (1998).

Yu, Xiao Ming, et al, "Synthesis of (-)-Noviose from 2,3-0-lsopropylidene-D-erythronolactol" J. Org. Chem., 2004, 69 (21), pp. 7375-7378.

Yuksek, Haydar and Ikizler A. A., "Synthesis of 4-Succinimido-4,5-Dihydro-1H-1,2,4-Triazol-5-ones," Turkish Journal of Chemistry, 18: 57-61(1994).

Zhang et al. Pharmacokinetic and Toxicity Study of Intravitreal Erythropoietin in Rabbits; Acta Pharmacologica Sinica, vol. 29, No. 11 (2008) pp. 1383-1390.

Zhang et al. Targeting multiple signal transduction pathways through inhibition of Hsp90. J Mol. Med. 2004, 82: 488-499.

Zhang, et al., Chemical Research in Chinese Universities (1997), 13(1), 27-33.

Zhang, L. et al., "Studies on Acylthiosemicarbazides and Related Heterocyclic Derivatives (XII)," Chemical Journal of Chinese Universities, 11(2):148-153 (1990).

Zhou et al, " Associating Retinal Drug Exposure and Retention with the Ocular Toxicity Profiles of Hsp90 Inhibitors", Poster, The 2012 American Society of Clinical Oncology (ASCO) Annual Meeting, Jun. 1-5, 2012—Chicago, IL.

Zhou et al, "A rat retinal damage model predicts for potential clinical visual disturbances induced by Hsp90 inhibitors", toxicol Appl Pharmacol, 273:401-409 (2013).

Zhou et al, "Heat Shock Protein (Hsp) 90 Inhibitor-Induced Ocular Toxicity: Critical Role of Tissue Distribution", Poster, AACR-EORTC-NCI Molecular Targets and Cancer Therapeutics, Nov. 15, 2011—San Francisco, CA.

\* cited by examiner

CANCER THERAPY USING A COMBINATION OF A HSP90 INHIBITORY COMPOUNDS AND A EGFR INHIBITOR

CROSS-REFERENCE TO RELATED PATENT APPLICATIONS

This application is the U.S. National Stage filed under 35 USC 371 of PCT/US2011/033008, filed Apr. 19, 2011, which claims benefit of U.S. Provisional Application 61/342,820, filed on Apr. 19, 2010. The entire teachings of these two patent documents are incorporated herein by reference.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Therefore, it is less likely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation and oxygen deprivation. HSPs act as chaperones to other cellular proteins (called client proteins), facilitate their proper folding and repair and aid in the refolding of misfolded client proteins. There are several known families of HSPs, each having its own set of client proteins. The Hsp90 family is one of the most abundant HSP families accounting for about 1-2% of proteins in a cell that is not under stress and increasing to about 4-6% in a cell under stress. Inhibition of Hsp90 results in the degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer.

SUMMARY OF THE INVENTION

It is now found that certain triazolone Hsp90 inhibitors and EGFR inhibitor combinations are surprisingly effective at treating subjects with proliferative disorders without further increasing the side effect profile of the single agents. The particular combination therapies disclosed herein demonstrate surprising biological activity by demonstrating significant anticancer effects.

The present method utilizes Hsp90 inhibitors according to formulae (I) or (Ia) for the treatment of proliferative disorders, such as cancer, in combination with an EGFR inhibitor. The method includes the step of administering to a subject with cancer an Hsp90 inhibitor according to formulae (I) or (Ia) or a compound in Tables 1 or 2 and an EGFR inhibitor useful for the treatment of cancer. In one aspect, the administration of the Hsp90 inhibitor and the EGFR inhibitor are done concurrently. In another aspect, the administration of the Hsp90 inhibitor and the EGFR inhibitor are done sequentially. In another aspect, the administration of the Hsp90 inhibitor and the EGFR inhibitor are dosed independently. In any one of these embodiments, the EGFR inhibitor may be erlotinib, gefitinib or cetuximab. In any one of these embodiments, the Hsp90 inhibitor may be a compound represented by formulae (I) or (Ia), or a compound in Tables 1 or 2.

In another embodiment, a kit for administration of the combination therapy includes separate pharmaceutical compositions containing the Hsp90 inhibitor according to formulae (I) or (Ia) or a compound in Tables 1 or 2, and the EGFR inhibitor. In another embodiment, the kit includes one pharmaceutical composition containing both the Hsp90 inhibitor and the EGFR inhibitor. In any of these embodiments, each pharmaceutical composition may include one or more pharmaceutically acceptable carrier or diluent. In any one of these embodiments, the EGFR inhibitor may be erlotinib, gefitinib or cetuximab. In any one of these embodiments, the Hsp90 inhibitor may be a compound represented by formulae (I) or (Ia), or a compound in Tables 1 or 2.

In one embodiment, the method includes use of an Hsp90 inhibitor according to formulae (I) or (Ia) or a compound in Tables 1 or 2 for the manufacture of a medicament for treating cancer in combination with an EGFR inhibitor such as erlotinib, gefitinib or cetuximab.

In certain embodiments, the treatment utilizes an Hsp90 compound according to formulae (I) or (Ia) or a compound in Tables 1 or 2 with an EGFR inhibitor to help arrest, partially or fully, or reduce the development of multidrug resistant cancerous cells in a subject. In this embodiment, the combinations described herein may allow a reduced efficacious amount of the EGFR inhibitor given to a subject, because the Hsp90 inhibitor should inhibit the development of multidrug-resistant cancerous cells. In one embodiment, the EGFR inhibitor may be erlotinib, gefitinib or cetuximab. In another embodiment, the EGFR inhibitor is erlotinib.

BRIEF DESCRIPTION OF THE DRAWINGS

The foregoing and other objects, features and advantages of the invention will be apparent from the following more particular description of the embodiments, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Definitions

Figure 1:
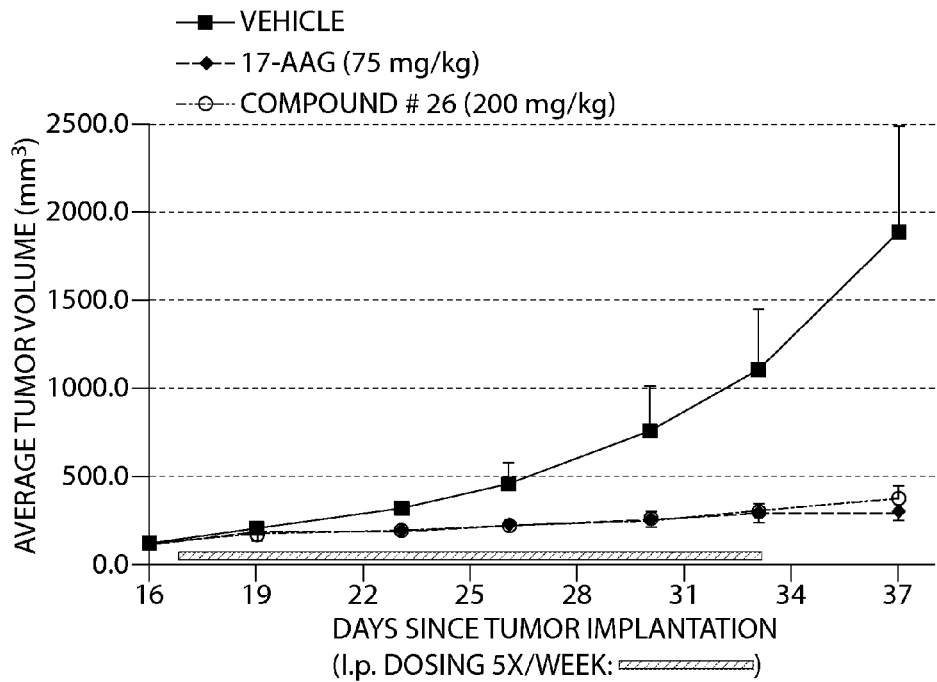
FIG. 1 displays the results of a nude mouse xenograft study on the effect of Compound 26 on the in vivo growth rate of RERF-LC-AI$^{IVP}$ human lung tumor cells. Tumor bearing animals (8 mice/group) were i.p. injected 5 times per week for a total of 15 doses (hatched bar) and the average tumor volumes for each group (error bars represent SEM) were determined every 3-4 days. Treatment with a dose of 200 mg/kg body weight of Compound 26 inhibited tumor growth, as did a dose of 75 mg/kg body weight of 17-AAG (both compounds were dosed at approximately their maximum tolerated doses in nude mice).

Unless otherwise specified, the below terms used herein are defined as follows:

As used herein, the term "alkyl" means a saturated or unsaturated, straight chain or branched, non-cyclic hydrocarbon having from 1 to 10 carbon atoms. Representative straight chain alkyls include methyl, ethyl, n-propyl, n-butyl, n-pentyl, n-hexyl, n-heptyl, n-octyl, n-nonyl and n-decyl; while representative branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl, and the like. The term "$(C_1-C_6)$alkyl" means a saturated, straight chain or branched, non-cyclic hydrocarbon having from 1 to 6 carbon atoms. Alkyl groups included in compounds described herein may be optionally substituted with one or more substituents. Examples of unsaturated alkyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkyl groups included in compounds described herein may be optionally substituted with one or more substituents.

As used herein, the term "cycloalkyl" means a saturated or unsaturated, mono- or polycyclic, non-aromatic hydrocarbon having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, cyclodecyl, octahydropentalenyl, cyclohexenyl, cyclooctenyl, cyclohexynyl, and the like. Cycloalkyl groups included in compounds described herein may be optionally substituted with one or more substituents.

As used herein, the term "alkylene" refers to an alkyl group that has two points of attachment. The term "$(C_1-C_6)$alkylene" refers to an alkylene group that has from one to six carbon atoms. Straight chain $(C_1-C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be saturated or unsaturated, and may be optionally substituted with one or more substituents.

As used herein, the term "lower" refers to a group having up to four atoms. For example, a "lower alkyl" refers to an alkyl radical having from 1 to 4 carbon atoms, "lower alkoxy" refers to "O—$(C_1-C_4)$alkyl.

As used herein, the term "haloalkyl" means an alkyl group, in which one or more, including all, the hydrogen radicals are replaced by a halo group(s), wherein each halo group is independently selected from —F, —Cl, —Br, and —I. For example, the term "halomethyl" means a methyl in which one to three hydrogen radical(s) have been replaced by a halo group. Representative halo alkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker Alkoxy groups included in compounds described herein may be optionally substituted with one or more substituents.

As used herein, a "haloalkoxy" is a haloalkyl group which is attached to another moiety via an oxygen linker.

As used herein, the term an "aromatic ring" or "aryl" means a mono- or polycyclic hydrocarbon, containing from 6 to 15 carbon atoms, in which at least one ring is aromatic. Examples of suitable aryl groups include phenyl, tolyl, anthracenyl, fluorenyl, indenyl, azulenyl, and naphthyl, as well as benzo-fused carbocyclic moieties such as 5,6,7,8-tetrahydronaphthyl. Aryl groups included in compounds described herein may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like. Aralkyl groups included in compounds described herein may be optionally substituted with one or more substituents.

As used herein, the term "heterocyclyl" means a monocyclic or a polycyclic, saturated or unsaturated, non-aromatic ring or ring system which typically contains 5- to 20-members and at least one heteroatom. A heterocyclic ring system can contain saturated ring(s) or unsaturated non-aromatic ring(s), or a mixture thereof. A 3- to 10-membered heterocycle can contain up to 5 heteroatoms, and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized, oxygen and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, a nitrogen atom may be substituted with a tert-butoxycarbonyl group. Furthermore, the heterocyclyl included in compounds described herein may be optionally substituted with one or more substituents. Only stable isomers of such substituted heterocyclic groups are contemplated in this definition.

As used herein, the term "heteroaryl", or like terms, means a monocyclic or a polycyclic, unsaturated radical containing at least one heteroatom, in which at least one ring is aromatic. Polycyclic heteroaryl rings must contain at least one heteroatom, but not all rings of a polycyclic heteroaryl moiety must contain heteroatoms. Each heteroatom is independently selected from nitrogen, which can be oxidized (e.g., N(O)) or quaternized, oxygen and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring may be at either a carbon atom or a heteroatom. Heteroaryl groups included in compounds described herein may be optionally substituted with one or more substituents. As used herein, the term "($C_5$) heteroaryl" means an heteroaromatic ring of 5 members, wherein at least one carbon atom of the ring is replaced with a heteroatom, such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like. As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$) heteroaryls include pyridyl, pyridazinyl, pyrazinyl, triazinyl, tetrazinyl, and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl, and the like. Heteroaralkyl groups included in compounds described herein may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include are those substituents which form a stable compound described herein without significantly adversely affecting the reactivity or biological activity of the compound described herein. Examples of substituents for an alkyl, alkylene, alkenyl, alkynyl, cycloalkyl, cycloalkenyl, heterocyclyl, aryl, aralkyl, heteroaryl, and heteroaralkyl include an alkyl, alkenyl, alkynyl, cycloalkyl, cycloalkenyl, heterocyclyl, aryl, heteroaryl, aralkyl, heteralkyl, heteroalkyl, alkoxy, (each of which can be optionally and independently substituted), —C(O)NR$^{28}$R$^{29}$, —C(S) NR$^{28}$R$^{29}$, —C(NR$^{32}$)NR$^{28}$R$^{29}$, —NR$^{33}$C(O)R$^{31}$, —NR$^{33}$C (S)R$^{31}$, —NR$^{33}$C(NR$^{32}$)R$^{31}$, halo, —OR$^{33}$, cyano, nitro, —C(O)R$^{33}$, —C(S)R$^{33}$, —C(NR$^{32}$)R$^{33}$, —NR$^{28}$R$^{29}$, —C(O)OR$^{33}$, —C(S)OR$^{33}$, —C(NR$^{32}$)OR$^{33}$, —OC(O)R$^{33}$, —OC(S)R$^{33}$, —OC(NR$^{32}$)R$^{33}$, —NR$^{30}$C(O)NR$^{28}$R$^{29}$, —NR$^{33}$C(S)NR$^{28}$R$^{29}$, —NR$^{33}$C(NR$^{32}$)NR$^{28}$R$^{29}$, —OC(O) NR$^{28}$R$^{29}$, —OC(S)NR$^{28}$R$^{29}$, —OC(NR$^{32}$)NR$^{28}$R$^{29}$, —NR$^{33}$C(O)OR$^{31}$, —NR$^{33}$C(S)OR$^{31}$, —NR$^{33}$C(NR$^{32}$) OR$^{31}$, —S(O)$_k$R$^{33}$, —OS(O)$_k$R$^{33}$, —NR$^{33}$S(O)$_k$R$^{33}$, —S(O)$_k$NR$^{28}$R$^{29}$, —OS(O)$_k$NR$^{28}$R$^{29}$, —NR$^{33}$S(O)$_k$NR$^{28}$R$^{29}$, guanadino, —C(O)SR$^{31}$, —C(S) SR$^{31}$, —C(NR$^{32}$)SR$^{31}$, —OC(O)OR$^{31}$, —OC(S)OR$^{31}$, —OC(NR$^{32}$)OR$^{31}$, —SC(O)R$^{33}$, —SC(O)OR$^{31}$, —SC (NR$^{32}$)OR$^{31}$, —SC(S)R$^{33}$—SC(S)OR$^{31}$, —SC(O)NR$^{28}$R$^{29}$, —SC(NR$^{32}$)NR$^{28}$R$^{29}$, —SC(S)NR$^{28}$R$^{29}$, —SC(NR$^{32}$)R$^{33}$, —OS(O)$_k$OR$^{31}$, —S(O)$_k$OR$^{31}$, —NR$^{30}$S(O)$_k$OR$^{31}$, —SS(O)$_k$R$^{33}$, —SS(O)$_k$OR$^{31}$, —SS(O)$_k$NR$^{28}$R$^{29}$, —OP(O)(OR$^{31}$)$_2$, or —SP(O)(OR$^{31}$)$_2$. In addition, any saturated portion of an alkyl, cycloalkyl, alkylene, heterocyclyl, alkenyl, cycloalkenyl, alkynyl, aralkyl and heteroaralkyl groups, may also be substituted with =O, =S, or =N—R$^{32}$. Each R$^{28}$ and R$^{29}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, or heteroalkyl represented by R$^{28}$ or R$^{29}$ is optionally and independently substituted. Each R$^{30}$, R$^{31}$ and R$^{33}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl represented by R$^{30}$ or R$^{31}$ or R$^{33}$ is optionally and independently unsubstituted. Each R$^{32}$ is independently H, alkyl, alkenyl, alkynyl, cycloalkyl, cycloalkenyl, heterocyclyl, aryl, heteroaryl, aralkyl, heteraralkyl, —C(O)R$^{33}$, —C(O)NR$^{28}$R$^{29}$, —S(O)$_k$R$^{33}$, or —S(O)$_k$NR$^{28}$R$^{29}$, wherein each alkyl, alkenyl, alkynyl, cycloalkyl, cycloalkenyl, heterocyclyl, aryl, heteroaryl, aralkyl and heteraralkyl represented by R$^{32}$ is optionally and independently substituted. The variable k is 0, 1 or 2. In some embodiments, suitable substituents include C1-C4 alkyl, C1-C4 haloalkyl, C1-C4 alkoxy, C1-C4 haloalkoxy, C1-C4 hydroxyalkyl, halo, or hydroxyl.

When a heterocyclyl, heteroaryl or heteroaralkyl group contains a nitrogen atom, it may be substituted or unsubstituted. When a nitrogen atom in the aromatic ring of a heteroaryl group has a substituent, the nitrogen may be oxidized or a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In another embodiment, the subject is a human.

Unless indicated otherwise, the compounds described herein containing reactive functional groups, such as, for example, carboxy, hydroxy, thiol and amino moieties, also include corresponding protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. GREENE, PROTECTING GROUPS IN ORGANIC SYNTHESIS, (John Wiley & Sons, Inc., 1981).

As used herein, the term "compound(s) described herein" or similar terms refers to a compound of formulae (I), or (Ia) or a compound in Tables 1 or 2 or a tautomer or pharmaceutically acceptable salt thereof. Also included in the scope of the embodiments are a solvate, clathrate, hydrate, polymorph, prodrug, or protected derivative of a compound of formulae (I), or (Ia), or a compound in Tables 1 or 2.

The compounds described herein may contain one or more chiral centers and/or double bonds and, therefore, exist as stereoisomers, such as double-bond isomers (i.e., geometric isomers), enantiomers or diastereomers. Each chemical structure shown herein, including the compounds described herein, encompass all of the corresponding compound' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds described herein are preferred.

When a disclosed compound is named or depicted by structure, it is to be understood that solvates (e.g., hydrates) of the compound or a pharmaceutically acceptable salt thereof is also included. "Solvates" refer to crystalline forms wherein solvent molecules are incorporated into the crystal lattice during crystallization. Solvates may include water or non-aqueous solvents such as ethanol, isopropanol, DMSO, acetic acid, ethanolamine and ethyl acetate. When water is the solvent molecule incorporated into the crystal lattice of a solvate, it is typically referred to as a "hydrate". Hydrates include stoichiometric hydrates as well as compositions containing variable amounts of water.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e., the capacity to occur in different crystalline forms). These different crystalline forms are typically known as "polymorphs." It is to be understood that when named or depicted by structure, the disclosed compounds and solvates (e.g., hydrates) also include all polymorphs thereof. Polymorphs have the same chemical composition but differ in packing, geometrical arrangement and other descriptive properties of the crystalline solid state. Polymorphs, therefore, may have different physical properties such as shape, density, hardness, deformability, stability and dissolution properties. Polymorphs typically exhibit different melting points, IR spectra and X-ray powder diffraction patterns, which may be used for identification. One of ordinary skill in the art will appreciate that different polymorphs may be produced, for example, by changing or adjusting the conditions used in crystallizing the compound. For example, changes in temperature, pressure or solvent may result in different polymorphs. In addition, one polymorph may spontaneously convert to another polymorph under certain conditions.

When a disclosed compound is named or depicted by structure, it is to be understood that clathrates ("inclusion compounds") of the compound or its pharmaceutically acceptable salt, solvate or polymorph, are also included. "Clathrate" means a compound of the present invention, or a salt thereof, in the form of a crystal lattice that contains spaces (e.g., channels) that have a guest molecule trapped within (e.g., a solvent or water).

As used herein, and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated herein include analogs or derivatives of compounds of formulae (I) or (Ia) or a compound in Tables 1 or 2 that comprise biohydrolyzable moieties such as biohydrolyzable amides, biohydrolyzable esters, biohydrolyzable carbamates, biohydrolyzable carbonates, biohydrolyzable ureides and phosphate analogues. Prodrugs can typically be prepared using well-known methods, such as those described by 1 BURGER'S MEDICINAL CHEMISTRY AND DRUG DISCOVERY, (Manfred E. Wolff Ed., 5$^{th}$ ed. (1995)) 172-178, 949-982.

As used herein, "Hsp90" includes each member of the family of heat shock proteins having a mass of about 90-kiloDaltons. For example, in humans the highly conserved Hsp90 family includes the cytosolic Hsp90α and Hsp90β isoforms, as well as GRP94, which is found in the endoplasmic reticulum, and HSP75/TRAP1, which is found in the mitochondrial matrix.

"Epidermal growth factor receptor" or "EGFR", as used herein, means any epidermal growth factor receptor (EGFR) protein, peptide, or polypeptide having EGFR or EGFR family activity (e.g., Her1, Her2, Her3 and/or Her4), such as encoded by EGFR Genbank Accession Nos. shown in Table I of U.S. patent application Ser. No. 10/923,354, filed on Aug. 20, 2004, or any other EGFR transcript derived from a EGFR gene and/or generated by EGFR translocation. The term "EGFR" is also meant to include other EGFR protein, peptide, or polypeptide derived from EGFR isoforms (e.g., Her1, Her2, Her3 and/or Her4), mutant EGFR genes, splice variants of EGFR genes, and EGFR gene polymorphisms. EGFR is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor α (TGFα), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or overexpression of EGFR and/or overexpression of its specific ligands. Gullick, Br. Med. Bull. (1991), 47:87-98; Modijtahedi & Dean, Int. J. Oncol. (1994), 4:277-96; Salomon, et al., Crit. Rev. Oncol. Hematol. (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., *Anti-cancer Res.* (1999), 19:221-28; Veale, et al., *Br. J. Cancer* (1993); 68:162-65.

Gliomas are another type of cancer that is characterized by the amplification and/or mutation of the EGFR gene. One of the most common mutations in the EGFR gene is a deletion of exons 2-7 which results in a truncated form of EGFR in which amino acids 6-273 of the extracellular domain are replaced with a single glycine residue. This mutation is called EGFRvIII and is expressed in about half of all glioblastomas. EGFRvIII is unable to bind EGF and TGFα and has constitutive, ligand-independent tyrosine kinase activity. Hsp90 co-purifies with EGFRvIII, indicating that Hsp90 complexes with EGFRvIII. Moreover, the Hsp90 inhibitor geldanamycin, a benzoquinone ansamycin antibiotic, is able to decrease the expression of EGFRvIII, indicating that interaction with Hsp90 is essential to maintain high expression levels of EGFRvIII. Lavictoire, et al., *J. Biological Chem.* (2003), 278(7):5292-5299. These results demonstrate that inhibiting the activity of Hsp90 is an effective strategy for treating cancers that are associated with inappropriate EGFR activity.

An "EGFR inhibitor", as used herein, includes any compound that disrupts EGFR production within a cell. Activation of EGFR leads to the Ras signaling cascade that results in uncontrolled cell proliferation. EGFR inhibitors include monoclonal antibodies that bind EGFR to inactivate it, and compounds that bind to the tyrosine kinase domain of EGFR to inhibit it. EGFR inhibitors include drugs such as erlotinib, gefitinib, and cetuximab. Particularly, erlotinib is described in U.S. Pat. Nos. 5,747,498, 6,900,221, 7,087,613, and RE41065. In addition, the EGFR inhibitors employed herein may also be called other names such as Tarceva®, Iressa®, and Erbitux®, which are all well-known anti-cancer drugs. A more detailed description of some of these drugs is presented below.

Gefitinib, a chemotherapeutic agent that inhibits the activity of EGFR, has been found to be highly efficacious in a subset of lung cancer patients that have mutations in the tyrosine kinase domain of EGFR. In the presence of EGF, these mutants displayed two to three times higher activity than wild type EGFR. In addition, wild type EGFR was internalized by the cells and down-regulated after 15 minutes, whereas mutant EGFR was internalized more slowly and continued to be activated for up to three hours. Lynch, et al., New Eng. J. Med. (2006), 350:2129-2139.

Another chemotherapeutic agent that inhibits EGFR is erlotinib (Tarceva®). Erlotinib is approved for advanced unresectable or metastatic pancreatic cancer and metastatic non-small cell lung cancer. In addition to being a potent EGFR inhibitor, erlotinib also potently inhibits the JAK2 mutant JAK2V617F, which is found in many myeloproliferative disorders, such as polycythemia vera.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis and desmoid tumors. Non-cancerous proliferative disorders also include hyperproliferation of cells in the skin such as psoriasis and its varied clinical forms, Reiter's syndrome, pityriasis rubra pilaris, hyperproliferative variants of disorders of keratinization (e.g., actinic keratosis, senile keratosis), scleroderma, and the like. In one embodiment, the proliferative disorder is a myeloproliferative disorder. In one aspect, the myeloproliferative disorder is polycythemia vera, idiopathic myelofibrosis, myelodysplastic syndrome, psoriasis or essential thrombocythemia. In one embodiment, the proliferative disorder expresses JAK2V617F mutation of JAK2. In an aspect of this embodiment, the proliferative disorder is polycythemia vera, idiopathic myelofibrosis, or essential thrombocythemia. In one aspect, the proliferative disorder is polycythemia vera.

As used herein, the term "pharmaceutically acceptable salt" refers to a salt prepared from a compound of formulae (I) or (Ia) or a compound in Tables 1 or 2 having an acidic functional group, such as a carboxylic acid functional group, and a pharmaceutically acceptable inorganic or organic base. Suitable bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formulae (I) or (Ia) or a compound in Tables 1 or 2 having a basic functional group, such as an amine functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

As used herein, the term "pharmaceutically acceptable solvate," is a solvate formed from the association of one or more pharmaceutically acceptable solvent molecules to one of the compounds of formulae (I) or (Ia) or a compound in Tables 1 or 2. The term "solvate" includes hydrates, e.g., hemihydrate, monohydrate, dihydrate, trihydrate, tetrahydrate, and the like.

A pharmaceutically acceptable carrier may contain inert ingredients which do not unduly inhibit the biological activity of the compound(s). The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., 17$^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

As used herein, the term "effective amount" refers to an amount of a compound described herein which is sufficient to reduce or ameliorate the severity, duration, progression, or onset of a disease or disorder, delay onset of a disease or disorder, retard or halt the advancement of a disease or disorder, cause the regression of a disease or disorder, prevent or delay the recurrence, development, onset or progression of a symptom associated with a disease or disorder, or enhance or improve the therapeutic effect(s) of another therapy. In one embodiment, the disease or disorder is a proliferative disorder. The precise amount of compound administered to a subject will depend on the mode of administration, the type and severity of the disease or condition and on the characteristics of the subject, such as general health, age, sex, body weight and tolerance to drugs. For example, for a proliferative disease or disorder, determination of an effective amount will also depend on the degree, severity and type of cell proliferation. The skilled artisan will be able to determine appropriate dosages depending on these and other factors. When co-administered with other therapeutic agents, e.g., when co-administered with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used. In cases where no amount is expressly noted, an effective amount should be assumed. Non-limiting examples of an effective amount of a compound described herein are provided herein below. In a specific embodiment, the invention provides a method of treating, managing, or ameliorating a disease or disorder, e.g. a proliferative disorder, or one or more symptoms thereof, said method comprising administering to a subject in need thereof a dose of the Hsp90 inhibitor at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, once every 2 days, once every 3 days, once every 4 days, once every 5 days, once every 6 days, once every 7 days, once every 8 days, once every 10 days, once every two weeks, once every three weeks, or once a month.

The dosage of an individual EGFR inhibitor used in combination therapy may be equal to or lower than the dose of an individual therapeutic agent when given independently to treat, manage, or ameliorate a disease or disorder, or one or more symptoms thereof. In one embodiment, the disease or disorder being treated with a combination therapy is a proliferative disorder. In another embodiment, the proliferative disorder is cancer. The recommended dosages of therapeutic agents currently used for the treatment, management, or amelioration of a disease or disorder, or one or more symptoms thereof, can obtained from any reference in the art. See, e.g., GOODMAN & GILMAN'S THE PHARMACOLOGICAL BASIS OF BASIS OF THERAPEUTICS $9^{TH}$ (Hardman, et al., Eds., NY: Mc-Graw-Hill (1996)); PHYSICIAN'S DESK REFERENCE $57^{TH}$ ED. (Medical Economics Co., Inc., Montvale, N.J. (2003)).

As used herein, the terms "treat", "treatment" and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder. In one embodiment, the disease or disorder being treated is a proliferative disorder such as cancer. In specific embodiments, the terms "treat", "treatment" and "treating" refer to the amelioration of at least one measurable physical parameter of a disease or disorder, such as growth of a tumor, not necessarily discernible by the patient. In other embodiments the terms "treat", "treatment" and "treating" refer to the inhibition of the progression of a disease or disorder, e.g., a proliferative disorder, either physically by the stabilization of a discernible symptom, physiologically by the stabilization of a physical parameter, or both. In another embodiment, the terms "treat", "treatment" and "treating" of a proliferative disease or disorder refers to the reduction or stabilization of tumor size or cancerous cell count, and/or delay of tumor formation. In another embodiment, the terms "treat", "treating" and "treatment" also encompass the administration of a compound described herein as a prophylactic measure to patients with a predisposition (genetic or environmental) to any disease or disorder described herein.

As used herein, the terms "therapeutic agent" and "therapeutic agents" refer to any agent(s) that can be used in the treatment of a disease or disorder, e.g. a proliferative disorder, or one or more symptoms thereof. In certain embodiments, the term "therapeutic agent" refers to a compound described herein. In certain other embodiments, the term "therapeutic agent" does not refer to a compound described herein. Preferably, a therapeutic agent is an agent that is known to be useful for, or has been or is currently being used for the treatment of a disease or disorder, e.g., a proliferative disorder, or one or more symptoms thereof.

As used herein, the term "synergistic" refers to a combination of a compound described herein and another therapeutic agent, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of said agent(s) to a subject with a disease or disorder, e.g., a proliferative disorder. The ability to utilize lower the dosage of one or more therapeutic agent and/or to administer said therapeutic agent less frequently reduces the toxicity associated with the administration of said agent to a subject without reducing the efficacy of said therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone.

As used herein, the phrase "side effects" encompasses unwanted and adverse effects of a therapeutic agent. Side effects are always unwanted, but unwanted effects are not necessarily adverse. An adverse effect from a therapeutic agent might be harmful or uncomfortable or risky to a subject. Side effects include fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapeutic agent. The use of the term "in combination" does not restrict the order in which said therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer. In one embodiment, the Hsp90 inhibitor and the EGFR inhibitor are dosed on independent schedules. In another embodiment, the Hsp90 inhibitor and the EGFR inhibitor are dosed on approximately the same schedule. In another embodiment, the Hsp90 inhibitor and the EGFR inhibitor are dosed concurrently or sequentially on the same day.

As used herein, the terms "therapies" and "therapy" can refer to any protocol(s), method(s), and/or agent(s) that can be used in the prevention, treatment, management, or amelioration of a disease or disorder, e.g., a proliferative disorder, or one or more symptoms thereof.

A used herein, a "protocol" includes dosing schedules and dosing regimens. The protocols herein are methods of use and include therapeutic protocols.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a racemic mixture means about 50% of one enantiomer and about 50% of is corresponding enantiomer of the molecule. The combination encompasses all enantiomerically-pure, enantiomerically-enriched, diastereomerically pure, diastereomerically enriched, and racemic mixtures of the compounds described herein. Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds described herein are defined by their chemical structures and/or chemical names. Where a compound is referred to by both a chemical structure and a chemical name, and the chemical structure and the chemical name conflict, the chemical structure is determinative of the compound's identity.

When administered to a subject (e.g., a non-human animal for veterinary use or for improvement of livestock or to a human for clinical use), the compounds described herein are administered in an isolated form, or as the isolated form in a pharmaceutical composition. As used herein, "isolated" means that the compounds described herein are separated from other components of either: (a) a natural source, such as a plant or cell, preferably bacterial culture, or (b) a synthetic organic chemical reaction mixture. Preferably, the compounds of the invention are purified via conventional techniques. As used herein, "purified" means that when isolated, the isolate contains at least 95%, preferably at least 98%, of a compound described herein by weight of the isolate either as a mixture of stereoisomers, or as a diastereomeric or enantiomeric pure isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

The methods described herein utilize triazolone Hsp90 inhibitory compounds listed in Tables 1 or 2, or a compound represented by Formulae (I) or (Ia):

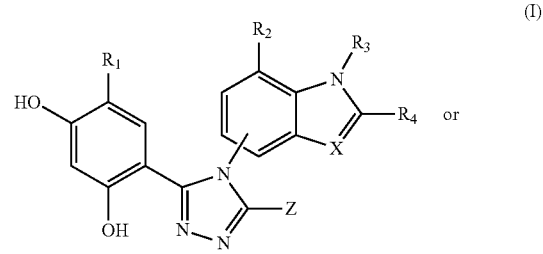

(I)

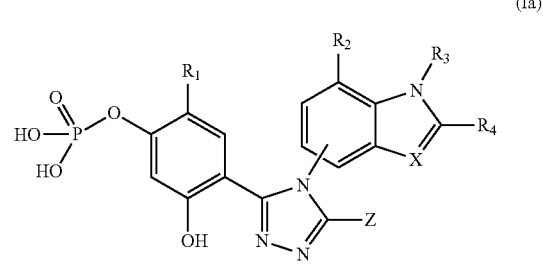

(Ia)

or a tautomer, or a pharmaceutically acceptable salt thereof, wherein:

Z is OH, SH, or $NH_2$;

X is $CR_4$ or N;

$R_1$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —C(O)

$SR_7$, $-C(S)SR_7$, $-C(S)OR_7$, $-C(S)NR_{10}R_{11}$, $-C(NR_8)OR_7$, $-C(NR_8)R_7$, $-C(NR_8)NR_{10}R_{11}$, $-C(NR_8)SR_7$, $-OC(O)R_7$, $-OC(O)OR_7$, $-OC(S)OR_7$, $-OC(NR_8)OR_7$, $-SC(O)R_7$, $-SC(O)OR_7$, $-SC(NR_8)OR_7$, $-OC(S)R_7$, $-SC(S)R_7$, $-SC(S)OR_7$, $-OC(O)NR_{10}R_{11}$, $-OC(S)NR_{10}R_{11}$, $-OC(NR_8)NR_{10}R_{11}$, $-SC(O)NR_{10}R_{11}$, $-SC(NR_8)NR_{10}R_{11}$, $-SC(S)NR_{10}R_{11}$, $-OC(NR_8)R_7$, $-SC(NR_8)R_7$, $-C(O)NR_{10}R_{11}$, $-NR_8C(O)R_7$, $-NR_7C(S)R_7$, $-NR_7C(S)OR_7$, $-NR_7C(NR_8)R_7$, $-NR_7C(O)OR_7$, $-NR_7C(NR_8)OR_7$, $-NR_7C(O)NR_{10}R_{11}$, $-NR_7C(S)NR_{10}R_{11}$, $-NR_7C(NR_8)NR_{10}R_{11}$, $-SR_7$, $-S(O)_pR_7$, $-OS(O)_pR_7$, $-OS(O)_pOR_7$, $-OS(O)_pNR_{10}R_{11}$, $-S(O)_pOR_7$, $-NR_8S(O)_pR_7$, $-NR_7S(O)_pNR_{10}R_{11}$, $-NR_7S(O)_pOR_7$, $-S(O)_pNR_{10}R_{11}$, $-SS(O)_pR_7$, $-SS(O)_pOR_7$, $-SS(O)_pNR_{10}R_{11}$, $-OP(O)(OR_7)_2$, or $-SP(O)(OR_7)_2$;

$R_2$ is $-H$, $-OH$, $-SH$, $-NR_7H$, $-OR_{15}$, $-SR_{15}$, $-NHR_{15}$, $-O(CH_2)_mOH$, $-O(CH_2)_mSH$, $-O(CH_2)_mNR_7H$, $-S(CH_2)_mOH$, $-S(CH_2)_mSH$, $-S(CH_2)_mNR_7H$, $-OC(O)NR_{10}R_{11}$, $-SC(O)NR_{10}R_{11}$, $-NR_7C(O)NR_{10}R_{11}$, $-OC(O)R_7$, $-SC(O)R_7$, $-NR_7C(O)R_7$, $-OC(O)OR_7$, $-SC(O)OR_7$, $-NR_7C(O)OR_7$, $-OCH_2C(O)R_7$, $-SCH_2C(O)R_7$, $-NR_7CH_2C(O)R_7$, $-OCH_2C(O)OR_7$, $-SCH_2C(O)OR_7$, $-NR_7CH_2C(O)OR_7$, $-OCH_2C(O)NR_{10}R_{11}$, $-SCH_2C(O)NR_{10}R_{11}$, $-NR_7CH_2C(O)NR_{10}R_{11}$, $-OS(O)_pR_7$, $-SS(O)_pR_7$, $-NR_7S(O)_pR_7$, $-OS(O)_pNR_{10}R_{11}$, $-SS(O)_pNR_{10}R_{11}$, $-NR_7S(O)_pNR_{10}R_{11}$, $-OS(O)_pOR_7$, $-SS(O)_pOR_7$, $-NR_7S(O)_pOR_7$, $-OC(S)R_7$, $-SC(S)R_7$, $-NR_7C(S)R_7$, $-OC(S)OR_7$, $-SC(S)OR_7$, $-NR_7C(S)OR_7$, $-OC(S)NR_{10}R_{11}$, $-SC(S)NR_{10}R_{11}$, $-NR_7C(S)NR_{10}R_{11}$, $-OC(NR_8)R_7$, $-SC(NR_8)R_7$, $-NR_7C(NR_8)R_7$, $-OC(NR_8)OR_7$, $-SC(NR_8)OR_7$, $-NR_7C(NR_8)OR_7$, $-OC(NR_8)NR_{10}R_{11}$, $-SC(NR_8)NR_{10}R_{11}$, or $-NR_7C(NR_8)NR_{10}R_{11}$;

$R_3$ is $-H$, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, $-C(O)R_7$, $-(CH_2)_mC(O)OR_7$, $-C(O)OR_7$, $-OC(O)R_7$, $-C(O)NR_{10}R_{11}$, $-S(O)_pR_7$, $-S(O)_pOR_7$, or $-S(O)_pNR_{10}R_{11}$;

$R_4$ is $-H$, $-OH$, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_7$ and $R_8$, for each occurrence, are, independently, $-H$, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently $-H$, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{15}$, for each occurrence, is independently, a lower alkyl;

p, for each occurrence, is, independently, 1 or 2; and m, for each occurrence, is independently, 1, 2, 3, or 4.

In one embodiment, in formula (I) or (Ia), X is $CR_4$.

In another embodiment, in formula (I) or (Ia), X is N.

In another embodiment, in formula (I) or (Ia), $R_1$ is selected from the group consisting of $-H$, lower alkyl, lower alkoxy, lower cycloalkyl, and lower cycloalkoxy.

In another embodiment, in formula (I) or (Ia), $R_1$ is selected from the group consisting of $-H$, methyl, ethyl, propyl, isopropyl, cyclopropyl, methoxy, ethoxy, propoxy, and cyclopropoxy.

In another embodiment, in formula (I) or (Ia), $R_3$ is selected from the group consisting of H, a lower alkyl, a lower cycloalkyl, $-C(O)N(R_{27})_2$, and $-C(O)OH$, wherein $R_{27}$ is $-H$ or a lower alkyl.

In another embodiment, in formula (I) or (Ia), $R_3$ is selected from the group consisting of $-H$, methyl, ethyl, n-propyl, isopropyl, cyclopropyl, n-butyl, sec-butyl, tert-butyl, n-pentyl, n-hexyl, $-C(O)OH$, $-(CH_2)_mC(O)OH$, $-CH_2OCH_3$, $-CH_2CH_2OCH_3$, and $-C(O)N(CH_3)_2$.

In one embodiment, $R_4$ is H or a lower alkyl.

In another embodiment, in formula (I) or (Ia), $R_4$ is selected from the group consisting of $-H$, methyl, ethyl, propyl, isopropyl or cyclopropyl.

In another embodiment, in formula (I) or (Ia), $R_1$ is selected from the group consisting of $-H$, $-OH$, $-SH$, $-NH_2$, a lower alkoxy and a lower alkyl amino.

In another embodiment, in formula (I) or (Ia), $R_1$ is selected from the group consisting of $-H$, $-OH$, methoxy and ethoxy.

In another embodiment, in formula (I) or (Ia), Z is $-OH$.

In another embodiment, in formula (I) or (Ia), Z is SH.

In another embodiment, in formula (I) or (Ia), $R_2$ is selected from the group consisting of $-H$, $-OH$, $-SH$, $-NH_2$, a lower alkoxy and a lower alkyl amino.

In another embodiment, in formula (I) or (Ia), $R_2$ is selected from the group consisting of $-H$, $-OH$, methoxy, and ethoxy.

In another embodiment, in formula (I) or (Ia), $R_1$ is selected from the group consisting of $-H$, methyl, ethyl, propyl, isopropyl, cyclopropyl, methoxy, ethoxy, propoxy, and cyclopropoxy; $R_3$ is selected from the group consisting of $-H$, methyl, ethyl, n-propyl, isopropyl, cyclopropyl, n-butyl, sec-butyl, tert-butyl, n-pentyl, n-hexyl, $-C(O)OH$, $-(CH_2)_mC(O)OH$, $-CH_2OCH_3$, $-CH_2CH_2OCH_3$, and $-C(O)N(CH_3)_2$; $R_4$ is selected from the group consisting of $-H$, methyl, ethyl, propyl, isopropyl or cyclopropyl; $R_2$ is selected from the group consisting of $-H$, $-OH$, $-SH$, $-NH_2$, a lower alkoxy and a lower alkyl amino; and Z is OH.

In another embodiment, in formula (I) or (Ia), $R_1$ is selected from the group consisting of $-H$, methyl, ethyl, propyl, isopropyl, cyclopropyl, methoxy, ethoxy, propoxy, and cyclopropoxy; $R_3$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C (O)OH, —CH$_2$OCH$_3$, —CH$_2$CH$_2$OCH$_3$, and —C(O)N (CH$_3$)$_2$; $R_4$ is selected from the group consisting of —H, methyl, ethyl, propyl, isopropyl or cyclopropyl; $R_2$ is selected from the group consisting of —H, —OH, —SH, —NH$_2$, a lower alkoxy and a lower alkyl amino; and Z is SH.

In another embodiment, the compound is selected from the group consisting of:

3-(2,4-dihydroxy-5-ethyl-phenyl)-4-(1,3-dimethyl-indol-5-yl)-5-hydroxy-[1,2,4]triazole,
3-(2,4-dihydroxy-5-isopropyl-phenyl)-4-(1,3-dimethyl-indol-5-yl)-5-hydroxy-[1,2,4]triazole,
3-(2,4-dihydroxy-5-isopropyl-phenyl)-4-(1-methyl-indol-5-yl)-5-hydroxy-[1,2,4]triazole,
3-(2,4-dihydroxy-5-isopropyl-phenyl)-4-(1-isopropyl-indol-4-yl)-5-hydroxy-[1,2,4]triazole,
3-(2,4-dihydroxy-5-isopropyl-phenyl)-4-(1-methyl-indazol-5-yl)-5-mercapto-[1,2,4]triazole,
3-(2,4-dihydroxy-5-isopropyl-phenyl)-4-(1-methyl-indazol-6-yl)-5-mercapto-[1,2,4]triazole,
3-(2,4-dihydroxyphenyl)-4-(1-ethyl-indol-4-yl)-5-mercapto-[1,2,4]triazole,
3-(2,4-dihydroxyphenyl)-4-(1-isopropyl-indol-4-yl)-5-mercapto-[1,2,4]triazole,
3-(2,4-dihydroxyphenyl)-4-(indol-4-yl)-5-mercapto-[1,2,4]triazole,
3-(2,4-dihydroxyphenyl)-4-(1-methoxyethyl-indol-4-yl)-5-mercapto-[1,2,4]triazole,
3-(2,4-dihydroxy-5-ethyl-phenyl)-4-(1-isopropyl-indol-4-yl)-5-mercapto-[1,2,4]triazole,
3-(2,4-dihydroxyphenyl)-4-(1-dimethylcarbamoyl-indol-4-yl)-5-mercapto-[1,2,4]triazole,
3-(2,4-dihydroxy-5-ethyl-phenyl)-4-(1-propyl-indol-4-yl)-5-mercapto-[1,2,4]triazole,
3-(2,4-dihydroxy-5-ethyl-phenyl)-4-(1,2,3-trimethyl-indol-5-yl)-5-mercapto-[1,2,4]triazole,
3-(2,4-dihydroxy-5-ethyl-phenyl)-4-(2,3-dimethyl-indol-5-yl)-5-mercapto-[1,2,4]triazole,
3-(2,4-dihydroxy-5-ethyl-phenyl)-4-(1-acetyl-2,3-dimethyl-indol-5-yl)-5-mercapto-[1,2,4]triazole,
3-(2,4-dihydroxy-5-ethyl-phenyl)-4-(1-propyl-2,3-dimethyl-indol-5-yl)-5-mercapto-[1,2,4]triazole,
3-(2,4-dihydroxy-5-ethyl-phenyl)-4-(1-n-butyl-indol-4-yl)-5-mercapto-[1,2,4]triazole,
3-(2,4-dihydroxy-5-ethyl-phenyl)-4-(1-n-pentyl-indol-4-yl)-5-mercapto-[1,2,4]triazole,
3-(2,4-dihydroxy-5-ethyl-phenyl)-4-(1-n-hexyl-indol-4-yl)-5-mercapto-[1,2,4]triazole,
3-(2,4-dihydroxy-5-cyclopropyl-phenyl)-4-(1-(1-methylcyclopropyl)-indol-4-yl)-5-mercapto-[1,2,4]triazole,
3-(2,4-dihydroxy-5-cyclopropyl-phenyl)-4-(1,2,3-trimethyl-indol-5-yl)-5-mercapto-[1,2,4]triazole,
3-(2,4-dihydroxy-5-ethyl-phenyl)-4-(1-methyl-3-ethyl-indol-5-yl)-5-mercapto-[1,2,4]triazole,
3-(2,4-dihydroxy-5-ethyl-phenyl)-4-(1,3-dimethyl-indol-5-yl)-5-mercapto-[1,2,4]triazole,
3-(2,4-dihydroxy-5-ethyl-phenyl)-4-(1-methyl-3-isopropyl-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-ethyl-phenyl)-4-(N-methyl-indol-5-yl)-5-mercapto-[1,2,4]triazole,
3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole,
3-(2,4-dihydroxy-5-isopropyl-phenyl)-4-(1-propyl-indol-5-yl)-5-mercapto-[1,2,4]triazole, or a tautomer, or a pharmaceutically acceptable salt thereof.

In another embodiment, the compound is selected from the group consisting of 3-(2,4-dihydroxy-5-ethyl-phenyl)-4-(1-ethyl-benzimidazol-4-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole HCL salt,
3-(2,4-dihydroxy-5-ethyl-phenyl)-4-(2-methyl-3-ethyl-benzimidazol-5-yl)-5-mercapto-[1,2,4]triazole,
3-(2,4-dihydroxy-5-ethyl-phenyl)-4-(1-ethyl-2-methyl-benzimidazol-5-yl)-5-mercapto-[1,2,4]triazole,
3-(2,4-dihydroxy-5-isopropyl-phenyl)-4-(1-methyl-2-trifluoromethyl-benzimidazol-5-yl)-5-mercapto-[1,2,4]triazole, or a tautomer, or a pharmaceutically acceptable salt thereof.

In another embodiment, the compound is selected from the group consisting of 5-hydroxy-4-(5-hydroxy-4-(1-methyl-1H-indol-5-yl)-4H-1,2,4-triazol-3-yl)-2-isopropylphenyl dihydrogen phosphate,
sodium 5-hydroxy-4-(5-hydroxy-4-(1-methyl-1H-indol-5-yl)-4H-1,2,4-triazol-3-yl)-2-isopropylphenyl phosphate,
2-(3,4-dimethoxyphenethyl)-5-hydroxy-4-(5-hydroxy-4-(1-methyl-1H-indol-5-yl)-4H-1,2,4-triazol-3-yl)phenyl dihydrogen phosphate,
5-hydroxy-2-isopropyl-4-(5-mercapto-4-(4-methoxybenzyl)-4H-1,2,4-triazol-3-yl)phenyl dihydrogen phosphate,
5-hydroxy-4-(5-hydroxy-4-(4-methoxybenzyl)-4H-1,2,4-triazol-3-yl)-2-isopropylphenyl dihydrogen phosphate,
4-(4-(1,3-dimethyl-1H-indol-5-yl)-5-hydroxy-4H-1,2,4-triazol-3-yl)-2-ethyl-5-hydroxyphenyl dihydrogen phosphate, or a tautomer, or a pharmaceutically acceptable salt thereof.

Hsp90 inhibitory compounds, as well as tautomers or pharmaceutically acceptable salts thereof, that may be used in the methods described herein are depicted in Tables 1 or 2.

TABLE 1

| | STRUCTURE | TAUTOMERIC STRUCTURE | NAME |
|---|---|---|---|
| 1 | 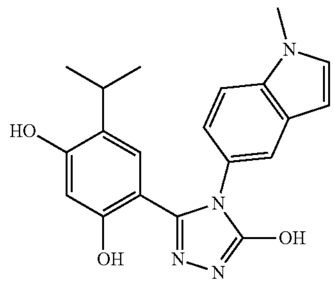 [SMILES: CC(C)c1cc(-c2nnc(O)n2-c2ccc3c(ccn3C)c2)c(O)cc1O] | | 3-(2,4-DIHYDROXY-5-ISOPROPYL-PHENYL)-4-(1-METHYL-INDOL-5-YL)-5-HYDROXY-[1,2,4]TRIAZOLE |
| 2 | 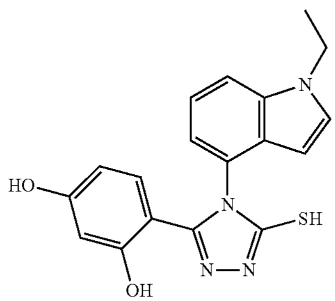 [SMILES: CCn1ccc2c(-n3c(S)nnc3-c3ccc(O)cc3O)cccc21] | | 3-(2,4-DIHYDROXYPHENYL)-4-(1-ETHYL-INDOL-4-YL)-5-MERCAPTO-[1,2,4]TRIAZOLE |
| 3 | 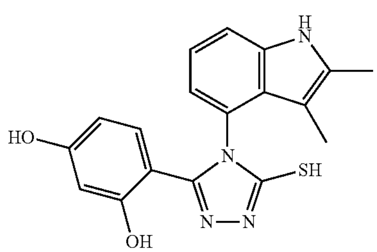 [SMILES: Cc1[nH]c2cccc(-n3c(S)nnc3-c3ccc(O)cc3O)c2c1C] | | 3-(2,4-DIHYDROXY-PHENYL)-4-(2,3-DIMETHYL-1H-INDOL-4-YL)-5-MERCAPTO-[1,2,4]TRIAZOLE |
| 4 | 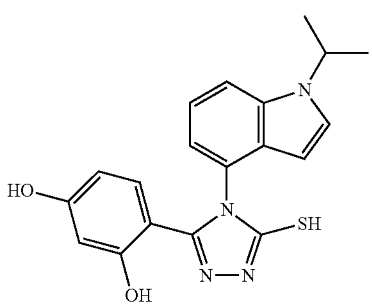 [SMILES: CC(C)n1ccc2c(-n3c(S)nnc3-c3ccc(O)cc3O)cccc21] | | 3-(2,4-DIHYDROXYPHENYL)-4-(1-ISOPROPYL-INDOL-4-YL)-5-MERCAPTO-[1,2,4]TRIAZOLE |
| 5 | 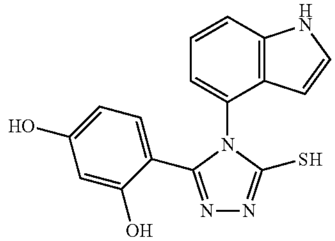 [SMILES: Oc1ccc(-c2nnc(S)n2-c2cccc3[nH]ccc23)c(O)c1] | | 3-(2,4-DIHYDROXY-PHENYL)-4-(INDOL-4-YL)-5-MERCAPTO-[1,2,4]TRIAZOLE |

TABLE 1-continued

| | STRUCTURE | TAUTOMERIC STRUCTURE | NAME |
|---|---|---|---|
| 6 | 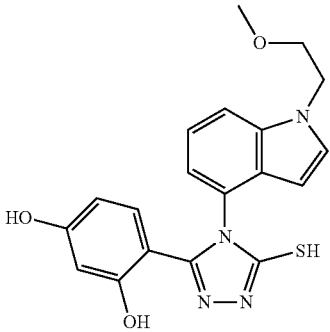 [SMILES: COCCn1ccc2c(-n3c(S)nnc3-c3ccc(O)cc3O)cccc21] | | 3-(2,4-DIHYDROXY-PHENYL)-4-[1-(2-METHOXYETHOXY)-INDOL-4-YL]-5-MERCAPTO-[1,2,4]TRIAZOLE |
| 7 | 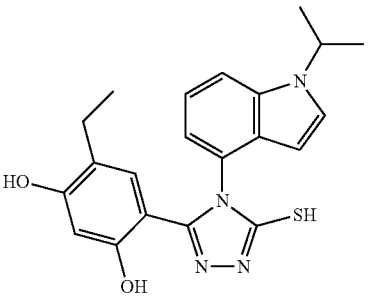 [SMILES: CCc1cc(-c2nnc(S)n2-c2cccc3c2ccn3C(C)C)c(O)cc1O] | | 3-(2,4-DIHYDROXY-5-ETHYL-PHENYL)-4-(1-ISOPROPYL-INDOL-4-YL)-5-MERCAPTO-[1,2,4]TRIAZOLE |
| 8 | 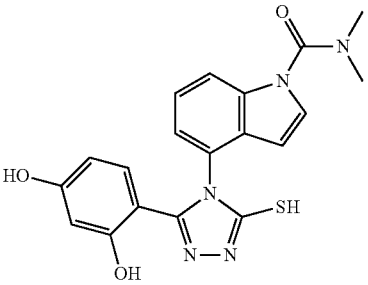 [SMILES: CN(C)C(=O)n1ccc2c(-n3c(S)nnc3-c3ccc(O)cc3O)cccc21] | | 3-(2,4-DIHYDROXY-5-ETHYL-PHENYL)-4-[1-(DIMETHYL-CARBAMOYL)-INDOL-4-YL]-5-MERCAPTO-[1,2,4]TRIAZOLE |
| 9 | 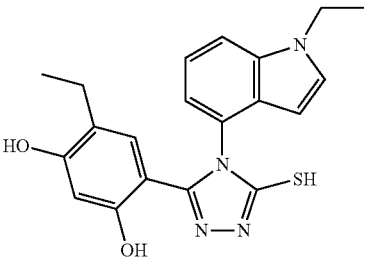 [SMILES: CCc1cc(-c2nnc(S)n2-c2cccc3c2ccn3CC)c(O)cc1O] | | 3-(2,4-DIHYDROXY-5-ETHYL-PHENYL)-4-(1-ETHYL-BENZOIMIDAZOL-4-YL)-5-MERCAPTO-[1,2,4]TRIAZOLE |
| 10 | 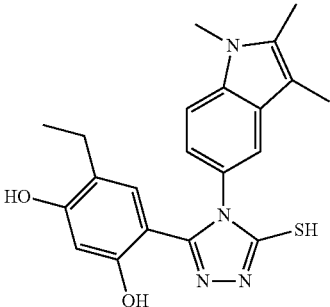 [SMILES: CCc1cc(-c2nnc(S)n2-c2ccc3c(c2)c(C)c(C)n3C)c(O)cc1O] | | 3-(2,4-DIHYDROXY-5-ETHYL-PHENYL)-4-(1,2,3-TRIMETHYL-INDOL-5-YL)-5-MERCAPTO-[1,2,4]TRIAZOLE |

TABLE 1-continued

| | STRUCTURE | TAUTOMERIC STRUCTURE | NAME |
|---|---|---|---|
| 11 | 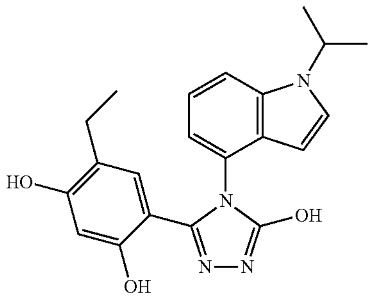 | | 3-(2,4-DIHYDROXY-5-ETHYL-PHENYL)-4-(1-ISOPROPYL-INDOL-3-YL)-5-HYDROXY-[1,2,4]TRIAZOLE |
| 12 | 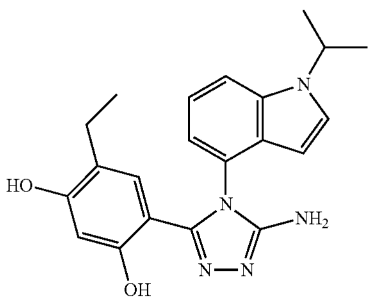 | | 3-(2,4-DIHYDROXY-5-ETHYL-PHENYL)-4-(1-ISOPROPYL-INDOL-4-YL)-5-AMINO-[1,2,4]TRIAZOLE |
| 15 | 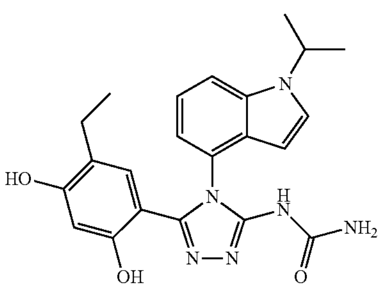 [SMILES: CCc1cc(-c2nnc(NC(N)=O)n2-c2cccc3c2ccn3C(C)C)c(O)cc1O] | | 3-(2,4-DIHYDROXY-5-ETHYL-PHENYL)-4-(1-ISOPROPYL-INDOL-4-YL)-5-UREIDO-[1,2,4]TRIAZOLE |
| 16 | 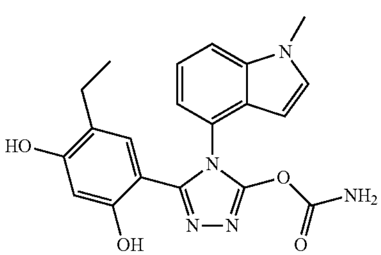 [SMILES: CCc1cc(-c2nnc(OC(N)=O)n2-c2cccc3c2ccn3C)c(O)cc1O] | | 3-(2,4-DIHYDROXY-5-ETHYL-PHENYL)-4-(1-METHYL-INDOL-4-YL)-5-CARBAMOYLOXY-[1,2,4]TRIAZOLE |
| 17 | 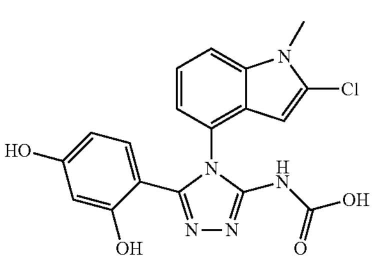 [SMILES: Cn1c(Cl)cc2c(-n3c(NC(=O)O)nnc3-c3ccc(O)cc3O)cccc21] | | 3-(2,4-DIHYDROXY-PHENYL)-4-(1-METHYL-2-CHLORO-INDOL-4-YL)-5-CARBAMOYLOXY-[1,2,4]TRIAZOLE |

TABLE 1-continued

| | STRUCTURE | TAUTOMERIC STRUCTURE | NAME |
|---|---|---|---|
| 18 | 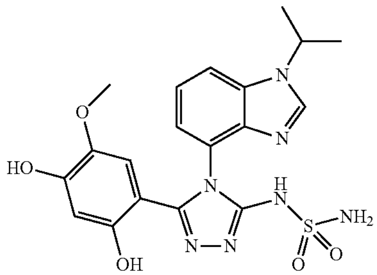 [SMILES: COc1cc(-c2nnc(NS(N)(=O)=O)n2-c2cccc3c2ncn3C(C)C)c(O)cc1O] | | 3-(2,4-DIHYDROXY-5-METHOXY-PHENYL)-4-(1-ISOPROPYL-BENZOIMIDAZOL-4-YL)-5-(SULFAMOYLAMINO)-[1,2,4]TRIAZOLE |
| 20 | 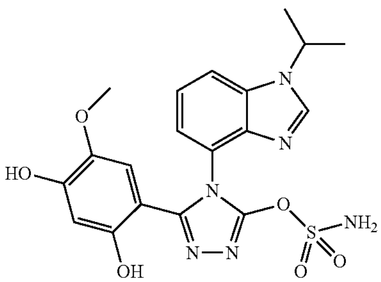 [SMILES: COc1cc(-c2nnc(OS(N)(=O)=O)n2-c2cccc3c2ncn3C(C)C)c(O)cc1O] | | 3-(2,4-DIHYDROXY-5-METHOXY-PHENYL)-4-(1-ISOPROPYL-BENZOIMIDAZOL-4-YL)-5-(SULFAMOYLOXY)-[1,2,4]TRIAZOLE |
| 21 | 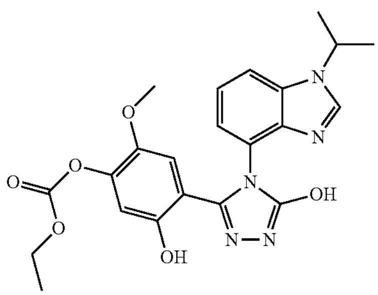 [SMILES: CCOC(=O)Oc1cc(O)c(-c2nnc(O)n2-c2cccc3c2ncn3C(C)C)cc1OC] | | 3-(2-HYDROXY-4-ETHOXYCARBONYOXY-5-METHOXY-PHENYL)-4-(1-ISOPROPYL-BENZOIMIDAZOL-4-YL)-5-HYDROXY-[1,2,4]TRIAZOLE |
| 22 | 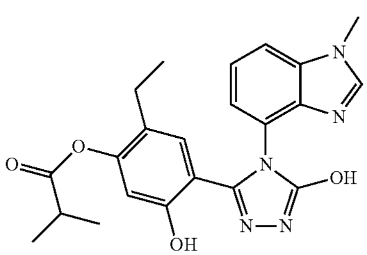 [SMILES: CCc1cc(-c2nnc(O)n2-c2cccc3c2ncn3C)c(O)cc1OC(=O)C(C)C] | | 3-[2-HYDROXY-4-ISOBUTYRYLOXY-5-ETHYL-PHENYL]-4-(1-METHYL-BENZOIMIDAZOL-4-YL)-5-HYDROXY-[1,2,4]TRIAZOLE |
| 23 | 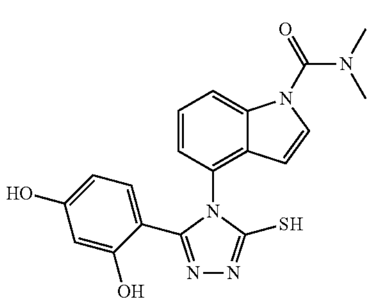 [SMILES: CN(C)C(=O)n1ccc2c(-n3c(S)nnc3-c3ccc(O)cc3O)cccc21] | | 3-(2,4-DIHYDROXY-PHENYL)-4-(1-DIMETHYLCARBAMOYL-INDOL-4-YL)-5-MERCAPTO-[1,2,4]TRIAZOLE |

TABLE 1-continued

| | STRUCTURE | TAUTOMERIC STRUCTURE | NAME |
|---|---|---|---|
| 24 | 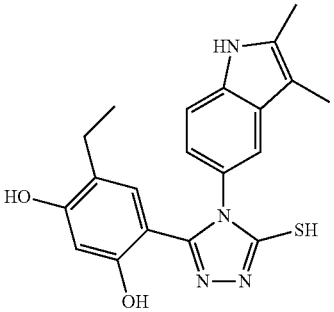 [SMILES: CCc1cc(-c2nnc(S)n2-c2ccc3[nH]c(C)c(C)c3c2)c(O)cc1O] | 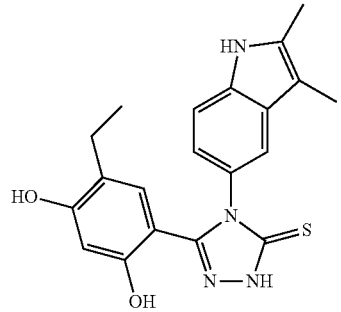 [SMILES: CCc1cc(-c2n[nH]c(=S)n2-c2ccc3[nH]c(C)c(C)c3c2)c(O)cc1O] | 3-(2,4-DIHYDROXY-5-ETHYL-PHENYL)-4-(2,3-DIMETHYL-INDOL-5-YL)-5-MERCAPTO-[1,2,4]TRIAZOLE |
| 25 | 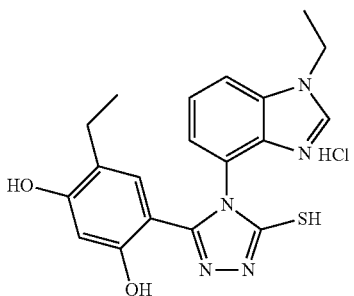 [SMILES: CCc1cc(-c2nnc(S)n2-c2cccc3c2ncn3CC)c(O)cc1O ; Cl] | 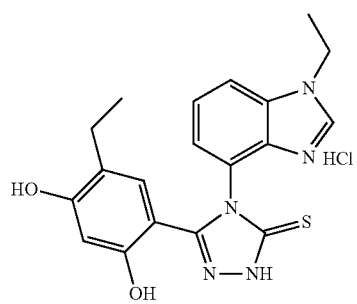 [SMILES: CCc1cc(-c2n[nH]c(=S)n2-c2cccc3c2ncn3CC)c(O)cc1O ; Cl] | 3-(2,4-DIHYDROXY-5-ETHYL-PHENYL)-4-(1-ETHYL-1H-BENZOIMIDAZOL-4-YL)-5-MERCAPTO-[1,2,4]TRIAZOLE, HCL SALT |
| 26 | 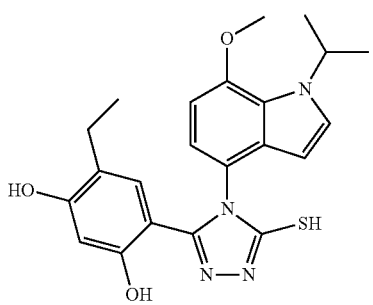 [SMILES: CCc1cc(-c2nnc(S)n2-c2ccc(OC)c3c2ccn3C(C)C)c(O)cc1O] | 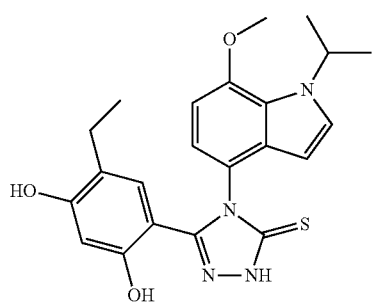 [SMILES: CCc1cc(-c2n[nH]c(=S)n2-c2ccc(OC)c3c2ccn3C(C)C)c(O)cc1O] | 3-(2,4-DIHYDROXY-5-ETHYL-PHENYL)-4-(1-ISOPROPYL-7-METHOXY-INDOL-4-YL)-5-MERCAPTO[1,2,4]TRIAZOLE |
| 27 | 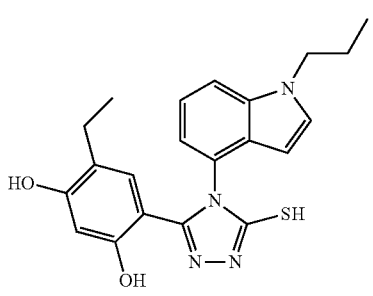 [SMILES: CCCn1ccc2c(-n3c(S)nnc3-c3cc(CC)c(O)cc3O)cccc21] | 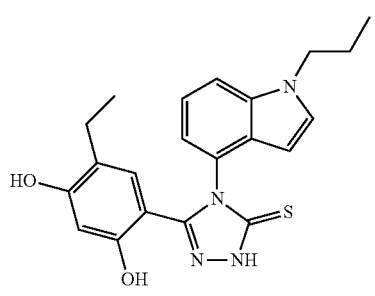 [SMILES: CCCn1ccc2c(-n3c(-c4cc(CC)c(O)cc4O)n[nH]c3=S)cccc21] | 3-(2,4-DIHYDROXY-5-ETHYL-PHENYL)-4-(1-PROPYL-INDOL-4-YL)-5-MERCAPTO-[1,2,4]TRIAZOLE |
| 28 | 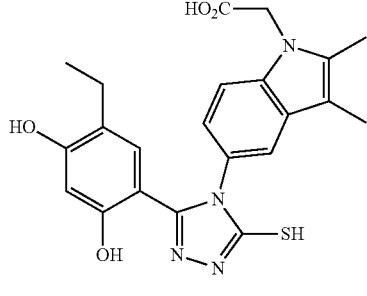 [SMILES: CCc1cc(-c2nnc(S)n2-c2ccc3c(c2)c(C)c(C)n3CC(=O)O)c(O)cc1O] | 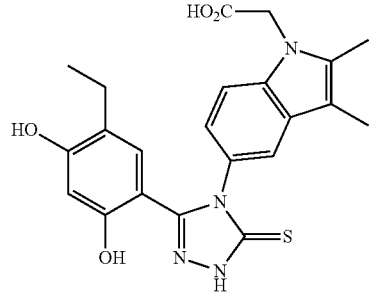 [SMILES: CCc1cc(-c2n[nH]c(=S)n2-c2ccc3c(c2)c(C)c(C)n3CC(=O)O)c(O)cc1O] | 3-(2,4-DIHYDROXY-5-ETHYL-PHENYL)-4-(1-ACETYL-2,3-DIMETHYL-INDOL-5-YL)-5-MERCAPTO-[1,2,4]TRIAZOLE |

TABLE 1-continued

| | STRUCTURE | TAUTOMERIC STRUCTURE | NAME |
|---|---|---|---|
| 29 | 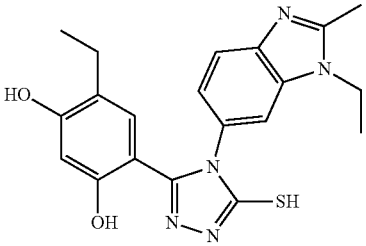 [SMILES: CCc1cc(-c2nnc(S)n2-c2ccc3nc(C)n(CC)c3c2)c(O)cc1O] | 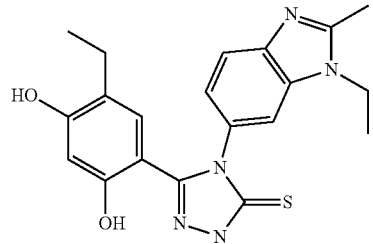 | 3-(2,4-DIHYDROXY-5-ETHYL-PHENYL)-4-(2-METHYL-3-ETHYL-BENZIMIDAZOL-5-YL)-5-MERCAPTO-[1,2,4]TRIAZOLE |
| 30 | 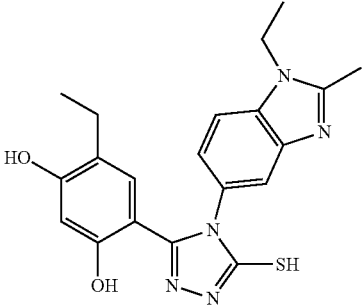 [SMILES: CCc1cc(-c2nnc(S)n2-c2ccc3c(c2)nc(C)n3CC)c(O)cc1O] | 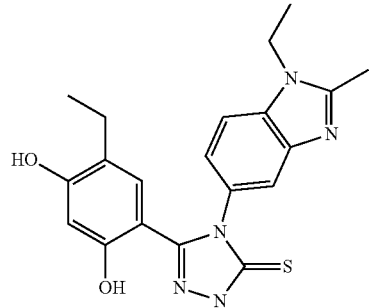 | 3-(2,4-DIHYDROXY-5-ETHYL-PHENYL)-4-(1-ETHYL-2-METHYL-BENZIMIDAZOL-5-YL)-5-MERCAPTO-[1,2,4]TRIAZOLE |
| 31 | 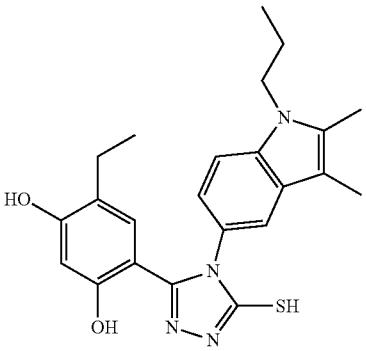 [SMILES: CCCn1c(C)c(C)c2cc(-n3c(S)nnc3-c3cc(CC)c(O)cc3O)ccc21] | 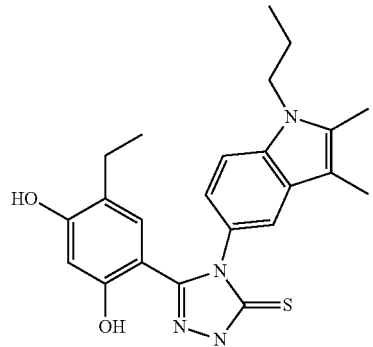 | 3-(2,4-DIHYDROXY-5-ETHYL-PHENYL)-4-(1-PROPYL-2,3-DIMETHYL-INDOL-5-YL)-5-MERCAPTO-[1,2,4]TRIAZOLE |
| 34 | 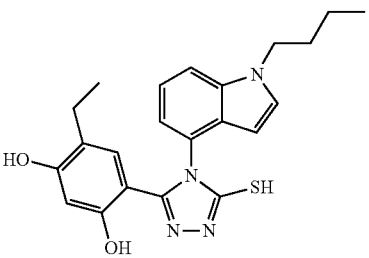 [SMILES: CCCCn1ccc2c(-n3c(S)nnc3-c3cc(CC)c(O)cc3O)cccc21] | 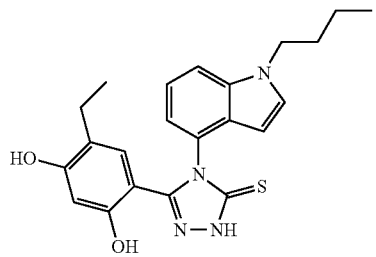 [SMILES: CCCCn1ccc2c(-n3c(-c4cc(CC)c(O)cc4O)n[nH]c3=S)cccc21] | 3-(2,4-DIHYDROXY-5-ETHYL-PHENYL)-4-(1-N-BUTYL-INDOL-4-YL)-5-MERCAPTO-[1,2,4]TRIAZOLE |
| 35 | 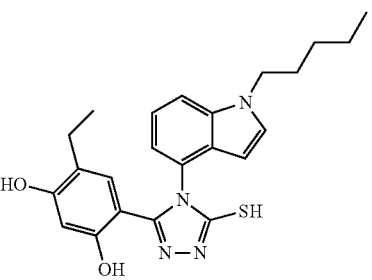 [SMILES: CCCCCn1ccc2c(-n3c(S)nnc3-c3cc(CC)c(O)cc3O)cccc21] | 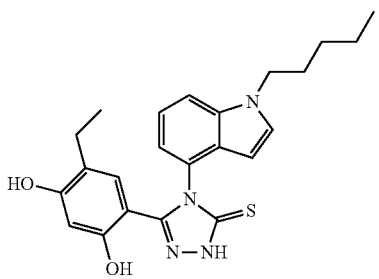 [SMILES: CCCCCn1ccc2c(-n3c(-c4cc(CC)c(O)cc4O)n[nH]c3=S)cccc21] | 3-(2,4-DIHYDROXY-5-ETHYL-PHENYL)-4-(1-N-PENTYL-INDOL-4-YL)-5-MERCAPTO-[1,2,4]TRIAZOLE |

TABLE 1-continued

| | STRUCTURE | TAUTOMERIC STRUCTURE | NAME |
|---|---|---|---|
| 36 | 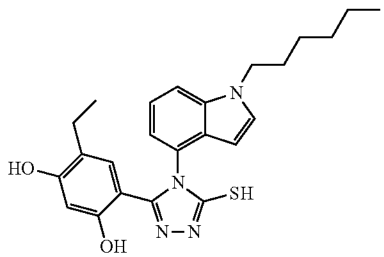 [SMILES: CCCCCCn1ccc2c(-n3c(S)nnc3-c3cc(CC)c(O)cc3O)cccc21] | | 3-(2,4-DIHYDROXY-5-ETHYL-PHENYL)-4-(1-N-HEXYL-INDOL-4-YL)-5-MERCAPTO-[1,2,4]TRIAZOLE |
| 37 | 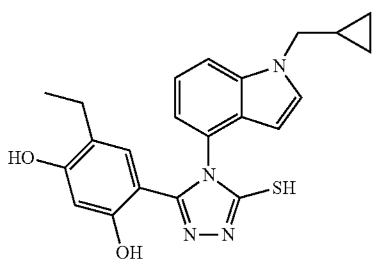 [SMILES: CCc1cc(-c2nnc(S)n2-c2cccc3c2ccn3CC2CC2)c(O)cc1O] | | 3-(2,4-DIHYDROXY-5-CYCLOPROPYL-PHENYL)-4-(1-(1-METHYLCYCLOPROPYL)-INDOL-4-YL)-5-MERCAPTO-[1,2,4]TRIAZOLE |
| 38 | 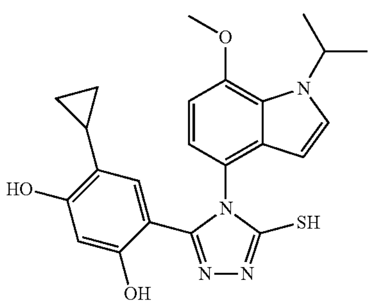 [SMILES: COc1ccc(-n2c(S)nnc2-c2cc(C3CC3)c(O)cc2O)c2ccn(C(C)C)c12] | | 3-(2,4-DIHYDROXY-5-CYCLOPROPYL-PHENYL)-4-(1-ISOPROPYL-7-METHOXY-INDOL-4-YL)-5-MERCAPTO-[1,2,4]TRIAZOLE |
| 39 | 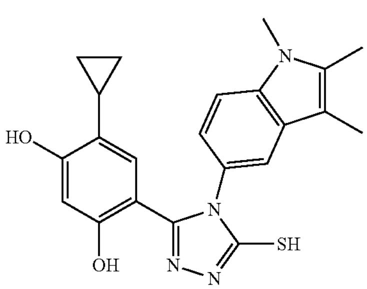 [SMILES: Cc1c(C)n(C)c2ccc(-n3c(S)nnc3-c3cc(C4CC4)c(O)cc3O)cc12] | | 3-(2,4-DIHYDROXY-5-CYCLOPROPYL-PHENYL)-4-(1,2,3-TRIMETHYL-INDOL-5-YL)-5-MERCAPTO-[1,2,4]TRIAZOLE |
| 40 | 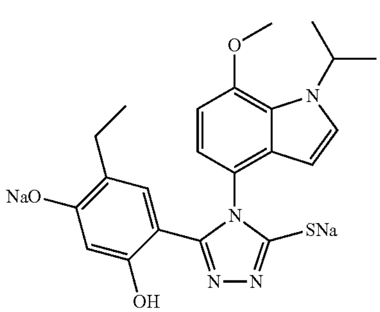 | | 3-(2,4-DIHYDROXY-5-ETHYL-PHENYL)-4-(1-ISOPROPYL-7-METHOXY-INDOL-4-YL)-5-MERCAPTO-[1,2,4]TRIAZOLE DISODIUM SALT |

TABLE 1-continued

| STRUCTURE | TAUTOMERIC STRUCTURE | NAME |
|---|---|---|
| 41 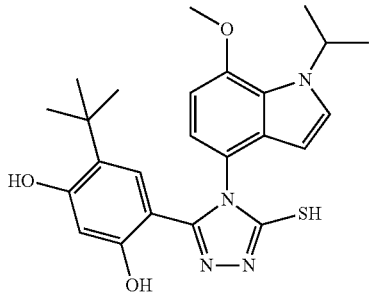 [SMILES: COc1ccc(-n2c(S)nnc2-c2cc(C(C)(C)C)c(O)cc2O)c2ccn(C(C)C)c12] | 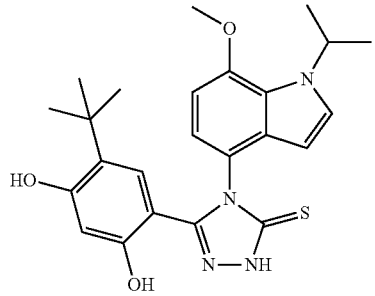 [SMILES: COc1ccc(-n2c(-c3cc(C(C)(C)C)c(O)cc3O)n[nH]c2=S)c2ccn(C(C)C)c12] | 3-(2,4-DIHYDROXY-5-TERT-BUTYL-PHENYL)-4-(1-ISOPROPYL-7-METHOXY-INDOL-4-YL)-5-MERCAPTO-[1,2,4]TRIAZOLE |
| 42 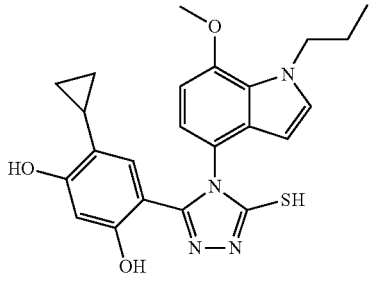 [SMILES: CCCn1ccc2c(-n3c(S)nnc3-c3cc(C4CC4)c(O)cc3O)ccc(OC)c21] | 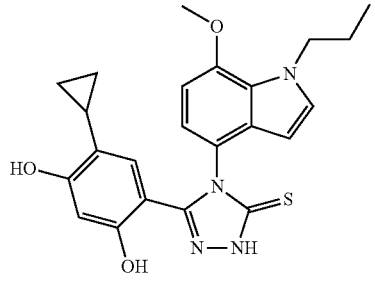 [SMILES: CCCn1ccc2c(-n3c(-c4cc(C5CC5)c(O)cc4O)n[nH]c3=S)ccc(OC)c21] | 3-(2,4-DIHYDROXY-5-CYCLOPROPYL-PHENYL)-4-(1-PROPYL-7-METHOXY-INDOL-4-YL)-5-MERCAPTO-[1,2,4]TRIAZOLE |
| 43 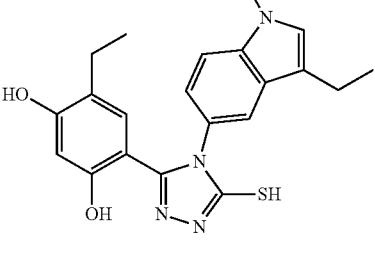 | 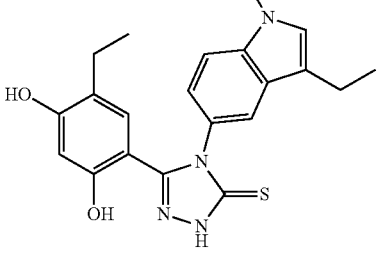 | 3-(2,4-DIHYDROXY-5-ETHYL-PHENYL)-4-(1-METHYL-3-ETHYL-INDOL-5-YL)-5-MERCAPTO-[1,2,4]TRIAZOLE |
| 44 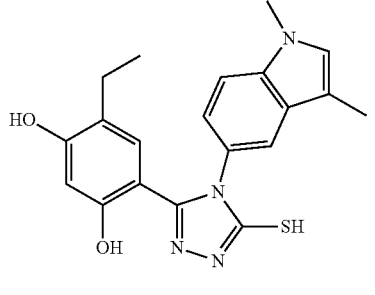 [SMILES: CCc1cc(-c2nnc(S)n2-c2ccc3c(c2)c(C)cn3C)c(O)cc1O] | 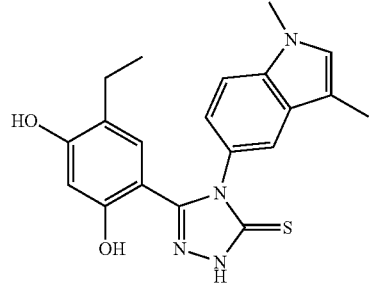 [SMILES: CCc1cc(-c2n[nH]c(=S)n2-c2ccc3c(c2)c(C)cn3C)c(O)cc1O] | 3-(2,4-DIHYDROXY-5-ETHYL-PHENYL)-4-(1,3-DIMETHYL-INDOL-5-YL)-5-MERCAPTO-[1,2,4]TRIAZOLE |
| 45 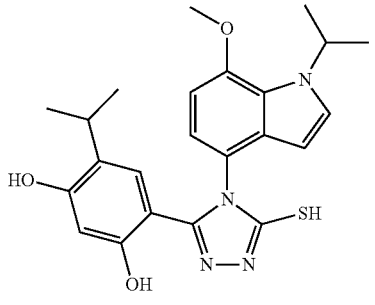 [SMILES: COc1ccc(-n2c(S)nnc2-c2cc(C(C)C)c(O)cc2O)c2ccn(C(C)C)c12] | 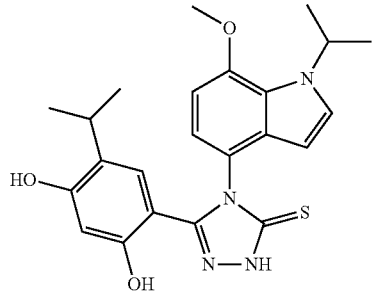 [SMILES: COc1ccc(-n2c(-c3cc(C(C)C)c(O)cc3O)n[nH]c2=S)c2ccn(C(C)C)c12] | 3-(2,4-DIHYDROXY-5-ISOPROPYL-PHENYL)-4-(1-ISOPROPYL-7-METHOXY-INDOL-4-YL)-5-MERCAPTO-[1,2,4]TRIAZOLE |

TABLE 1-continued

| | STRUCTURE | TAUTOMERIC STRUCTURE | NAME |
|---|---|---|---|
| 46 | 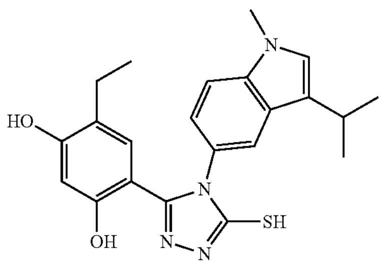 [SMILES: CCc1cc(-c2nnc(S)n2-c2ccc3c(c2)c(C(C)C)cn3C)c(O)cc1O] | | 3-(2,4-DIHYDROXY-5-ETHYL-PHENYL)-4-(1-METHYL-3-ISOPROPYL-INDOL-5-YL)-5-MERCAPTO-[1,2,4]TRIAZOLE |
| 48 | 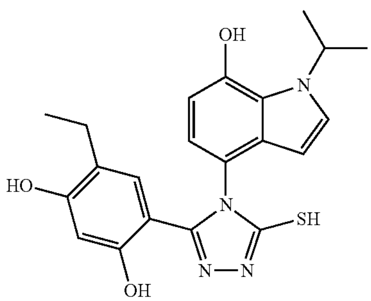 [SMILES: CCc1cc(-c2nnc(S)n2-c2ccc(O)c3c2ccn3C(C)C)c(O)cc1O] | | 3-(2,4-DIHYDROXY-5-ETHYL-PHENYL)-4-(1-ISOPROPYL-7-HYDROXY-INDOL-4-YL)-5-MERCAPTO-[1,2,4]TRIAZOLE |
| 49 | 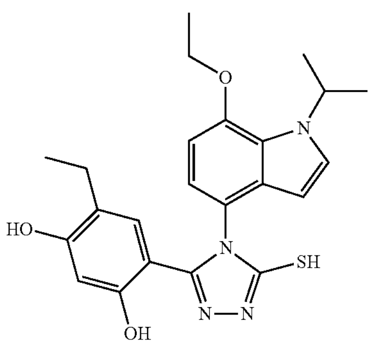 [SMILES: CCOc1ccc(-n2c(S)nnc2-c2cc(CC)c(O)cc2O)c2ccn(C(C)C)c12] | | 3-(2,4-DIHYDROXY-5-ETHYL-PHENYL)-4-(1-ISOPROPYL-7-ETHOXY-INDOL-4-YL)-5-MERCAPTO-[1,2,4]TRIAZOLE |
| 50 | 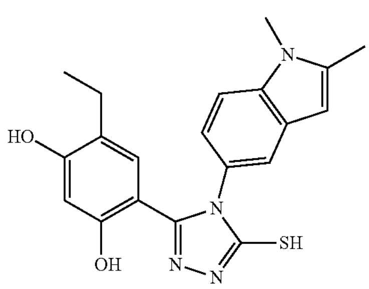 [SMILES: CCc1cc(-c2nnc(S)n2-c2ccc3c(c2)cc(C)n3C)c(O)cc1O] | | 3-(2,4-DIHYDROXY-5-ETHYL-PHENYL)-4-(1,2-DIMETHYL-INDOL-5-YL)-5-MERCAPTO-[1,2,4]TRIAZOLE |
| 51 | 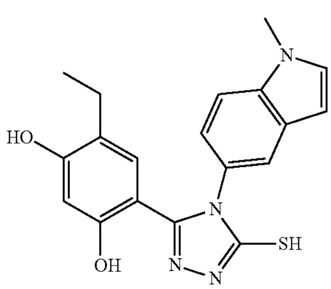 [SMILES: CCc1cc(-c2nnc(S)n2-c2ccc3c(ccn3C)c2)c(O)cc1O] | | 3-(2,4-DIHYDROXY-5-ETHYL-PHENYL)-4-(N-METHYL-INDOL-5-YL)-5-MERCAPTO-[1,2,4]TRIAZOLE |

TABLE 1-continued

| | STRUCTURE | TAUTOMERIC STRUCTURE | NAME |
|---|---|---|---|
| 55 | 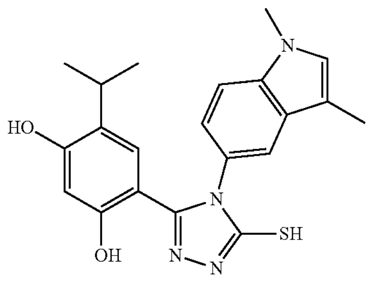 [SMILES: Cc1cn(C)c2ccc(-n3c(S)nnc3-c3cc(C(C)C)c(O)cc3O)cc12] | | 3-(2,4-DIHYDROXY-5-ISOPROPYL-PHENYL)-4-(1,3-DIMETHYL-INDOL-5-YL)-5-MERCAPTO-[1,2,4]TRIAZOLE |
| 56 | 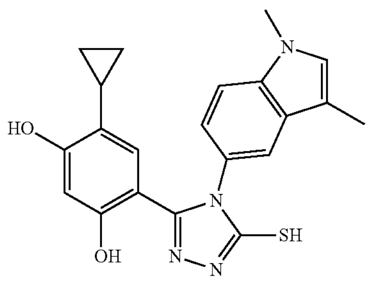 [SMILES: Cc1cn(C)c2ccc(-n3c(S)nnc3-c3cc(C4CC4)c(O)cc3O)cc12] | | 3-(2,4-DIHYDROXY-5-CYCLOPROPYL-PHENYL)-4-(1,3-DIMETHYL-INDOL-5-YL)-5-MERCAPTO-[1,2,4]TRIAZOLE |
| 57 | 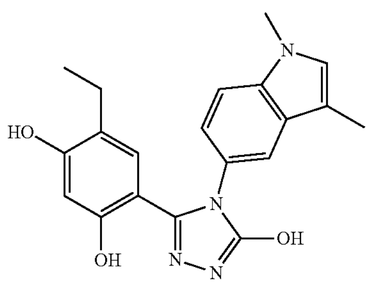 [SMILES: CCc1cc(-c2nnc(O)n2-c2ccc3c(c2)c(C)cn3C)c(O)cc1O] | | 3-(2,4-DIHYDROXY-5-ETHYL-PHENYL)-4-(1,3-DIMETHYL-INDOL-5-YL)-5-HYDROXY-[1,2,4]TRIAZOLE |
| 58 | 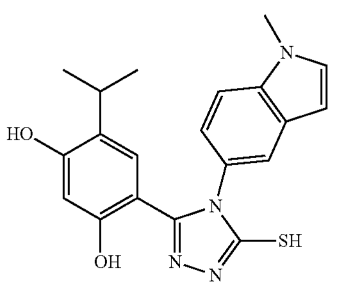 [SMILES: CC(C)c1cc(-c2nnc(S)n2-c2ccc3c(ccn3C)c2)c(O)cc1O] | | 3-(2,4-DIHYDROXY-5-ISOPROPYL-PHENYL)-4-(N-METHYL-INDOL-5-YL)-5-MERCAPTO-[1,2,4]TRIAZOLE |
| 59 | 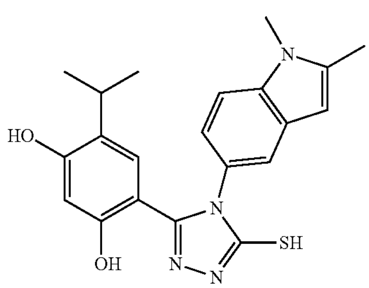 [SMILES: Cc1cc2cc(-n3c(S)nnc3-c3cc(C(C)C)c(O)cc3O)ccc2n1C] | | 3-(2,4-DIHYDROXY-5-ISOPROPYL-PHENYL)-4-(1,2-DIMETHYL-INDOL-5-YL)-5-MERCAPTO-[1,2,4]TRIAZOLE |

| | STRUCTURE | TAUTOMERIC STRUCTURE | NAME |
|---|---|---|---|
| 60 | 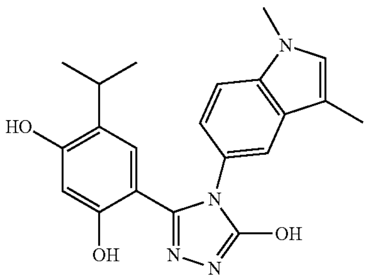 [SMILES: Cc1cn(C)c2ccc(-n3c(O)nnc3-c3cc(C(C)C)c(O)cc3O)cc12] | | 3-(2,4-DIHYDROXY-5-ISOPROPYL-PHENYL)-4-(1,3-DIMETHYL-INDOL-5-YL)-5-HYDROXY-[1,2,4]TRIAZOLE |
| 62 | 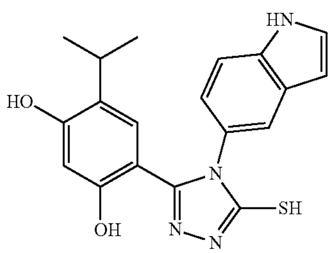 [SMILES: CC(C)c1cc(-c2nnc(S)n2-c2ccc3[nH]ccc3c2)c(O)cc1O] | | 3-(2,4-DIHYDROXY-5-ISOPROPYL-PHENYL)-4-(1H-INDOL-5-YL)-5-MERCAPTO-[1,2,4]TRIAZOLE |
| 63 | 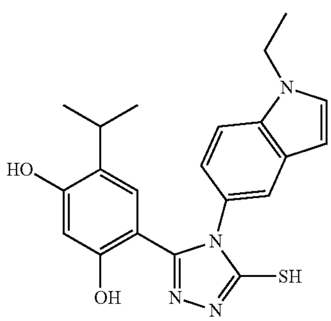 [SMILES: CCn1ccc2cc(-n3c(S)nnc3-c3cc(C(C)C)c(O)cc3O)ccc21] | | 3-(2,4-DIHYDROXY-5-ISOPROPYL-PHENYL)-4-(1-ETHYL-INDOL-5-YL)-5-MERCAPTO-[1,2,4]TRIAZOLE |
| 64 | 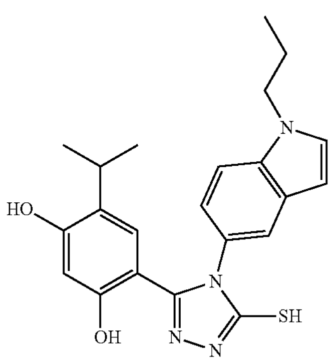 [SMILES: CCCn1ccc2cc(-n3c(S)nnc3-c3cc(C(C)C)c(O)cc3O)ccc21] | | 3-(2,4-DIHYDROXY-5-ISOPROPYL-PHENYL)-4-(1-PROPYL-INDOL-5-YL)-5-MERCAPTO-[1,2,4]TRIAZOLE |
| 65 | 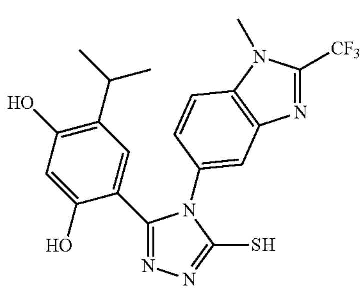 [SMILES: CC(C)c1cc(-c2nnc(S)n2-c2ccc3c(c2)nc(C(F)(F)F)n3C)c(O)cc1O] | | 3-(2,4-DIHYDROXY-5-ISOPROPYL-PHENYL)-4-(1-METHYL-2-TRIFLUOROMETHYL-BENZIMIDAZOL-5-YL)-5-MERCAPTO-[1,2,4]TRIAZOLE |

TABLE 1-continued

| | STRUCTURE | TAUTOMERIC STRUCTURE | NAME |
|---|---|---|---|
| 66 | 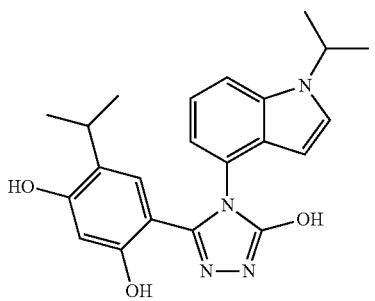 [SMILES: CC(C)c1cc(-c2nnc(O)n2-c2cccc3c2ccn3C(C)C)c(O)cc1O] | 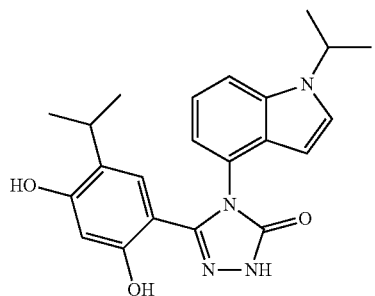 [SMILES: CC(C)c1cc(-c2n[nH]c(=O)n2-c2cccc3c2ccn3C(C)C)c(O)cc1O] | 3-(2,4-DIHYDROXY-5-ISOPROPYL-PHENYL)-4-(1-ISOPROPYL-INDOL-4-YL)-5-HYDROXY-[1,2,4]TRIAZOLE |

TABLE 2

Compounds according to Formula (Ia)

| No. | STRUCTURE | TAUTOMERIC STRUCTURE | NAME |
|---|---|---|---|
| 1A | 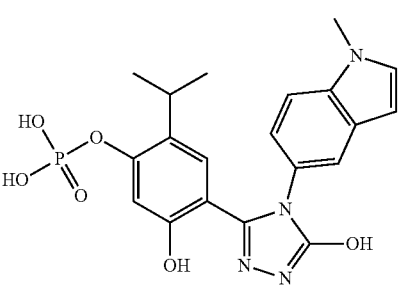 [SMILES: CC(C)c1cc(-c2nnc(O)n2-c2ccc3c(ccn3C)c2)c(O)cc1OP(=O)(O)O] | 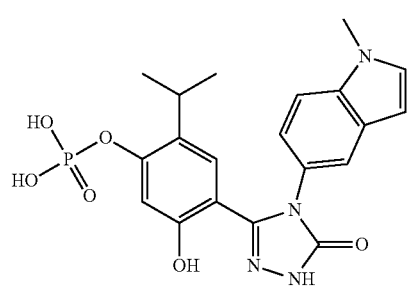 [SMILES: CC(C)c1cc(-c2n[nH]c(=O)n2-c2ccc3c(ccn3C)c2)c(O)cc1OP(=O)(O)O] | 5-HYDROXY-4-(5-HYDROXY-4-(1-METHYL-1H-INDOL-5-YL)-4H-1,2,4-TRIAZOL-3-YL)-2-ISOPROPYLPHENYL DIHYDROGEN PHOSPHATE |
| 2A | 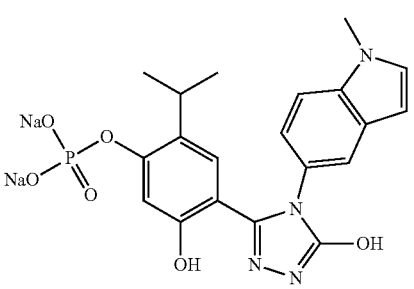 | 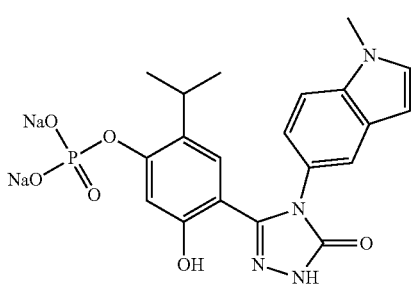 | SODIUM 5-HYDROXY-4-(5-HYDROXY-4-(1-METHYL-1H-INDOL-5-YL)-4H-1,2,4-TRIAZOL-3-YL)-2-ISOPROPYLPHENYL PHOSPHATE |
| 3A | 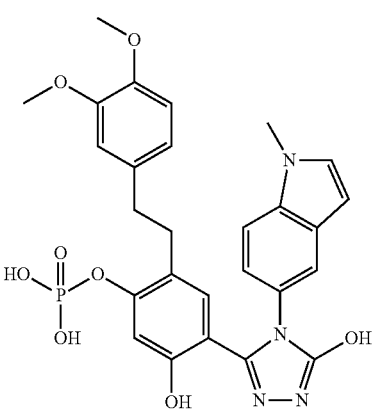 [SMILES: COc1ccc(CCc2cc(-c3nnc(O)n3-c3ccc4c(ccn4C)c3)c(O)cc2OP(=O)(O)O)cc1OC] | 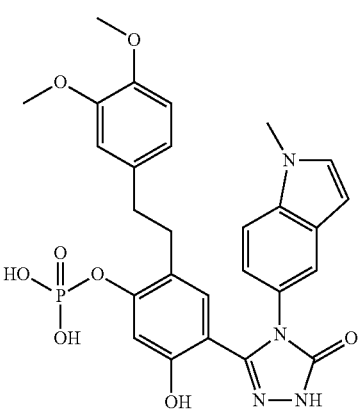 [SMILES: COc1ccc(CCc2cc(-c3n[nH]c(=O)n3-c3ccc4c(ccn4C)c3)c(O)cc2OP(=O)(O)O)cc1OC] | 2-(3,4-DIMETHOXY-PHENETHYL)-5-HYDROXY-4-(5-HYDROXY-4-(1-METHYL-1H-INDOL-5-YL)-4H-1,2,4-TRIAZOL-3-YL)PHENYL DIHYDROGEN PHOSPHATE |

TABLE 2-continued

Compounds according to Formula (Ia)

| No. | STRUCTURE | TAUTOMERIC STRUCTURE | NAME |
|---|---|---|---|
| 4A | 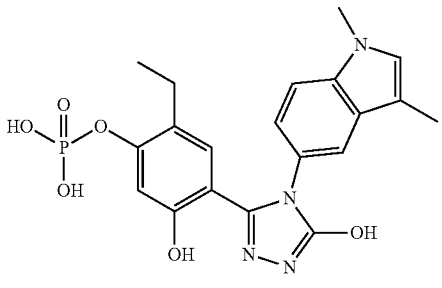 [SMILES: CCc1cc(-c2nnc(O)n2-c2ccc3c(c2)c(C)cn3C)c(O)cc1OP(=O)(O)O] | | 4-(4-(1,3-DIMETHYL-1H-INDOL-5-YL)-5-HYDROXY-4H-1,2,4-TRIAZOL-3-YL)-2-ETHYL-5-HYDROXYPHENYL DIHYDROGEN PHOSPHATE |

The Hsp90 inhibitory compounds used in the disclosed combination therapies can be prepared according to the procedures disclosed in U.S. Patent Publication No. 2006/0167070 and WO2009/023211. These triazolone compounds typically can form a tautomeric structure as shown below and as exemplified by the tautomeric structures shown in Tables 1 and 2:

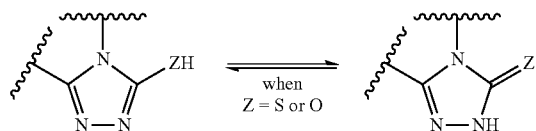

The present invention provides pharmaceutical combinations for the treatment, prophylaxis, and amelioration of proliferative disorders, such as cancer. In a specific embodiment, the combination comprises one or more Hsp90 inhibitors according to formulae (I) or (Ia), or a compound in Tables 1 or 2, or a tautomer or a pharmaceutically acceptable salt thereof in addition to an EGFR inhibitor.

In one embodiment, the combination includes a pharmaceutical composition or a single unit dosage form containing both an Hsp90 inhibitor and an EGFR inhibitor. Pharmaceutical combinations and dosage forms described herein comprise the two active ingredients in relative amounts and formulated in such a way that a given pharmaceutical combination or dosage form can be used to treat proliferative disorders, such as cancer. Preferred pharmaceutical combinations and dosage forms comprise a compound of formulae (I) or (Ia), or a compound in Tables 1 or 2, or a tautomer or pharmaceutically acceptable salt thereof, in combination with an EGFR inhibitor. In other embodiments, the Hsp90 inhibitor and the EGFR inhibitor may be in individual or separate pharmaceutical compositions, depending on the dosing schedules, preferred routes of administration, and available formulations of the two inhibitors. Optionally, these embodiments can also contain one or more additional therapeutic agents.

The pharmaceutical combinations described herein are formulated to be compatible with its intended route of administration. Examples of routes of administration include, parenteral, e.g., intravenous, intradermal, subcutaneous, oral (e.g., inhalation), intranasal, transdermal, transmucosal, and rectal administration. In a specific embodiment, the combination is formulated in accordance with routine procedures as a pharmaceutical composition adapted for intravenous, subcutaneous, intramuscular, oral, intranasal or topical administration to human beings. In a preferred embodiment, the combination is formulated in accordance with routine procedures for subcutaneous administration to human beings.

In a specific embodiment, the combination therapies described herein comprise one or more compounds and at least one other therapy which has the same mechanism of action as said compounds. In another specific embodiment, the combination therapies described herein comprise one or more compounds described herein and at least one other therapy which has a different mechanism of action than said compounds. In certain embodiments, the combination therapies described herein improve the therapeutic effect of one or more triazolone compounds described herein by functioning together with the EGFR inhibitor to have an additive or synergistic effect. In certain embodiments, the combination therapies described herein reduce the side effects associated with the therapies. In certain embodiments, the combination therapies described herein reduce the effective dosage of one or more of the therapies.

In a specific embodiment, the combination comprising one or more triazolone compounds described herein is administered to a subject, preferably a human, to prevent, treat, manage, or ameliorate cancer, or one or more symptom thereof. In accordance with the invention, pharmaceutical combination described herein may also comprise one or more other agents being used, have been used, or are known to be useful in the treatment or amelioration of cancer, particularly non-small cell lung cancer, pancreatic cancer, ovarian cancer, gastrointestinal cancer, prostate cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, lymphoma, multiple myeloma, or chronic lymphocytic leukemia.

The pharmaceutical combinations described herein utilize pharmaceutical compositions and dosage forms which comprise one or more excipients. Suitable excipients are well known to those skilled in the art of pharmacy.

The triazolone compounds described herein can be also formulated into or administered by controlled release means or by delivery devices that are well known to those of ordinary skill in the art. Examples include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, The present invention also includes a method of using the combination in treating a proliferative disorder in a subject, typically a human subject. More particularly, the method includes comprising administering to a subject in need thereof an effective amount of the pharmaceutical combination comprising an Hsp90 inhibitor and an EGFR inhibitor as described herein. In one embodiment, the proliferative disorder is cancer. In one aspect of this embodiment, the cancer is non-small cell lung cancer, pancreatic cancer, ovarian cancer, gastrointestinal cancer, prostate cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, lymphoma, multiple myeloma, or chronic lymphocytic leukemia. In one aspect of this embodiment, the cancer is locally advanced or metastatic non-small cell lung cancer or locally advanced, unresectable or metastatic pancreatic cancer.

In another embodiment, the proliferative disorder is associated with smooth muscle cell proliferation such as hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

In a preferred embodiment, the proliferative disorder is cancer. Cancers that can be treated by the methods described herein include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia and heavy chain disease.

Other examples of leukemias include acute and/or chronic leukemias, e.g., lymphocytic leukemia, e.g., as exemplified by the p388 (murine) cell line, large granular lymphocytic leukemia, and lymphoblastic leukemia; T-cell leukemias, e.g., T-cell leukemia, as exemplified by the CEM, Jurkat, and HSB-2 (acute), YAC-1 (murine) cell lines, T-lymphocytic leukemia, and T-lymphoblastic leukemia; B-cell leukemia, e.g., as exemplified by the SB (acute) cell line, and B-lymphocytic leukemia; mixed cell leukemias, e.g., B- and T-cell leukemia and B- and T-lymphocytic leukemia; myeloid leukemias, e.g., granulocytic leukemia, myelocytic leukemia, e.g., as exemplified by the HL-60 (promyelocyte) cell line, and myelogenous leukemia, e.g., as exemplified by the K562 (chronic)cell line; neutrophilic leukemia; eosinophilic leukemia; monocytic leukemia, e.g., as exemplified by the THP-1 (acute) cell line; myelomonocytic leukemia; Naegeli-type myeloid leukemia; and nonlymphocytic leukemia. Other examples of leukemias are described in Chapter 60 of THE CHEMOTHERAPY SOURCEBOOK (Michael C. Perry Ed., Williams & Williams (1992)) and Section 36 of HOLLAND FRIE CANCER MEDICINE (Bast et al. Eds., 5th ed., B.C. Decker Inc. (2000)).

In one embodiment, the disclosed method is believed to be effective in treating a subject with non-solid tumors such as multiple myeloma. In another embodiment, the disclosed method is believed to be effective against T-cell leukemia, e.g., as exemplified by Jurkat and CEM cell lines; B-cell leukemia, e.g., as exemplified by the SB cell line; promyelocytes, e.g., as exemplified by the HL-60 cell line; uterine sarcoma, e.g., as exemplified by the MES-SA cell line; monocytic leukemia, e.g., as exemplified by the THP-1 (acute) cell line; and lymphoma, e.g., as exemplified by the U937 cell line.

In one embodiment, the disclosed method is believed to be effective in treating a subject with non-Hodgkin's lymphoma (NHL). Lymphomas are generally classified as either Hodgkin's disease (HD) or non-Hodgkin's lymphomas. NHL differs from HD by the absence of Reed-Sternberg cells. The course of NHL is less predictable than HD and is more likely to spread to areas beyond the lymph nodes. NHL can be further divided into B-cell NHL and T-cell NHL, each of which can be further categorized into a variety of different subtypes. For example, B-cell NHL includes Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, extranodal marginal zone B-cell lymphoma and lymphoplamacytic lymphoma/Waldenstrom macroglobulinemia. T-cell NHL includes anaplastic large-cell lymphoma, precursor-T-cell lymphoblastic leukemia/lymphoma, unspecified peripheral T-cell lymphoma, acute lymphoblastic leukemia/lymphoma, angioimmunoblastic T-cell lymphoma and mycosis fungoides.

Without wishing to be bound by any theory, it is believed that the Hsp90 inhibitory compounds used in the method described herein are useful for treating NHLs, including B-cell and T-cell NHLs, because Hsp90 is upregulated in many NHLs. In particular, in a survey of 412 cases of NHL in B-cell NHL, Hsp90 was found to be moderately to strongly over expressed in all cases of Burkitt's lymphoma (5/5, 100%), and in a subset of follicular lymphoma (17/28, 61%), diffuse large B-cell lymphoma (27/46, 59%), nodal marginal zone B-cell lymphoma (6/16, 38%), plasma cell neoplasms (14/39, 36%), small lymphocytic lymphoma/chronic lymphocytic leukemia (3/9, 33%), mantle cell lymphoma (12/38, 32%) and lymphoplamacytic lymphoma/Waldenstrom macroglobulinemia (3/10, 30%). In addition, in T-cell NHL, Hsp90 was found to be moderately to strongly over expressed in a subset of anaplastic large-cell lymphoma (14/24, 58%), precursor-T-cell lymphoblastic leukemia/lymphoma (20/65, 31%), unspecified peripheral T-cell lymphoma (8/43, 23%) and angioimmunoblastic T-cell lymphoma (2/17, 12%). Valbuena, et al., *Modern Pathology* (2005), 18:1343-1349.

Some of the disclosed methods can be particularly effective at treating subjects whose cancer has become "drug resistant" or "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. "Drug resistant" tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Other anti-proliferative or anti-cancer therapies may be combined with the compounds described herein to treat proliferative diseases such as cancer. Other therapies or anti-cancer agents that may be used in combination with the anti-cancer agents described herein include surgery, radiotherapy (including gamma-radiation, neutron beam radiotherapy, electron beam radiotherapy, proton therapy, brachytherapy, and systemic radioactive isotopes), endocrine therapy, biologic response modifiers (including interferons, interleukins, and tumor necrosis factor (TNF)), hyperthermia and cryotherapy, agents to attenuate any adverse effects (e.g., antiemetics), and other approved chemotherapeutic drugs.

The therapeutic agents of the combination therapies described herein can be administered sequentially or concurrently. In one embodiment, the administration of the Hsp90 inhibitor and the EGFR inhibitor are done concurrently. In another embodiment, the administration of the Hsp90 inhibitor and the EGFR inhibitor are done separately. In another embodiment, the administration of the Hsp90 inhibitor and the EGFR inhibitor are done sequentially. In another embodiment, the administration of the Hsp90 inhibitor is administered prior to or after the EGFR inhibitor. In one embodiment, the administration of the Hsp90 inhibitor and the EGFR inhibitor are done until the cancer is cured or stabilized or improved.

In one specific embodiment, the present method includes treating, managing, or ameliorating cancer, or one or more symptoms thereof, comprising administering to a subject in need thereof one or more compounds represented by the structural formulae (I) or (Ia) or a compound in Table 1 or Table 2, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an effective amount of an EGFR inhibitor.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an effective amount of erlotinib.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an effective amount of an EGFR inhibitor.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an effective amount of erlotinib.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In yet another embodiment, the method of treating a subject with cancer, wherein the subject is being or has been treated with a chemotherapeutic agent, includes administering to the subject an effective amount of a triazolone compound represented by the structural formulae (I) or (Ia) or a compound in Table 1 or Table 2, in combination with an EGFR inhibitor such as erlotinib, gefitinib or cetuximab.

In one embodiment, the method of treating a subject with cancer, wherein the subject is being or has been treated with a chemotherapeutic agent, includes administering to the subject an effective amount of a triazolone compound represented by the structural formulae (I) or (Ia) or a compound in Table 1 or Table 2, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In another embodiment, the method of treating a subject with cancer, wherein the subject is being or has been treated with a chemotherapeutic agent, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an EGFR inhibitor such as erlotinib, gefitinib or cetuximab.

In another embodiment, the method of treating a subject with cancer, wherein the subject is being or has been treated with a chemotherapeutic agent, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with erlotinib.

In another embodiment, the method of treating a subject with cancer, wherein the subject is being or has been treated with a chemotherapeutic agent, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an EGFR inhibitor such as erlotinib, gefitinib or cetuximab.

In another embodiment, the method of treating a subject with cancer, wherein the subject is being or has been treated with a chemotherapeutic agent, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with erlotinib.

In one embodiment, the method of treating a subject with cancer, wherein the subject is being or has been treated with a chemotherapeutic agent, includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In one embodiment, the method of treating a subject with cancer, wherein the subject is being or has been treated with a chemotherapeutic agent, includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In one embodiment, the method of treating a subject with cancer, wherein the subject has proven refractory to other therapies but is no longer on these therapies, includes administering to the subject an effective amount of a triazolone compound represented by the structural formulae (I) or (Ia) or a compound in Table 1 or Table 2, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In another embodiment, the method of treating a subject with cancer, wherein the subject has proven refractory to other therapies but is no longer on these therapies, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an EGFR inhibitor such as erlotinib, gefitinib or cetuximab.

In another embodiment, the method of treating a subject with cancer, wherein the subject has proven refractory to other therapies but is no longer on these therapies, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with erlotinib.

In another embodiment, the method of treating a subject with cancer, wherein the subject has proven refractory to other therapies but is no longer on these therapies, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an EGFR inhibitor such as erlotinib, gefitinib or cetuximab.

In another embodiment, the method of treating a subject with cancer, wherein the subject has proven refractory to other therapies but is no longer on these therapies, includes administering to the subject an effective amount of 5-hydroxy-4-(5-hydroxy-4-(1-methyl-1H-indol-5-yl)-4H-1,2,4- triazol-3-yl)-2-isopropylphenyl dihydrogen phosphate, or a tautomer, or a pharmaceutically acceptable salt thereof, in combination with erlotinib.

In one embodiment, the method of treating a subject with cancer, wherein the subject has proven refractory to other therapies but is no longer on these therapies, includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In one embodiment, the method of treating a subject with cancer, wherein the subject has proven refractory to other therapies but is no longer on these therapies, includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an EGFR inhibitor such as erlotinib, gefitinib or cetuximab, wherein the cancer is selected from the group consisting of non-small cell lung cancer, pancreatic cancer, ovarian cancer, gastrointestinal cancer, prostate cancer, small cell lung carcinoma, stomach cancer, cervical cancer, gastric cancer, rectal cancer, kidney cancer, liver cancer, gallbladder cancer, head and neck cancer, transitional cell carcinoma, squamous cell carcinoma, melanoma, glioblastoma, gliosarcoma, colorectal cancer, breast cancer, esophageal cancer, bladder cancer, hepatocellular carcinoma, renal cell carcinoma, brain and central nervous system cancer, neuroendocrine tumors, colon carcinoma, lymphoma, multiple myeloma, or chronic lymphocytic leukemia.

In one further embodiment, the method includes inhibiting the growth of a cancer or tumor cell comprising the steps of: (a) contacting said cell with an effective amount of a compound of formulae (I) or (Ia) or a compound in Table (1) or Table (2), or tautomer or a pharmaceutically acceptable salt thereof; and (b) exposing said cell to an effective amount of an EGFR inhibitor such as erlotinib, gefitinib or cetuximab.

In one further embodiment, the method includes inhibiting the growth of a cancer or tumor cell comprising the steps of: (a) contacting said cell with an effective amount of a compound of -(2,4-dihydroxy-5-isopropyl-phenyl)-4-(1-methyl-indol-5-yl)-5-hydroxy-[1,2,4]triazole, or a tautomer, or a pharmaceutically acceptable salt thereof; and (b) exposing said cell to an effective amount of an EGFR inhibitor such as erlotinib, gefitinib or cetuximab.

In one further embodiment, the method includes inhibiting the growth of a cancer or tumor cell comprising the steps of: (a) contacting said cell with an effective amount of a compound of -(2,4-dihydroxy-5-isopropyl-phenyl)-4-(1-methyl-indol-5-yl)-5-hydroxy-[1,2,4]triazole, or a tautomer, or a pharmaceutically acceptable salt thereof; and (b) exposing said cell to an effective amount of erlotinib.

In one further embodiment, the method includes inhibiting the growth of a cancer or tumor cell comprising the steps of: (a) contacting said cell with an effective amount of a compound of 5-hydroxy-4-(5-hydroxy-4-(1-methyl-1H-indol-5-yl)-4H-1,2,4-triazol-3-yl)-2-isopropylphenyl dihydrogen phosphate, or tautomer or a pharmaceutically acceptable salt thereof; and (b) exposing said cell to an effective amount of an EGFR inhibitor such as erlotinib, gefitinib or cetuximab.

In one further embodiment, the method includes inhibiting the growth of a cancer or tumor cell comprising the steps of: (a) contacting said cell with an effective amount of a compound of 5-hydroxy-4-(5-hydroxy-4-(1-methyl-1H-indol-5-yl)-4H-1,2,4-triazol-3-yl)-2-isopropylphenyl dihydrogen phosphate, or tautomer or a pharmaceutically acceptable salt thereof; and (b) exposing said cell to an effective amount of erlotinib.

In general, the recommended daily dose range of a triazolone compound for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different cancers, as will be readily known by those of ordinary skill in the art. Similarly, amounts sufficient to prevent, manage, treat or ameliorate such cancers, but insufficient to cause, or sufficient to reduce, adverse effects associated with the triazolone compounds described herein are also encompassed by the above described dosage amounts and dose frequency schedules. Further, when a patient is administered multiple dosages of a triazolone compound described herein, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition comprising a triazolone compound described herein administered to prevent, treat, manage, or ameliorate cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition comprising a compound described herein administered to prevent, treat, manage, or ameliorate cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg. The unit dose can be administered 1, 2, 3, 4 or more times daily, or once every 2, 3, 4, 5, 6 of 7 days, or once weekly, once every two weeks, once every three weeks or once monthly.

In certain embodiments, when the triazolone compounds described herein are administered in combination with an EGFR inhibitor, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies are administered within the same patient visit.

In certain embodiments, one or more compounds describer herein and one or more other the therapies (e.g., therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound described herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, a method of preventing, treating, managing, or ameliorating a proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, preferably, once every 2 days, once every 3 days, once every 4 days, once every 5 days, once every 6 days, once every 7 days, once every 8 days, once every 10 days, once every two weeks, once every three weeks, or once a month. Alternatively, the dose can be divided into portions (typically equal portions) administered two, three, four or more times a day.

EXAMPLES

Example 1

Compound 26 Displayed Anti-Tumor Activity Against Human Tumor Cells in a Nude Mouse Xenograft Model The human squamous non-small cell lung cancer cell line, RERF-LC-AI (RCB0444; S. Kyoizumi, et al., *Cancer. Res.* 45:3274-3281, 1985), was obtained from the Riken Cell Bank (Tsukuba, Ibaraki, Japan). The cell line was cultured in growth media prepared from 50% Dulbecco's Modified Eagle Medium (high glucose), 50% RPMI Media 1640, 10% fetal bovine serum (FBS), 1% 100× L-glutamine, 1% 100× penicillin-streptomycin, 1% 100× sodium pyruvate and 1% 100×MEM non-essential amino acids. FBS was obtained from American Type Culture Collection (Manassas, Va., USA) and all other reagents were obtained from Invitrogen Corp. (Carlsbad, Calif., USA). Approximately 4-5×10(6) cells that had been cryopreserved in liquid nitrogen were rapidly thawed at 37° C. and transferred to a 175 cm$^2$ tissue culture flask containing 50 ml of growth media and then incubated at 37° C. in a 5% $CO_2$ incubator.

The growth media was replaced every 2-3 days until the flask became 90% confluent, typically in 5-7 days. To passage and expand the cell line, a 90% confluent flask was washed with 10 ml of room temperature phosphate buffered saline (PBS) and the cells were disassociated by adding 5 ml 1× trypsin-EDTA (Invitrogen) and incubating at 37° C. until the cells detached from the surface of the flask. To inactivate the trypsin, 5 ml of growth media was added and then the contents of the flask were centrifuged to pellet the cells. The supernatant was aspirated and the cell pellet was resuspended in 10 ml of growth media and the cell number determined using a hemocytometer. Approximately 1-3×10(6) cells per flask were seeded into 175 cm$^2$ flasks containing 50 ml of growth media and incubated at 37° C. in a 5% $CO_2$ incubator. When the flasks reached 90% confluence, the above passaging process was repeated until sufficient cells had been obtained for implantation into mice.

Seven to eight week old, female Crl:CD-1-nuBR (nude) mice were obtained from Charles River Laboratories (Wilmington, Mass., USA) Animals were housed 4-5/cage in microisolators, with a 12 hr/12 hr light/dark cycle, acclimated for at least 1 week prior to use and fed normal laboratory chow ad libitum. Studies were conducted on animals between 8 and 12 weeks of age at implantation. To implant RERF-LC-AI tumor cells into nude mice, the cells were trypsinized as above, washed in PBS and resuspended at a concentration of 50×10(6) cells/ml in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 ml of the cell suspension was injected subcutaneously into the flank of each nude mouse. Tumor volumes (V) were calculated by caliper measurement of the width (W), length (L) and thickness (T) of tumors using the following formula: $V=0.5236\times(L\times W\times T)$.

In vivo passaged RERF-LC-AI tumor cells (RERF-LC-AI$^{IVP}$) were isolated to improve the rate of tumor implantation relative to the parental cell line in nude mice. RERF-LC-AI tumors were permitted to develop in vivo until they reached approximately 250 mm$^3$ in volume, which required approximately 3 weeks following implantation. Mice were euthanized via $CO_2$ asphyxiation and their exteriors sterilized with 70% ethanol in a laminar flow hood. Using sterile technique, tumors were excised and diced in 50 ml PBS using a scalpel blade. A single cell suspension was prepared using a 55 ml Wheaton Safe-Grind tissue grinder (catalog #62400-358; VWR International, West Chester, Pa., USA) by plunging the pestle up and down 4-5 times without twisting. The suspension was strained through a 70 µM nylon cell strainer and then centrifuged to pellet the cells. The resulting pellet was resuspended in 0.1 M $NH_4Cl$ to lyse contaminating red blood cells and then immediately centrifuged to pellet the cells. The cell pellet was resuspended in growth media and seeded into 175 cm$^2$ flasks containing 50 ml of growth media at 1-3 tumors/flask or approximately 10×10(6) cells/flask. After overnight incubation at 37° C. in a 5% $CO_2$ incubator, non-adherent cells were removed by rinsing two times with PBS and then the cultures were fed with fresh growth media. When the flasks reached 90% confluence, the above passaging process was repeated until sufficient cells had been obtained for implantation into mice.

RERF-LC-AI$^{IVP}$ cells were then implanted as above and tumors were permitted to develop in vivo until the majority reached an average of 100-200 mm$^3$ in tumor volume, which typically required 2-3 weeks following implantation Animals with oblong or very small or large tumors were discarded, and only animals carrying tumors that displayed consistent growth rates were selected for studies. Animals were randomized into treatment groups so that the average tumor volumes of each group were similar at the start of dosing.

The Hsp90 inhibitor, 17-allylamino-17-demethoxygeldanamycin (17-AAG), was employed as a positive control (Albany Molecular Research, Albany, N.Y., USA). Stock solutions of test articles were prepared by dissolving the appropriate amounts of each compound in dimethyl sulfoxide (DMSO) by sonication in an ultrasonic water bath. Stock solutions were prepared weekly, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution was stored at room temperature for up to 3 months prior to use. To prepare formulations for daily dosing, DMSO stock solutions were diluted 1:10 with 20% Cremophore RH40. The final formulation for dosing contained 10% DMSO, 18% Cremophore RH40, 3.6% dextrose, 68.4% water and the appropriate amount of test article. Animals were intraperitoneally (i.p.) injected with this solution at 10 ml per kg body weight on a schedule of 5 days per week (Monday, Tuesday, Wednesday, Thursday and Friday, with no dosing on Saturday and Sunday) for a total of 15 doses.

Figure 2:
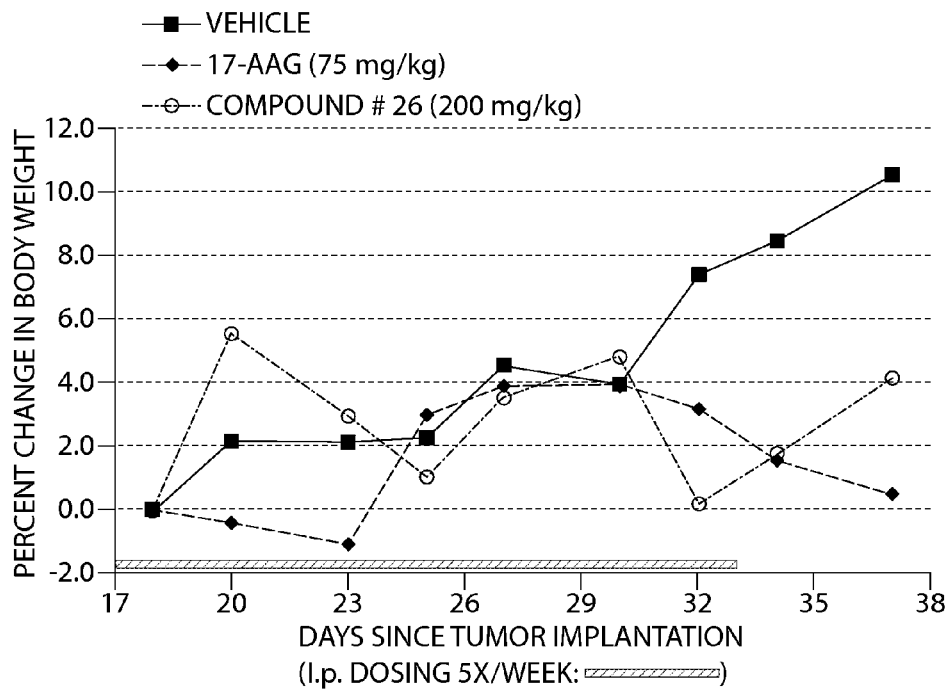
FIG. 2 demonstrates that treatment with Compound 26 does not cause overt toxicity in a nude mouse xenograft model using RERF-LC-AI$^{IVP}$ human lung tumor cells (data derived from the same study presented in FIG. 5). Tumor bearing animals (8 mice/group) were i.p. injected 5 times per week for a total of 15 doses (hatched bar) and the cumulative average percent changes in body weights for each group relative to the start of dosing were determined every 2-3 days. Treatment with a dose of 200 mg/kg body weight of Compound 26 was not overtly toxic, as indicated by the minimal effects on the animal body weights in the test article-treated versus vehicle-treated groups.

As shown in FIG. 1, treatment with 200 mg/kg body weight of Compound 26 decreased the growth rate of RERF-LC-AI$^{IVP}$ human lung tumor cells in nude mice, as did a dose of 75 mg/kg body weight of 17-AAG (an unrelated Hsp90 inhibitor). This effect was not associated with overt toxicity, as shown by the minimal effect on body weights depicted in FIG. 2.

Example 2

The Combination of Compound 1 and Erlotinib HCl Displayed Enhanced Anti-Tumor Activity Against Human Tumor Cells in a SCID Mouse Xenograft Model The human non-small cell lung cancer (NSCLC) cell line, HCC827 (ATCC #CRL-2868) was obtained from the American Type Culture Collection (ATCC; Manassas, Va., USA).

HCC827 cells were cultured in growth media prepared from 50% Dulbecco's Modified Eagle Medium (high glucose), 50% RPMI Media 1640 (4.5 g/L glucose), 10% fetal bovine serum (FBS), 10 mM HEPES, 1% 100× Penicillin-Streptomycin, 1% 100× sodium pyruvate and 1% 100×MEM non-essential amino acids. FBS was obtained from ATCC and all other reagents were obtained from Invitrogen Corp. (Carlsbad, Calif., USA). Cells that had been cryopreserved in liquid nitrogen were rapidly thawed at 37° C. and transferred to a tissue culture flask containing growth media and then incubated at 37° C. in a 5% $CO_2$ incubator. To expand the HCC827 cell line, cultures were split 1:3 every 3 days when 175 cm$^2$ flasks became 85% confluent. Cultures were passaged by washing with 10 mL of room temperature phosphate buffered saline (PBS) and then disassociating cells by adding 5 mL 1× trypsin-EDTA and incubating at 37° C. until the cells detached from the surface of the flask. To inactivate the trypsin, 5 mL of growth media was added and then the contents of the flask were centrifuged to pellet the cells. The supernatant was aspirated and the cell pellet was resuspended in 10 mL of growth media and the cell number determined using a hemocytometer. Cells were seeded into 175 cm$^2$ flasks containing 50 mL of growth media and incubated at 37° C. in a 5% $CO_2$ incubator. When the flasks reached 85% confluence, the above passaging process was repeated until sufficient cells had been obtained for implantation into mice.

Six to eight week old, female CB17/Icr-Prkdc$^{scid}$/Crl (SCID) mice were obtained from Charles River Laboratories (Wilmington, Mass., USA) Animals were housed 4-5/cage in micro-isolators, with a 12 hr/12 hr light/dark cycle, acclimated for at least 1 week prior to use and fed normal laboratory chow ad libitum. Animals were between seven to twelve weeks of age at implantation. To implant HCC827 tumor cells into SCID mice, cells were collected as described above, washed in PBS and resuspended at a concentration of 5×10(7) cells/mL in 50% non-supplemented medium and 50% Matrigel Basement Membrane Matrix (#354234; BD Biosciences; Bedford, Mass., USA). Using a 27 gauge needle and 1 cc syringe, 5×10(6) HCC827 cells in 0.1 mL of a cell suspension were injected subcutaneously into the flanks of SCID mice.

For the HCC827 model, tumors were then permitted to develop in vivo until the majority reached approximately 100-200 mm$^3$ in tumor volume, which required ~2 weeks Animals with oblong, very small or large tumors were discarded and only animals carrying tumors that displayed consistent growth rates were selected for studies. Tumor volumes (V) were calculated by caliper measurement of the width (W), length (L) and thickness (T) of tumors using the following formula: V=0.5236×(L×W×T) Animals were randomized into treatment groups so that the average tumor volumes of each group were similar at the start of dosing. % T/C values, as a measure of efficacy, were determined as follows:

(i) If Δ T>0: % T/C=(ΔT/Δ C)×100
(ii) If Δ T<0: % T/C=(ΔT/T$_0$)×100
(iii) Δ T=Change in average tumor volume between start of dosing and the end of study.
(iv) Δ C=Change in average tumor volume between start of dosing and the end of study.
(v) T$_0$=Average tumor volume at start of dosing.

To formulate the test article, Compound 1, in DRD, stock solutions of the test article were prepared by dissolving the appropriate amounts of the compound in dimethyl sulfoxide (DMSO) by sonication in an ultrasonic water bath. Stock solutions were prepared weekly, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) was also prepared by first heating 100% Cremophore RH40 at 50-60° C. until liquefied and clear, diluting 1:5 with 100% D5W, reheating again until clear and then mixing well. This solution can be stored at room temperature for up to 3 months prior to use. To prepare DRD formulations for daily dosing, DMSO stock solutions were diluted 1:10 with 20% Cremophore RH40. The final DRD formulation for dosing contained 10% DMSO, 18% Cremophore RH40, 3.6% dextrose, 68.4% water and the appropriate amount of test article. Animals were intravenous (i.v.) injected via the tail vein with this formulation at 10 mL per kg body weight on 1 day each week. Erlotinib HCl (Tarceva) was purchased from LGM Pharmaceuticals (Boca Raton, Forida, USA), stored at 4° C., and the appropriate amount of the test article was dissolved in 1% Tween 80 in PBS by sonication in an ultrasonic water bath. Animals were orally (p.o.) dosed by gavage with this formulation at 5 mL per kg body weight on 1 day each week.

Figure 3:
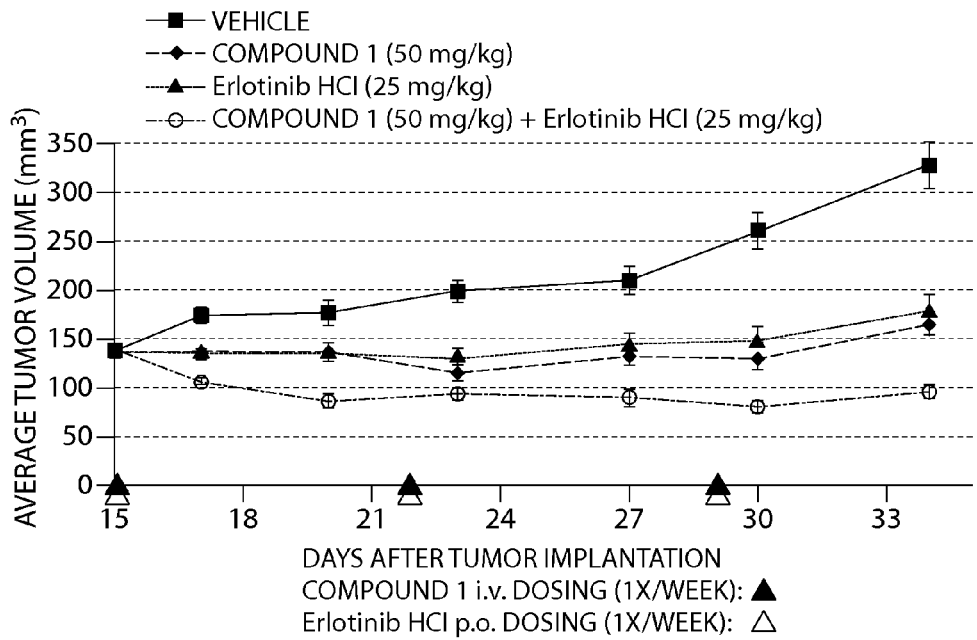
FIG. 3 shows a SCID mouse xenograft study on the effects of the combination of Compound 1 plus erlotinib HCl on the in vivo growth rate of the human NSCLC cell line HCC827. Tumor-bearing animals (8 mice/group) were injected 1 time per week for a total of 3 doses (arrowheads) with vehicle alone, Compound 1 alone, erlotinib HCl alone or a combination of Compound 1 and erlotinib HCl dosed concurrently. Compound 1 was i.v. injected and erlotinib HCl was p.o. dosed. The average tumor volumes for each group (error bars represent SEM) were determined every 2-4 days. Single-agent treatments with either 50 mg/kg body weight of Compound 1, or 25 mg/kg body weight erlotinib HCl, moderately inhibited tumor growth. Concurrent treatment with a combination of 50 mg/kg body weight of Compound 1 plus 25 mg/kg body weight erlotinib HCl dramatically inhibited tumor growth and induced tumor regression. The efficacy observed for the combination treatment group was significantly greater than for either single agent alone ($P<0.05$; one-way ANOVA).
Figure 4:
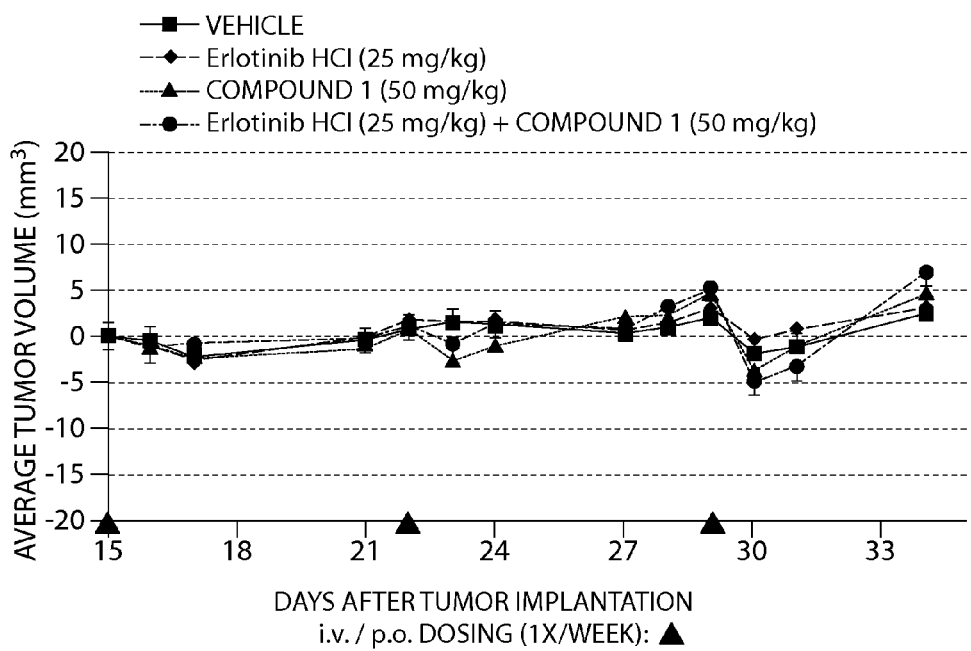
FIG. 4 shows the weight changes to the mice in the experiment detailed in FIG. 3.
Figure 5:
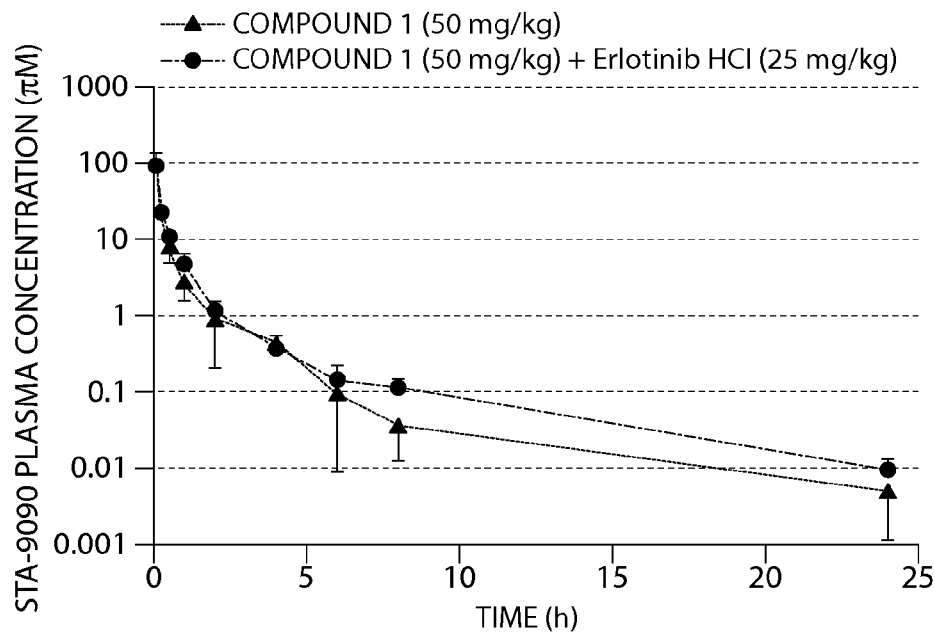
FIG. 5 shows the PK profile of Compound 1 alone and in combination with erlotinib.
Figure 6:
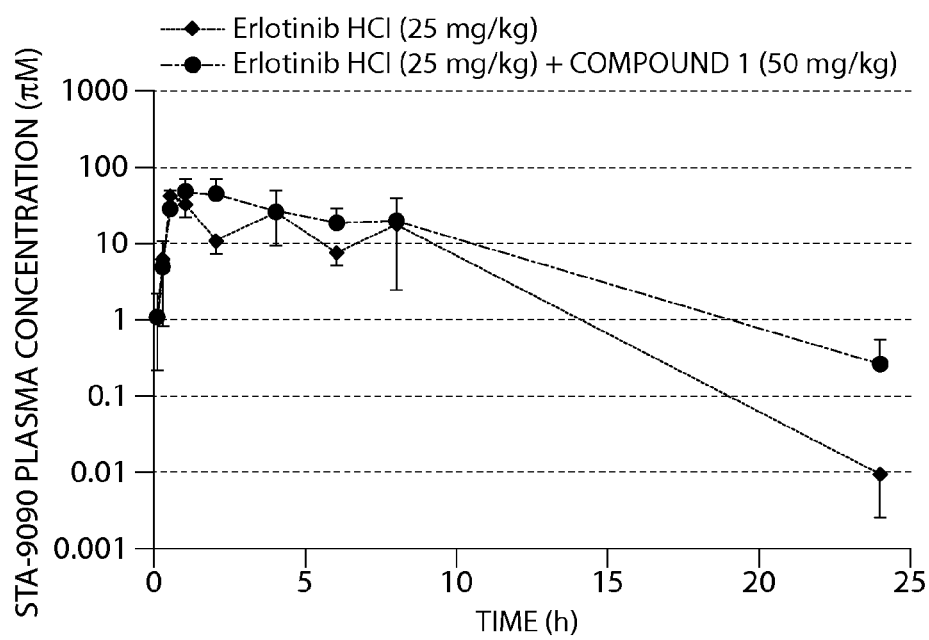
FIG. 6 shows the PK profile of erlotinib alone and in combination with Compound 1.

The combination of Compound 1 and erlotinib HCl was examined in the human HCC827 NSCLC xenograft model. As shown in FIG. 3, treatment with a dose of 50 mg/kg body weight of Compound 1 on a once per week schedule moderately inhibited HCC827 tumor growth in SCID mice, with a % T/C value of 15 observed on day 34. Similarly, treatment with a dose of 25 mg/kg body weight of erlotinib HCl on a once per week schedule moderately inhibited HCC827 tumor growth in SCID mice, with a % T/C value of 23 observed on day 34. In contrast, concurrent treatment with a combination of 50 mg/kg body weight of Compound 1 plus 25 mg/kg body weight erlotinib HCl on a once per week schedule dramatically inhibited tumor growth and induced tumor regression, with a % T/C value of −31 observed on day 34. The efficacy observed for the combination treatment group was significantly greater than that observed for either single-agent group alone (P<0.05; one-way ANOVA). This effect was not associated with excessive toxicity, as the Compound 1 plus erlotinib HCl combination treatment group had an average body-weight change on day 34 relative to the start of the study of +6.9% (+/−1.1 SEM), as compared to +2.4% (+/−1.1 SEM) for the vehicle-treated group. In separate studies, similar results were also observed combining 50 mg/kg Compound 1 with either 15 or 50 mg/kg body weight erlotinib HCl dose on a once per week schedule in this model.

To examine the potential for drug-drug interactions between Compound 1 and erlotinib HCl, an in vivo pharmacokinetic study was conduced. Six to eight week old, female CB17/Icr-Prkdc$^{scid}$/Crl (SCID) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Animals (3/time point) were i.v. dosed a single time with 50 mg/kg body weight Compound 1 alone, 25 mg/kg body weight erlotinib HCl alone, or a combination of 50 mg/kg body weight Compound 1 plus 25 mg/kg body weight erlotinib HCl. Blood samples were withdrawn at multiple time points (0.083, 0.25, 0.5, 1, 2, 4, 6, 8, 24 hr), plasma prepared, and the concentrations of Compound 1 and erlotinib HCl were determined by HPLC. As shown in Table 1, Erlotinib HCl had no significant effect on the plasma half-life (t½), peak plasma concentration ($C_{max}$) or total plasma exposure (AUCinf) of Compound 1. Similarly, Compound 1 had little or no effect on the plasma half-life (ti/2), peak plasma concentration ($C_{max}$) or total plasma exposure (AUCinf) of erlotinib HCl. The 39% increase in total plasma exposure of erlotinib HCl was within the experimental error of this study and, based on the dose response of erlotinib HCl in this model (data not shown), was unlikely to account for the increased efficacy observed for the combination of Compound 1 and erlotinib HCl relative to either single agent alone.

TABLE 1

| TREATMENT | HPLC ANALYTE | DOSE (MG/KG) | T½ (HR) | CMAX (µM) | AUCINF (µMXHR) |
|---|---|---|---|---|---|
| COMPOUND 1 | COMPOUND 1 | 50 | 4.7 | 118 | 38.5 |
| COMPOUND 1 + ERLOTINIB HCL | COMPOUND 1 | 50 | 4.5 | 93.4 | 36.0 |
| ERLOTINIB HCL | ERLOTINIB HCL | 25 | 1.7 | 4.11 | 28.1 |
| ERLOTINIB HCL + COMPOUND 1 | ERLOTINIB HCL | 25 | 2.8 | 4.94 | 39.0 |

In conclusion, the combination of Compound 1 and erlotinib HCl displayed greater efficacy than either single agent alone. Combination treatment did not result in additional toxicity relative to the single agents, with only minimal effects on cumulative average body weight changes over the course of the study. Erlotinib HCl did not affect the plasma exposure of Compound 1 in SCID mice. Compound 1 had little effect on the plasma exposure of erlotinib in SCID mice. Error bars represent+/−SEM for efficacy studies and +/−SD for the PK study.

All publications, patent applications, patents, and other documents cited herein are incorporated by reference in their entirety. In case of conflict, the present specification, including definitions, will control. In addition, the materials, methods, and examples throughout the specification are illustrative only and not intended to be limiting in any way.

What is claimed is:

1. A method of treating non small cell lung cancer in a mammal, comprising administering to the mammal an effective amount of an compound, which is 3-(2,4-dihydroxy-5-isopropyl-phenyl)-4-(1-methyl-indol-5-yl)-5-hydroxy-[1,2,4]triazole, 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, and an effective amount of an EGFR inhibitor, wherein, the EGFR inhibitor is erlotinib and the effective amount of the compound and the effective amount of the EGFR inhibitor together results in a synergistic effect against the non-small cell lung cancer.

2. The method of claim 1, wherein the subject is human.

3. The method of claim 1, wherein the compound is 3-(2,4-dihydroxy-5-isopropyl-phenyl)-4-(1-methyl-indol-5-yl)-5-hydroxy-[1,2,4]triazole, or a tautomer or a pharmaceutically acceptable salt thereof.

* * * * *